(12) United States Patent
Gurer et al.

(10) Patent No.: US 11,910,788 B2
(45) Date of Patent: *Feb. 27, 2024

(54) MOUSE HAVING A HUMANIZED CLUSTER OF DIFFERENTIATION 47 GENE

(71) Applicant: Regeneron Pharmaceuticals, Inc., Tarrytown, NY (US)

(72) Inventors: Cagan Gurer, Chappaqua, NY (US); Ella Ioffe, Bronx, NY (US); Alexander Mujica, Elmsford, NY (US); Gavin Thurston, Briarcliff Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 395 days.

This patent is subject to a terminal disclaimer.

(21) Appl. No.: 17/161,801

(22) Filed: Jan. 29, 2021

(65) Prior Publication Data

US 2021/0161112 A1 Jun. 3, 2021

Related U.S. Application Data

(63) Continuation of application No. 15/982,174, filed on May 17, 2018, now Pat. No. 10,939,673, which is a continuation of application No. 14/951,825, filed on Nov. 25, 2015, now abandoned.

(60) Provisional application No. 62/087,992, filed on Dec. 5, 2014.

(51) Int. Cl.
| | |
|---|---|
| A01K 67/027 | (2006.01) |
| C12N 15/85 | (2006.01) |
| G01N 33/50 | (2006.01) |
| C07K 16/28 | (2006.01) |
| C07K 14/705 | (2006.01) |
| C07K 14/47 | (2006.01) |

(52) U.S. Cl.
CPC ...... *A01K 67/0278* (2013.01); *C07K 14/4703* (2013.01); *C07K 14/705* (2013.01); *C07K 14/70503* (2013.01); *C07K 14/70596* (2013.01); *C07K 16/2803* (2013.01); *C12N 15/8509* (2013.01); *G01N 33/5011* (2013.01); *G01N 33/5014* (2013.01); *G01N 33/5055* (2013.01); *G01N 33/5088* (2013.01); *A01K 2207/12* (2013.01); *A01K 2207/15* (2013.01); *A01K 2217/052* (2013.01); *A01K 2217/072* (2013.01); *A01K 2217/15* (2013.01); *A01K 2227/105* (2013.01); *A01K 2267/0331* (2013.01); *A01K 2267/0381* (2013.01); *C07K 2319/00* (2013.01); *C07K 2319/02* (2013.01); *G01N 2333/70596* (2013.01)

(58) Field of Classification Search
None
See application file for complete search history.

(56) References Cited

U.S. PATENT DOCUMENTS

| | | | |
|---|---|---|---|
| 6,586,251 B2 | 7/2003 | Economides et al. | |
| 7,294,754 B2 | 11/2007 | Poueymirou et al. | |
| 8,354,389 B2 | 1/2013 | Frendewey et al. | |
| 8,518,392 B2 | 8/2013 | Frendewey et al. | |
| 8,697,851 B2 | 4/2014 | Frendewey et al. | |
| 2007/0113297 A1* | 5/2007 | Yang .................. | A01K 67/0271 435/325 |
| 2013/0111616 A1 | 5/2013 | MacDonald et al. | |
| 2013/0111617 A1 | 5/2013 | MacDonald et al. | |
| 2013/0117873 A1 | 5/2013 | Wang et al. | |
| 2014/0134662 A1 | 5/2014 | Flavell et al. | |
| 2014/0245466 A1 | 8/2014 | McDonald et al. | |
| 2014/0245467 A1 | 8/2014 | McDonald et al. | |
| 2014/0369924 A1 | 12/2014 | Weissman et al. | |
| 2015/0089678 A1 | 3/2015 | Murphy et al. | |
| 2015/0106961 A1 | 4/2015 | Rojas et al. | |
| 2015/0143558 A1 | 5/2015 | McWhirter et al. | |
| 2015/0143559 A1 | 5/2015 | McWhirter et al. | |
| 2015/0282463 A1 | 10/2015 | Murphy et al. | |
| 2015/0320021 A1 | 11/2015 | Wang et al. | |
| 2015/0327524 A1 | 11/2015 | Murphy et al. | |
| 2015/0342163 A1 | 12/2015 | Voronina et al. | |
| 2015/0366174 A1 | 12/2015 | Burova et al. | |
| 2016/0345549 A1 | 12/2016 | Gurer et al. | |
| 2017/0164588 A1 | 6/2017 | Olson et al. | |
| 2018/0249689 A1 | 9/2018 | Gurer et al. | |

FOREIGN PATENT DOCUMENTS

| | | |
|---|---|---|
| CN | 101133083 A | 2/2008 |
| CN | 101506235 A | 8/2009 |
| RU | 2 425 880 C2 | 8/2011 |

(Continued)

OTHER PUBLICATIONS

Capecchi, et al Nat. Med. 7, 1086-1090 (Year: 2001).*
Valenzuela et al Nature Biotechnology, 21, 652-659 (Year: 2003).*
Willinger et al Trends in Immunology vol. 32, No. 7, 321-327 (Year: 2011).*

(Continued)

*Primary Examiner* — Anoop K Singh
(74) *Attorney, Agent, or Firm* — Scully, Scott, Murphy & Presser, P.C.; Casey Donahoe

(57) ABSTRACT

Non-human animals, and methods and compositions for making and using the same, are provided, wherein said non-human animals comprise a humanization of an endogenous cluster of differentiation (CD) gene, in particular a humanization of a CD47 gene. Said non-human animals may be described, in some embodiments, as having a genetic modification to an endogenous CD47 gene so that said non-human animals express a CD47 polypeptide that includes a human portion and a non-human portion (e.g., a murine portion).

12 Claims, 9 Drawing Sheets
(8 of 9 Drawing Sheet(s) Filed in Color)
Specification includes a Sequence Listing.

(56) References Cited

FOREIGN PATENT DOCUMENTS

| WO | 2007/033221 A2 | 3/2007 | | |
|---|---|---|---|---|
| WO | 2009/039244 A2 | 3/2009 | | |
| WO | 2011/044050 A2 | 4/2011 | | |
| WO | 2012/112544 A2 | 8/2012 | | |
| WO | 2013/056352 A1 | 4/2013 | | |
| WO | 2013/063556 A1 | 5/2013 | | |
| WO | WO-2013063556 A1 * | 5/2013 | ......... | A01K 67/0275 |
| WO | 2013/144165 A1 | 10/2013 | | |
| WO | 2013/192030 A2 | 12/2013 | | |
| WO | 2014/039782 A2 | 3/2014 | | |
| WO | 2014/071397 A2 | 5/2014 | | |
| WO | 2014/093678 A2 | 6/2014 | | |
| WO | 2015/042557 A1 | 3/2015 | | |
| WO | 2015/057758 A1 | 4/2015 | | |
| WO | 2015/077071 A1 | 5/2015 | | |
| WO | 2015/077072 A1 | 5/2015 | | |
| WO | 2015/171861 A1 | 11/2015 | | |
| WO | 2015/196051 A1 | 12/2015 | | |
| WO | 2016/085889 A1 | 6/2016 | | |

OTHER PUBLICATIONS

Schickel Biochemistry and Cell Biology, 169-176 (Year: 2002).*
Rebres et al The Journal of Bio. Chem., 34607-34616 (Year: 2001).*
Willinger T. et al., "Improving Human Hemato-Lymphoid-System Mice by Cytokine Knock-in Gene Replacement", *Trends in Immunology* 32(7):321-327 (Jul. 2011).
Willinger T. et al., "Human IL-3/GM-CSF Knock-In Mice Support Human Alveolar Macrophage Development and Human Immune Responses in the Lung", *PNAS* 108(6):2390-2395 (Feb. 8, 2011).
Database Accession No. HQ585874, XP-002753825 (2 pages) (Nov. 19, 2010).
Database Accession No. Q08722, XP-002753826 (7 pages) (Nov. 1995).
Database Accession No. E5Q371, XP-002753827 (2 pages) (Feb. 8, 2011).
Brevini T.A.L. et al., "No Shortcuts to Pig Embryonic Stem Cells", *Theriogenology* 74:544-550 (2010).
Cao S. et al., "Isolation and Culture of Primary Bovine Embryonic Stem Cell Colonies by a Novel Method", *Journal of Experimental Zoology* 311A:368-376 (2009).
Dennis Jr. M.B., "Welfare Issues of Genetically Modified Animals", *ILAR Journal* 43(2):100-109 (2002).
Frankel A.E. et al., "Characterization of Diphtheria Fusion Proteins Targeted to the Human Interleukin-3 Receptor", *Protein Engineering* 13(8):575-581 (2000).
Glick B. et al., Moleculyaraya Biotehnologiya. Printsipy i primeneniye. Moscow: Mir, 2002, together with an English-language translation.
Anderson P., "Post-Transcriptional Control of Cytokine Production", *Nature Immunology* 9(4):353-359 (Apr. 2008).
Barclay A.N. et al., "The SIRP Family of Receptors and Immune Regulation", *Nature Reviews—Immunology* 6:457-464 (Jun. 2006).
Brooke G. et al., "Human Lymphocytes Interact Directly With CD47 Through a Novel Member of the Signal Regulatory Protein (SIRP) Family", *The Journal of Immunology* 173:2562-2570 (2004).
Bruce L.J. et al., "A Band 3-Based Macrocomplex of Integral and Peripheral Proteins in the RBC Membrane", *Blood* 101(10):4180-4188 (May 15, 2003).
Chang H.P. et al., "Impaired Memory Retention and Decreased Long-Term Potentiation in Integrin-Associated Protein-Deficient Mice", *Learning & Memory* 6:448-457 (1999).
Chao M P et al., "The CD47-SIRPα Pathway in Cancer Immune Evasion and Potential Therapeutic Implications", *Current Opinion in Immunology* 24:225-232 (2012).
Clark J. et al., "A Future for Transgenic Livestock", *Nature Reviews—Genetics* 4:825-833 (Oct. 2003).
Devoy A. et al., "Genomically Humanized Mice: Technologies and Promises", *Nature Reviews—Genetics* 13:14-20 (Jan. 2012).
Gama Sosa M.A. et al., "Animal Transgenesis: An Overview", *Brain Struct Funct* 214:91-109 (2010).

Gimeno R. et al., "Monitoring the Effect of Gene Silencing by RNA Interference in Human CD34+ Cells Injected into Newborn RAG2-/-γc -/- Mice: Functional Inactivation of p53 in Development T Cells", *Blood* 104(13):3886-3893 (Dec. 15, 2004).
Johansen M.L. et al., "Dual Regulation of SIRPα Phosphorylation by Integrins and CD47", *The Journal of Biological Chemistry* 282(33):24219-24230 (Aug. 17, 2007).
Koshimizu H. et al., "Comprehensive Behavioral Analysis of Cluster of Differentiation 47 Knockout Mice", *PLOS One* 9(2):e89584 (Feb. 2014).
Lavender K.J. et al., "Production of Bone Marrow, Liver, Thymus (BLT) Humanized Mice on the C57BL/6 Rag2-/- γc -/-CD47-/- Background", *Journal of Immunological Methods* 407:127-134 (2014).
Lavender K.J. et al., "BLT-Humanized C57BL/6 Rag2-/- γc -/- CD47-/- Mice are Resistant to GVHD and Develop B- and T-Cell Immunity to HIV Infection", *Blood* 122(25):4013-4020 (Dec. 12, 2013).
Legrand N. et al., "Transient Accumulation of Human Mature Thymocytes and Regulatory T Cells with CD28 Superagonist in "Human Immune System" Rag2-/- γc -/- Mice", *Blood* 108(1):238-245 (Jul. 1, 2006).
Lindberg F.P. et al., "Decreased Resistance to Bacterial Infection and Granulocyte Defects in IAP-Deficient Mice", *Science* 274:795-798 (Nov. 1, 1996).
Muñoz M. et al., "Constraints to Progress in Embryonic Stem Cells from Domestic Species", *Stem Cell Rev and Resp* 5:6-9 (2009).
Mouro-Chanteloup I. et al., "Normal Red Cell Membrane Expression of Rh and Rhag Polypeptides in CD47- Deficient Mice", *Vox Sanguinis* 78:P030 (Jul. 2000).
Mouro-Chanteloup I. et al., "Evidence that the Red Cell Skeleton Protein 4.2 Interacts with the Rh Membrane Complex Member CD47", *Blood* 101(1):338-344 (Jan. 1, 2003).
Navarro-Alvarez N. et al., "CD47: A New Player in Phagocytosis and Xenograft Rejection", *Cellular & Molecular Immunology* 8:285-288 (2011).
Niemann H. et al., "Transgenic Farm Animals: Present and Future", *Rev Sci. Techn. Off. Int. Epiz.* 24(1):285-298 (2005).
Oldenborg P-A et al., "Role of CD47 as a Marker of Self on Red Blood Cells", *Science* 288:2051-2054 (Jun. 16, 2000).
Pan Y. et al., "Studying the Mechanism of CD47-SIRPa Interactions on Red Blood Cells by Single Molecule Force Spectroscopy", *Nanoscale* 6:9951-9964 (2014).
Prelle K. et al., "Pluripotent Stem Cells-Model of Embryonic Development, Tool for Gene Targeting, and Basis of Cell Therapy", *Anat Histo Embryol.* 31(3):169-186 (Jun. 2002).
Poueymirou W.T. et al., "F0 Generation Mice Fully Derived from Gene-Targeted Embryonic Stem Cells Allowing Immediate Phenotypic Analyses", *Nature Biotechnology* 25(1):91-99 (Jan. 2007).
Rebres R.A. et al., "Normal Ligand Binding and Signaling by CD47 (Integrin-Associated Protein) Requires a Long Range Disulfide Bond Between the Extracellular and Membrane-Spanning Domains", *The Journal of Biological Chemistry* 276(37):34607-34616 (Sep. 14, 2001).
Reinhold M.I. et al., "In Vivo Expression of Alternatively Spliced Forms of Integrin-Associated Protein (CD47)", *Journal of Cell Sciences* 108:3419-3425 (1995).
Rendtlew J.M. et al., "Dysregulation of CD47 and the Ligands Thrombospondin 1 and 2 in Multiple Myeloma", *British Journal of Maematology* 138:756-760 (2007).
Ristevski S., "Making Better Transgenic Models", *Molecular Biotechnology* 29:153-163 (2005).
Rongvaux A. et al., "Human Thrombopoietin Knockin Mice Efficiently Support Human Hematopoiesis In Vivo", *PNAS* 108(6):2378-2383 (Feb. 8, 2011).
Sano S-I et al., "Gene Structure of Mouse BIT/SHPS-1", *Biochem. J.* 344:667-675 (1999).
Schickel J. et al., "Gene for Integrin-Associated Protein (IAP, CD47): Physical Mapping, Genomic Structure, and Expression Studies in Skeletal Muscle", *Biochem. Cell Biol.* 80:169-176 (2002).
Shultz L.D. et al., "Humanized Mice for Immune System Investigation: Progress, Promise and Challenges", *Nature Reviews—Immunology* 12:786-798 (Nov. 2012).

(56) References Cited

OTHER PUBLICATIONS

Sick E. et al., "CD47 Updated: A Multifaceted Actor in the Tumour Microenvironment of Potential Therapeutic Interest", British Journal of Pharmacology 167:1415-1430 (2012).
Sigmund C.D., "Viewpoint: Are Studies in Genetically Altered Mice Out of Control?", Arterioscler Thromb Vasc Biol. 20:1425-1429 (2000).
Smith K.R., "Gene Transfer in Higher Animals: Theoretical Considerations and Key Concepts", Journal of Biotechnology 99:1-22 (2002).
Takenaka K. et al., "Polymorphism in Sirpa Modulates Engraftment of Human Hematopoietic Stem Cells", Nature Immunology 8(12):1313-1323 (Dec. 2007).
Tena A. et al., "Transgenic Expression of Human CD47 Markedly Increases Engraftment in a Murine Model of Pig-to-Human Hematopoietic Cell Transplantation", American Journal of Transplantation 14:2713-2722 (2014).
Tena A. et al., "Miniature Swine Expressing Human CD47 to Enhance Bone Marrow Engraftment in Non-Human Primates", Supplement to Transplantation 94(10S):776 (Nov. 27, 2012).
Teraoka Y. et al., "Expression of Recipient CD47 on Rat Insulinoma Cell Xenografts Prevents Macrophage-Mediated Rejection Through SIRPa Inhibitory Signaling in Mice", PLOS One 8(3):e58359 (Mar. 2013).
Traggiai E. et al., "Development of a Human Adaptive Immune System in Cord Blood Cell-Transplanted Mice", Science 304:104-107 (Apr. 2, 2004).
Tseng D. et al., "Anti-CD47 Antibody-Mediated Phagocytosis of Cancer by Macrophages Primes an Effective Antitumor T-Cell Response", PNAS 110(27):11103-11108 (Jul. 2, 2013).
Tulasne D. et al., "C-Terminal Peptide of Thrombospondin-1 Induces Platelet Aggregation Through the Fc Receptor γ-Chain-Associated Signaling Pathway and by Agglutination", Blood 98(12):3346-3352 (Dec. 1, 2001).
Valenzuela D.M. et al., "High-Throughput Engineering of the Mouse Genome Coupled with High-Resolution Expression Analysis", Nature Biotechnology 21(6):652-659 (Jun. 2003).
Verdrengh M. et al., "Integrin-Associated Protein (IAP)-Deficient Mice are Less Susceptible to Development *Staphylococcus Aureus*-Induced Arthritis", Microbes and Infection 1:745-751 (1999).
Waern J.M. et al., "Ectopic Expression of Murine CD47 Minimizes Macrophage Rejection of Human Hepatocyte Xenografts in Immunodeficient Mice", Hepatology 56:1479-1488 (Oct. 2012).

Wang C. et al., "Human CD47 Expression Permits Survival of Porcine Cells in Immunodeficient Mice that Express SIRPα Capable of Binding to Human CD47", Cell Transplantation 20:1915-1920 (2011).
Wang H. et al., "Lack of CD47 on Nonhematopoietic Cells Induces Split Macrophage Tolerance to CD47null Cells", PNAS 104(34):13744-13749 (Aug. 21, 2007).
Wang X-Q et al., "Integrin-Associated Protein Stimulates α2β1-Dependent Chemotaxis Via Gi-Mediated Inhibition of Adenylate Cyclase and Extracellular-Regulated Kinases", The Journal of Cell Biology 147(2):389-399 (Oct. 18, 1999).
Wheeler M.B. et al., "Transgenic Technology and Applications in Swine", Theriogenology 56:1345-1369 (2001).
Harari D. et al., "Bridging the Species Divide: Transgenic Mice Humanized for Type-I Interferon Response", PLoS ONE 9(1):e84259, XP055553720, DOI: 10.1371/journal.pone.0084259 (Jan. 9, 2014).
Hofker M.H. et al., "Transgenic Mouse Methods and Protocols", *Methods in Molecular Biology* 209:51-67 (2002-2003).
Houdebine L-M, "Methods to Generate Transgenic Animals", Genetic Engineering in Livestock, New Applications and Interdisciplinary Perspectives, Engelhard M. et al., XVI, 146, p. 8, illu. pp. 31-47 (2009).
Pakula A.A., "Genetic Analysis of Protein Stability and Function", *Annu. Rev. Genet.* 23:289-310 (1989).
Paris D.B.B.P. et al., "Equine Embryos and Embryonic Stem Cells: Defining Reliable Markers of Pluripotency", *Theriogenology* 74:516-524 (2010).
Rybchin V.N., "Fundamentals of Genetic Engineering", Textbook for High Schools, Saint-Petersburg, Publishing House SPbSTU 522:411-413 (2002).
Zhou H. et al., "Developing tTA Transgenic Rats for Inducible and Reversible Gene Expression", *International Journal of Biological Sciences* 5(2):171-181 (2009).
Russian Office Action and Search Report dated Jun. 3, 2019 received in Russian Patent Application No. 2017123357, together with an English-language translation.
Chinese Office Action dated Mar. 3, 2020 received in Chinese Patent Application No. 201580066047.0, together with an English-language translation.
International Search Report and Written Opinion dated Feb. 26, 2016 received in International Application No. PCT/US2015/062614.

\* cited by examiner

SEQUENCE LISTING

```
<160> NUMBER OF SEQ ID NOS: 36

<210> SEQ ID NO 1
<211> LENGTH: 5591
<212> TYPE: DNA
<213> ORGANISM: Mus musculus

<400> SEQUENCE: 1
gcctacaccg ggagagcagg gaggaggagt tggactgagg ttgggcggct ccgaggtcca      60
gggcgagctt ggccagaggg agtagagagc agcggggctg cgcagggacg cgtgccgtga     120
gttccggtga gcgtgtgtgt cccatgctcc cgtctttcag gccggcccag gacacgaagc     180
cggaagagag ctggctggag ggacgggggc cgtgagcaga gagtgcaacc cgcgcagccc     240
cggggacagg ctgattcttg gcgctctccg ccggagcctg cccagggctg ggtgtgaggc     300
```

```
tggcgtcacg tcaacgagca gaggcggcca ggcggggcgg agtgcgcgtg cgcggggcgg    360
cgagcacgcg cgcgcgcgca cccccgggca gcctgggcgg ccgctcctgc ctgtcactgc    420
tgcggcgctg ctggtcggtc gtttcccttg aaggcagcag cggaggcggc ggctgctcca    480
gacacctgcg gcgcgaccc cccggcggcg cggagatgtg gcccttggcg gcggcgctgt     540
tgctgggctc ctgctgctgc ggttcagctc aactactgtt tagtaacgtc aactccatag    600
agttcacttc atgcaatgaa actgtggtca tcccttgcat cgtccgtaat gtggaggcgc    660
aaagcaccga agaaatgttt gtgaagtgga agttgaacaa atcgtatatt ttcatctatg    720
atggaaataa aaatagcact actacagatc aaaactttac cagtgcaaaa atctcagtct    780
cagacttaat caatggcatt gcctctttga aaatggataa gcgcgatgcc atggtgggaa    840
actacacttg cgaagtgaca gagttatcca gagaaggcaa aacagttata gagctgaaaa    900
accgcacggc cttcaacact gaccaaggat cagcctgttc ttacgaggag gagaaggag     960
gttgcaaatt agtttcgtgg ttttctccaa atgaaaagat cctcattgtt attttcccaa   1020
ttttggctat actcctgttc tggggaaagt tggtatttt aacactcaaa tataaatcca    1080
gccatacgaa taagagaatc attctgctgc tcgttgccgg gctggtgctc acagtcatcg   1140
tggttgttgg agccatcctt ctcatcccag agaaaagcc cgtgaagaat gcttctggac    1200
ttggcctcat tgtaatctct acggggatat taatactact tcagtacaat gtgtttatga   1260
cagcttttgg aatgacctct ttcaccattg ccatattgat cactcaagtg ctgggctacg   1320
tccttgcttt ggtcgggctg tgtctctgca tcatggcatg tgagccagtg cacggccccc   1380
ttttgatttc aggtttgggg atcatagctc tagcagaact acttggatta gtttatatga   1440
agtttgtcga ataggtgaag ggaagtgacg gactgtaact tggaagtcag aaatggaaga   1500
atacagttgt ctaagcacca ggtcttcacg actcacagct ggaaggaaca gacaacagta   1560
actgacttcc atccaggaaa acatgtcaca taaatgatta ctaagtttat attcaaagca   1620
gctgtacttt acataataaa aaaaatatga tgtgctgtgt aaccaattgg aatcccattt   1680
ttctattgtt tctactcaac taggggcaaa cgtttcaggg gcaacttcca agaatgatgc   1740
ttgttagatc ctagagtctc tgaacactga gtttaaattg attccgagtg agactcgcca   1800
agcactaacc tgagggttag ttacccagag ataccatga aaaacagtgg tatccagcaa    1860
gccttagtaa actcaggttg ccagcagctt tgccacttcc gctgctagct gaataacaag   1920
actgccactt ctgggtcata gtgatagaga ctgaagtaga aaacgaatg tggttgggca    1980
aatcccgtgt ggcccctctg tgtgctatga tattgatggc actggtgtct tcattcttgg   2040
gggttgccat cattcacaca cacccctttg acatacagtg caccccagtt ttgaatacat   2100
ttttttttgca ccctgtcccg ttctgctact ttgatttgcg ttatgatata tatatatata  2160
tataatacct tttctcctct ttaaacatgg tcctgtgaca caatagtcag ttgcagaaag   2220
gagccagact tattcgcaaa gcactgtgct caaactcttc agaaaaaaag gaaaaaaaa    2280
aaaagctata gttgtaacat atgtattcca gacctctggt ttaaaggcaa agaaaaaaa    2340
atctacagtg tttcttctca tgtttctga tcggaggcat gacaaagcaa gactgaaatc    2400
tgaactgtgt ctcctgcatg gcaacacgtg tctccgtcag gccctcgcaa ggcccgggga   2460
gggggttcta cgcctcttgt ctctttgttg catgctgaac actcatcgcc ttcctactgt   2520
atcctgcctc ctgcagcctc cctcttcctc ctcctcttcc tcttcctcct cttcctcctc   2580
ctcctcctct tcctccaagt ttgaaaggtc aaacaaaact accacattcc ctacccagtt   2640
```

```
agaagaaaac caccgtcctg acagttgtga tcgcatggag tacttttaga ttattagcac   2700
ctgttttac ctcgtttgtg ggcgtgtttg tatgtgcaca tgtatgaagt cggcacatgc   2760
accttctgta tgggcagagg cgtggcatct acagaagagc agatgccaac tttgtgcttt   2820
tagtgaatac attaaaaaaa aaaaaccaac ggtccttatt gagtggaatt ctatttgatg   2880
caaatatttg agctctttaa gactttaaaa ctagataatg tgccaagctt ttaggactgc   2940
tcaccagtgc cctctgaaga aacaccagta cttttttcctg tttgtgtaat aaaggcatat   3000
ttgtatttgt gtttgcatca ctaatggtta tttcttctta gtccactgaa tgtttccatg   3060
tgcctctcgt atgccaaact ttttgtcatc tttcatgtgg ggaccaaatg gtttgtctgt   3120
ggcaaaccta aacctatgac ctgctgaggc ctctcagaaa actgaccaca gtaccaagat   3180
agtacttcgc aaagaaaagt aggttccctc cctggttttg tagctgtcgc aatattagc   3240
gtaattccaa ggagctgaac gcctttatat aaatctgatg gcacctgatg cttttagttc   3300
tgaaaatatt tacactcgga tcatgttgtt gatgacttaa acaaagtttt gatgaagaga   3360
gcaaaaaaaa agcaggtgga tttggaacag tttcagggtt tttttttgtt tttgttttttt   3420
gttttgttt tttttttttt attttttgttt ttctgttctc tgttagaaaa gtcaggtgtt   3480
ctctgtcagg ctatctttat agtcaatttt ttttacgaac taaagtagta ccttttaata   3540
tgtagtcaac gcccctctgc tcggggttca gttttgggtc ttaaccagct gtcatgttct   3600
ctatgctgcc tgccacttga ggcactgagt gccctagaca gtcccatcgg tggtagccag   3660
ggaaacgaaa gacgaactca actcttgctc ctaataatca actctctgta tgaaggatgg   3720
cagcattaag agtcctcctg cctgggcatt attgggccag ttcaccctct ttaaatcaaa   3780
cccgcagtgg ctcccagttc tcgtcccatc agatttaaat tgctaacagt atgggggca   3840
ccacgcatct gttttgtccc acaatgcgct tttctctccc aaatcccgat ttctgctgtc   3900
atagcctcta ttcaattttt atttattgtc tgccctccac ttatacaatc gtagagagca   3960
atgccatttg tcacttttctg caacagtttt ttgagccttt atggctgaat cccattttc   4020
ttctctttca aactgtttgc tccattgctc ctcccgcacg gctgtccgta cagtcatccc   4080
atccatctgg gggcctcttt catctctcac ccttcctggt gcttcgtgga tctctgctta   4140
cctctgtggg tttttttttt tttttttgac ttattcttct cactggactt taagattact   4200
tccacagcga aagtgctgcc tccctttcct gcccgcagtg ttctgcgtac tttagatact   4260
actcagtgct gacatttgat ggcaaaagtt gcctgcactt aaatttctct ttttaatagg   4320
gtgaactaga gttggagttt ttttctcttt ttttctctttt ctctctctct ctctctctct   4380
ctctctctct ctctctctct ctccctccct ccctccctcc ctccctccct ccctctctct   4440
ctcttttttct ttcttttcttt cttttcttttct ttcttttcttt cttttcttttct ttctttcttt   4500
ttttgacaaa tctcacaggc tttgagaatt ataaaggtg acagttcacc tgaaaatcac   4560
aggtctggtc tgtttaaatt gttgagaaat atccgattaa aagtcttgtg gctgtgtcct   4620
aataggctct ctttcaggac gttgtagtca atagagtggc tgaaccatac ttgagtttat   4680
aaagctcaaa aactgatgca cccactctgc tattatcgtg ttagtaagag ttcagctgta   4740
tatcattgtc taggtttatc ttgtcctaca gtgggtattc aaatatggcc accagaggat   4800
atgtgtaaat ataagcacct gtatttgcct gttgttgaga actggaggga aaacaaaaaa   4860
tgtctggcaa ccctttgcct ttttaaccgt aattaattga cagtttattt agagataaga   4920
gttttcaaaa atctccttaac tgccacaacc cacagagggt cttgttttgc catcttcagt   4980
ggctcacaga tatgatccaa gttaacttga aagagatgag cagtacccag gaaattgtcc   5040
```

```
tgcctttaac tctggctgtc cttaattatg actgtttaat gctgaatttt ccatccgtct    5100
agtgtttgag ggtaaagaaa agcctttttt aaataagtat ttctgtaaaa cggcatcggt    5160
gggatcttct gtgttgctat cacgggtgaa agagggaaac atttcttatt tttattaagc    5220
agagcattat ttacagaaag ccattgttga gaattagttc ccacatcata taaatatcca    5280
ttaaccattc taaattgtaa gagaactcca gtgttgctat gcacaaggaa ctctcctggg    5340
ggccttttt tgcatagcaa ttaaaggtat gctatttgtc agtagccatt ttttgcagtg    5400
atttaaagac caaagttgtt ttacagctgt gttacccta aaggtttttt ttttatgtat    5460
taaatcaatt tatcactgtt tgaagctttg aatacctgca atctttgcca agatactttt    5520
ttatttaaaa aaataactgt gtaaatatta ccctgtaata ttatatatac ttaataaaac    5580
attttaagct a                                                         5591
```

<210> SEQ ID NO 2
<211> LENGTH: 312
<212> TYPE: PRT
<213> ORGANISM: Mus musculus

<400> SEQUENCE: 2

```
Met Trp Pro Leu Ala Ala Leu Leu Leu Gly Ser Cys Cys Cys Gly
 1               5                  10                  15

Ser Ala Gln Leu Leu Phe Ser Asn Val Asn Ser Ile Glu Phe Thr Ser
                20                  25                  30

Cys Asn Glu Thr Val Val Ile Pro Cys Ile Val Arg Asn Val Glu Ala
            35                  40                  45

Gln Ser Thr Glu Glu Met Phe Val Lys Trp Lys Leu Asn Lys Ser Tyr
        50                  55                  60

Ile Phe Ile Tyr Asp Gly Asn Lys Asn Ser Thr Thr Asp Gln Asn
 65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Ala Phe Asn Thr Asp Gln Gly Ser Ala Cys Ser Tyr Glu
    130                 135                 140

Glu Glu Lys Gly Gly Cys Lys Leu Val Ser Trp Phe Ser Pro Asn Glu
145                 150                 155                 160

Lys Ile Leu Ile Val Ile Phe Pro Ile Leu Ala Ile Leu Leu Phe Trp
                165                 170                 175

Gly Lys Phe Gly Ile Leu Thr Leu Lys Tyr Lys Ser Ser His Thr Asn
            180                 185                 190

Lys Arg Ile Ile Leu Leu Val Ala Gly Leu Val Leu Thr Val Ile
        195                 200                 205

Val Val Val Gly Ala Ile Leu Ile Pro Gly Glu Lys Pro Val Lys
    210                 215                 220

Asn Ala Ser Gly Leu Gly Leu Ile Val Ile Ser Thr Gly Ile Leu Ile
225                 230                 235                 240

Leu Leu Gln Tyr Asn Val Phe Met Thr Ala Phe Gly Met Thr Ser Phe
                245                 250                 255

Thr Ile Ala Ile Leu Ile Thr Gln Val Leu Gly Tyr Val Leu Ala Leu
            260                 265                 270
```

Val Gly Leu Cys Leu Cys Ile Met Ala Cys Glu Pro Val His Gly Pro
        275                 280                 285

Leu Leu Ile Ser Gly Leu Gly Ile Ile Ala Leu Ala Glu Leu Leu Gly
    290                 295                 300

Leu Val Tyr Met Lys Phe Val Glu
305                 310

<210> SEQ ID NO 3
<211> LENGTH: 5560
<212> TYPE: DNA
<213> ORGANISM: Mus musculus

<400> SEQUENCE: 3

| | | | | | |
|---|---|---|---|---|---|
| gcctacaccg | ggagagcagg | gaggaggagt | tggactgagg | ttgggcggct | ccgaggtcca | 60 |
| gggcgagctt | ggccagaggg | agtagagagc | agcggggctg | cgcagggacg | cgtgccgtga | 120 |
| gttccggtga | gcgtgtgtgt | cccatgctcc | cgtctttcag | gccggcccag | gacacgaagc | 180 |
| cggaagagag | ctggctggag | ggacggggggc | cgtgagcaga | gagtgcaacc | cgcgcagccc | 240 |
| cggggacagg | ctgattcttg | gcgctctccg | ccggagcctg | cccagggctg | gtgtgaggc | 300 |
| tggcgtcacg | tcaacgagca | gaggcggcca | ggcggggcgg | agtgcgcgtg | cgcggggcgg | 360 |
| cgagcacgcg | cgcgcgcgca | ccccggggca | gcctgggcgg | ccgctcctgc | ctgtcactgc | 420 |
| tgcggcgctg | ctggtcggtc | gtttcccttg | aaggcagcag | cggaggcggc | ggctgctcca | 480 |
| gacacctgcg | gcggcgaccc | ccggcggcg | cggagatgtg | gcccttggcg | gcggcgctgt | 540 |
| tgctgggctc | ctgctgctgc | ggttcagctc | aactactgtt | tagtaacgtc | aactccatag | 600 |
| agttcacttc | atgcaatgaa | actgtggtca | tcccttgcat | cgtccgtaat | gtggaggcgc | 660 |
| aaagcaccga | agaaatgttt | gtgaagtgga | agttgaacaa | atcgtatatt | ttcatctatg | 720 |
| atggaaataa | aaatagcact | actacagatc | aaaactttac | cagtgcaaaa | atctcagtct | 780 |
| cagacttaat | caatggcatt | gcctctttga | aaatggataa | gcgcgatgcc | atggtgggaa | 840 |
| actacacttg | cgaagtgaca | gagttatcca | gagaaggcaa | aacagttata | gagctgaaaa | 900 |
| accgcacggt | tcgtggtttt | ctccaaatg | aaaagatcct | cattgttatt | ttcccaattt | 960 |
| tggctatact | cctgttctgg | ggaaagtttg | gtattttaac | actcaaatat | aaatccagcc | 1020 |
| atacgaataa | gagaatcatt | ctgctgctcg | ttgccgggct | ggtgctcaca | gtcatcgtgg | 1080 |
| ttgttggagc | catccttctc | atcccaggag | aaaagcccgt | gaagaatgct | tctggacttg | 1140 |
| gcctcattgt | aatctctacg | gggatattaa | tactacttca | gtacaatgtg | tttatgacag | 1200 |
| cttttggaat | gacctctttc | accattgcca | tattgatcac | tcaagtgctg | ggctacgtcc | 1260 |
| ttgctttggt | cgggctgtgt | ctctgcatca | tggcatgtga | gccagtgcac | ggccccccttt | 1320 |
| tgatttcagg | tttggggatc | atagctctag | cagaactact | tggattagtt | tatatgaagt | 1380 |
| ttgtcgcttc | caaccagagg | actatccaac | ctcctaggaa | taggtgaagg | gaagtgacgg | 1440 |
| actgtaactt | ggaagtcaga | aatggaagaa | tacagttgtc | taagcaccag | gtcttcacga | 1500 |
| ctcacagctg | gaaggaacag | acaacagtaa | ctgacttcca | tccaggaaaa | catgtcacat | 1560 |
| aaatgattac | taagtttata | ttcaaagcag | ctgtactta | cataataaaa | aaatatgat | 1620 |
| gtgctgtgta | accaattgga | atcccatttt | tctattgttt | ctactcaact | aggggcaaac | 1680 |
| gtttcagggg | caacttccaa | gaatgatgct | tgttagatcc | tagagtctct | gaacactgag | 1740 |
| tttaaattga | ttccgagtga | gactcgccaa | gcactaacct | gagggttagt | tacccagaga | 1800 |
| tacctatgaa | aaacagtggt | atccagcaag | ccttagtaaa | ctcaggttgc | cagcagcttt | 1860 |

```
gccacttccg ctgctagctg aataacaaga ctgccacttc tgggtcatag tgatagagac    1920
tgaagtagaa aaacgaatgt ggttgggcaa atcccgtgtg gccctctgt gtgctatgat     1980 attgatggca ctggtgtctt cattcttggg ggttgccatc attcacacac acccctttga    2040
catacagtgc accccagttt tgaatacatt tttttgcac cctgtcccgt tctgctactt     2100
tgatttgcgt tatgatatat atatatatat ataataccttt ttctcctctt taaacatggt   2160
cctgtgacac aatagtcagt tgcagaaagg agccagactt attcgcaaag cactgtgctc    2220
aaactcttca gaaaaaagg aaaaaaaaaa aaagctatag ttgtaacata tgtattccag     2280
acctctggtt taaaggcaaa agaaaaaaaa tctacagtgt ttcttctcat gttttctgat    2340
cggaggcatg acaaagcaag actgaaatct gaactgtgtc tcctgcatgg caacacgtgt    2400
ctccgtcagg ccctcgcaag gcccggggag ggggttctac gcctcttgtc tctttgttgc    2460
atgctgaaca ctcatcgcct tcctactgta tcctgcctcc tgcagcctcc ctcttcctcc    2520
tcctcttcct cttcctcctc ttcctcctcc tcctcctctt cctccaagtt tgaaaggtca    2580
aacaaaacta ccacattccc tacccagtta gaagaaaacc accgtcctga cagttgtgat   2640
cgcatggagt acttttagat tattagcacc tgttttttacc tcgtttgtgg gcgtgtttgt   2700
atgtgcacat gtatgaagtc ggcacatgca ccttctgtat gggcagaggc gtggcatcta    2760
cagaagagca gatgccaact ttgtgctttt agtgaataca ttaaaaaaaa aaaaccaacg    2820
gtccttattg agtggaattc tatttgatgc aaatatttga gctctttaag actttaaaac   2880
tagataatgt gccaagcttt taggactgct caccagtgcc ctctgaagaa acaccagtac    2940 ttttcctgt tgtgtaata aaggcatatt tgtatttgtg tttgcatcac taatggttat     3000
ttcttcttag tccactgaat gtttccatgt gcctctcgta tgccaaactt tttgtcatct    3060
ttcatgtggg gaccaaatgg tttgtctgtg gcaaacctaa acctatgacc tgctgaggcc    3120
tctcagaaaa ctgaccacag taccaagata gtacttcgca aagaaaagta ggttccctcc    3180
ctggttttgt agctgtcgcc aatattagcg taattccaag gagctgaacg cctttatata    3240
aatctgatgg cacctgatgc ttttagttct gaaaatattt acactcggat catgttgttg    3300
atgacttaaa caaagttttg atgaagagag caaaaaaaaa gcaggtggat ttggaacagt    3360
ttcagggttt ttttttgtttt ttgttttttg ttttttgtttt ttttttttta ttttgtttt   3420 tctgttctct gttagaaaag tcaggtgttc tctgtcaggc tatctttata gtcaattttt   3480
tttacgaact aaagtagtac ctttaatat gtagtcaacg cccctctgct cggggttcag     3540
ttttgggtct taaccagctg tcatgttctc tatgctgcct gccacttgag gcactgagtg    3600
ccctagacag tcccatcggt ggtagccagg gaaacgaaag acgaactcaa ctcttgctcc    3660
taataatcaa ctctctgtat gaaggatggc agcattaaga gtcctcctgc ctgggcatta    3720
ttgggccagt tcaccctctt taaatcaaac ccgcagtggc tcccagttct cgtcccatca    3780
gatttaaatt gctaacagta tggggggcac cacgcatctg ttttgtccca caatgcgctt   3840
ttctctccca aatcccgatt tctgctgtca tagcctctat tcaatttta tttattgtct    3900 gccctccact tatacaatcg tagagagcaa tgccatttgt cactttctgc aacagttttt    3960 tgagcctta tggctgaatc ccattttct tctctttcaa actgtttgct ccattgctcc     4020
tcccgcacgg ctgtccgtac agtcatccca tccatctggg ggcctctttc atctctcacc   4080
cttcctggtg cttcgtggat ctctgcttac ctctgtgggt ttttttttt tttttttgact   4140 tattcttctc actggacttt aagattactt ccacagcgaa agtgctgcct ccctttctg    4200
```

```
cccgcagtgt tctgcgtact ttagatacta ctcagtgctg acatttgatg gcaaaagttg      4260
cctgcactta aatttctctt tttaataggg tgaactagag ttggagtttt tttctctttt      4320
ttctcttttc tctctctctc tctctctctc tctctctctc tctctctctc tccctccctc      4380
cctccctccc tccctccctc cctctctctc tcttttctct tctttcttc tttctttctt       4440 tctttctttc tttctttctt tctttctttt tttgacaaat ctcacaggct ttgagaatta      4500
taaaaggtga cagttcacct gaaaatcaca ggtctggtct gtttaaattg ttgagaaata      4560
tccgattaaa agtcttgtgg ctgtgtccta ataggctctc tttcaggacg ttgtagtcaa      4620
tagagtggct gaaccatact tgagtttata aagctcaaaa actgatgcac ccactctgct      4680
attatcgtgt tagtaagagt tcagctgtat atcattgtct aggtttatct tgtcctacag      4740
tgggtattca aatatggcca ccagaggata tgtgtaaata taagcacctg tatttgcctg      4800
ttgttgagaa ctggagggaa aacaaaaaat gtctggcaac cctttgcctt tttaaccgta      4860
attaattgac agtttattta gagataagag ttttcaaaaa tctcttaact gccacaaccc      4920
acagagggtc ttgttttgcc atcttcagtg gctcacagat atgatccaag ttaacttgaa      4980
agagatgagc agtacccagg aaattgtcct gcctttaact ctggctgtcc ttaattatga      5040
ctgtttaatg ctgaattttc catccgtcta gtgtttgagg gtaaagaaaa gcctttttta      5100
aataagtatt tctgtaaaac ggcatcggtg ggatcttctg tgttgctatc acgggtgaaa      5160
gagggaaaca tttcttatt ttattaagca gagcattatt tacagaaagc cattgttgag       5220
aattagttcc cacatcatat aaatatccat taaccattct aaattgtaag agaactccag      5280
tgttgctatg cacaaggaac tctcctgggg gcctttttt gcatagcaat taaaggtatg       5340
ctatttgtca gtagccattt tttgcagtga tttaaagacc aaagttgttt tacagctgtg      5400
ttacccttaa aggttttttt tttatgtatt aaatcaattt atcactgttt gaagctttga      5460
atacctgcaa tctttgccaa gatactttt tatttaaaaa aataactgtg taaatattac       5520
cctgtaatat tatatatact taataaaaca ttttaagcta                            5560
```

<210> SEQ ID NO 4
<211> LENGTH: 303
<212> TYPE: PRT
<213> ORGANISM: Mus musculus

<400> SEQUENCE: 4

Met Trp Pro Leu Ala Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Val Ser Trp Phe Ser Pro Asn Glu Lys Ile Leu Ile Val

```
                130              135              140
Ile Phe Pro Ile Leu Ala Ile Leu Leu Phe Trp Gly Lys Phe Gly Ile
145                 150                  155                 160

Leu Thr Leu Lys Tyr Lys Ser Ser His Thr Asn Lys Arg Ile Ile Leu
                165                  170                 175

Leu Leu Val Ala Gly Leu Val Leu Thr Val Ile Val Val Gly Ala
            180                  185                 190

Ile Leu Leu Ile Pro Gly Glu Lys Pro Val Lys Asn Ala Ser Gly Leu
            195                  200                 205

Gly Leu Ile Val Ile Ser Thr Gly Ile Leu Ile Leu Gln Tyr Asn
            210                  215                 220

Val Phe Met Thr Ala Phe Gly Met Thr Ser Phe Thr Ile Ala Ile Leu
225                 230                  235                 240

Ile Thr Gln Val Leu Gly Tyr Val Leu Ala Leu Val Gly Leu Cys Leu
                245                  250                 255

Cys Ile Met Ala Cys Glu Pro Val His Gly Pro Leu Leu Ile Ser Gly
                260                  265                 270

Leu Gly Ile Ile Ala Leu Ala Glu Leu Leu Gly Leu Val Tyr Met Lys
            275                  280                 285

Phe Val Ala Ser Asn Gln Arg Thr Ile Gln Pro Pro Arg Asn Arg
290                 295                  300
```

<210> SEQ ID NO 5
<211> LENGTH: 5648
<212> TYPE: DNA
<213> ORGANISM: Mus musculus

<400> SEQUENCE: 5

```
gcctacaccg ggagagcagg gaggaggagt tggactgagg ttgggcggct ccgaggtcca      60
gggcgagctt ggccagaggg agtagagagc agcggggctg cgcagggacg cgtgccgtga     120
gttccggtga gcgtgtgtgt cccatgctcc cgtctttcag gccggcccag gacacgaagc     180
cggaagagag ctggctggag ggacgggggc cgtgagcaga gagtgcaacc cgcgcagccc     240
cggggacagg ctgattcttg gcgctctccg ccggagcctg cccagggctg ggtgtgaggc     300
tggcgtcacg tcaacgagca gaggcggcca ggcggggcgg agtgcgcgtg cgcggggcgg     360
cgagcacgcg cgcgcgcgca ccccgggca ggctgggcgg ccgctcctgc ctgtcactgc     420
tgcggcgctg ctggtcggtc gtttcccttg aaggcagcag cggaggcggc ggctgctcca     480
gacacctgcg gcggcgaccc cccggcggcg cggagatgtg gcccttggcg gcggcgctgt     540
tgctgggctc ctgctgctgc ggttcagctc aactactgtt tagtaacgtc aactccatag     600
agttcacttc atgcaatgaa actgtggtca tcccttgcat cgtccgtaat gtggaggcgc     660
aaagcaccga agaaatgttt gtgaagtgga gttgaacaa atcgtatatt ttcatctatg     720
atggaaataa aaatagcact actacagatc aaaactttac cagtgcaaaa atctcagtct     780
cagacttaat caatggcatt gcctctttga aatggataa gcgcgatgcc atggtgggaa     840
actacacttg cgaagtgaca gagttatcca gagaaggcaa aacagttata gagctgaaaa     900
accgcacggc cttcaacact gaccaaggat cagcctgttc ttacgaggag agaaaggag     960
gttgcaaatt agtttcgtgg ttttctccaa atgaaaagat cctcattgtt attttcccaa    1020
ttttggctat actcctgttc tggggaaagt ttggtatttt aacactcaaa tataaatcca    1080
gccatacgaa taagagaatc attctgctgc tcgttgccgg gctggtgctc acagtcatcg    1140
tggttgttgg agccatcctt ctcatcccag gagaaaagcc cgtgaagaat gcttctggac    1200
```

```
ttggcctcat tgtaatctct acggggatat taatactact tcagtacaat gtgtttatga    1260
cagcttttgg aatgacctct ttcaccattg ccatattgat cactcaagtg ctgggctacg    1320
tccttgcttt ggtcgggctg tgtctctgca tcatggcatg tgagccagtg cacggccccc    1380
ttttgatttc aggtttgggg atcatagctc tagcagaact acttggatta gtttatatga    1440
agtttgtcgc ttccaaccag aggactatcc aacctcctag gaaagctgta gaggaacccc    1500
ttaacgaata ggtgaaggga agtgacggac tgtaacttgg aagtcagaaa tggaagaata    1560
cagttgtcta agcaccaggt cttcacgact cacagctgga aggaacagac aacagtaact    1620
gacttccatc caggaaaaca tgtcacataa atgattacta agtttatatt caaagcagct    1680
gtactttaca aataaaaaaa aatatgatgt gctgtgtaac caattggaat cccattttc     1740 tattgtttct actcaactag gggcaaacgt ttcaggggca acttccaaga atgatgcttg    1800
ttagatccta gagtctctga acactgagtt taaattgatt ccgagtgaga ctcgccaagc    1860
actaacctga gggttagtta cccagagata cctatgaaaa acagtggtat ccagcaagcc    1920
ttagtaaact caggttgcca gcagctttgc cacttccgct gctagctgaa taacaagact    1980
gccacttctg ggtcatagtg atagagactg aagtagaaaa acgaatgtgg ttgggcaaat    2040
cccgtgtggc ccctctgtgt gctatgatat tgatggcact ggtgtcttca ttcttggggg    2100
ttgccatcat tcacacacac ccctttgaca tacagtgcac cccagttttg aatacatttt    2160
ttttgcaccc tgtcccgttc tgctactttg atttgcgtta tgatatatat atatatatat    2220 aataccttt ctcctctta aacatggtcc tgtgacacaa tagtcagttg cagaaaggag    2280
ccagacttat tcgcaaagca ctgtgctcaa actcttcaga aaaaaaggaa aaaaaaaaa    2340 agctatagtt gtaacatatg tattccagac ctctggttta aaggcaaaag aaaaaaaatc    2400
tacagtgttt cttctcatgt tttctgatcg gaggcatgac aaagcaagac tgaaatctga    2460
actgtgtctc ctgcatggca acacgtgtct ccgtcaggcc ctcgcaaggc ccggggaggg    2520
ggttctacgc ctcttgtctc tttgttgcat gctgaacact catcgccttc ctactgtatc    2580
ctgcctcctg cagcctccct cttcctcctc ctcttcctct tcctcctctt cctcctcctc    2640
ctcctcttcc tccaagtttg aaaggtcaaa caaaactacc acattcccta cccagttaga    2700
agaaaaccac cgtcctgaca gttgtgatcg catggagtac ttttagatta ttagcacctg    2760
tttttacctc gtttgtgggc gtgtttgtat gtgcacatgt atgaagtcgg cacatgcacc    2820
ttctgtatgg gcagaggcgt ggcatctaca gaagagcaga tgccaacttt gtgcttttag    2880
tgaatacatt aaaaaaaaaa aaccaacggt ccttattgag tggaattcta tttgatgcaa    2940
atatttgagc tctttaagac tttaaaacta gataatgtgc caagctttta ggactgctca    3000
ccagtgccct ctgaagaaac accagtactt tttcctgttt gtgtaataaa ggcatatttg    3060
tatttgtgtt tgcatcacta atggttattt cttcttagtc cactgaatgt tccatgtgc     3120 ctctcgtatg ccaaacttt tgtcatcttt catgtgggga ccaaatggtt tgtctgtggc    3180
aaacctaaac ctatgacctg ctgaggcctc tcagaaaact gaccacagta ccaagatagt    3240
acttcgcaaa gaaagtaggt tccctccct ggttttgtag ctgtcgccaa tattagcgta    3300
attccaagga gctgaacgcc tttatataaa tctgatggca cctgatgctt ttagttctga    3360
aaatatttac actcggatca tgttgttgat gacttaaaca aagttttgat gaagagagca    3420
aaaaaaaagc aggtggattt ggaacagttt caggggttttt tttgttttttt gtttttttgtt    3480 tttgtttttt ttttttttatt tttgttttc tgttctctgt tagaaaagtc aggtgttctc    3540
```

| | | | | |
|---|---|---|---|---|
| tgtcaggcta | tctttatagt | caattttttt | tacgaactaa | agtagtacct | tttaatatgt | 3600 |
| agtcaacgcc | cctctgctcg | gggttcagtt | ttgggtctta | accagctgtc | atgttctcta | 3660 |
| tgctgcctgc | cacttgaggc | actgagtgcc | ctagacagtc | ccatcggtgg | tagccaggga | 3720 |
| aacgaaagac | gaactcaact | cttgctccta | ataatcaact | ctctgtatga | aggatggcag | 3780 |
| cattaagagt | cctcctgcct | gggcattatt | gggccagttc | accctcttta | aatcaaaccc | 3840 |
| gcagtggctc | ccagttctcg | tcccatcaga | tttaaattgc | taacagtatg | ggggcacca | 3900 |
| cgcatctgtt | ttgtcccaca | atgcgctttt | ctctcccaaa | tcccgatttc | tgctgtcata | 3960 |
| gcctctattc | aatttttatt | tattgtctgc | cctccactta | tacaatcgta | gagagcaatg | 4020 |
| ccatttgtca | ctttctgcaa | cagttttttg | agcctttatg | gctgaatccc | attttcttc | 4080 |
| tctttcaaac | tgtttgctcc | attgctcctc | ccgcacggct | gtccgtacag | tcatcccatc | 4140 |
| catctggggg | cctctttcat | ctctcaccct | tcctggtgct | tcgtggatct | ctgcttacct | 4200 |
| ctgtgggttt | tttttttttt | ttttgactta | ttcttctcac | tggactttaa | gattacttcc | 4260 |
| acagcgaaag | tgctgcctcc | cttttctgcc | cgcagtgttc | tgcgtacttt | agatactact | 4320 |
| cagtgctgac | atttgatggc | aaaagttgcc | tgcacttaaa | tttctctttt | taataggtg | 4380 |
| aactagagtt | ggagttttt | tctctttttt | ctcttttctc | tctctctctc | tctctctctc | 4440 |
| tctctctctc | tctctctctc | cctccctccc | tccctccctc | cctccctccc | tctctctctc | 4500 |
| tttttcttc | tttcttcctt | tctttctttc | tttcttctt | tctttcttc | tttcttttt | 4560 |
| tgacaaatct | cacaggcttt | gagaattata | aaggtgaca | gttcacctga | aaatcacagg | 4620 |
| tctggtctgt | ttaaattgtt | gagaaatatc | cgattaaaag | tcttgtggct | gtgtcctaat | 4680 |
| aggctctctt | tcaggacgtt | gtagtcaata | gagtggctga | accatacttg | agtttataaa | 4740 |
| gctcaaaaac | tgatgcaccc | actctgctat | tatcgtgtta | gtaagagttc | agctgtatat | 4800 |
| cattgtctag | gtttatcttg | tcctacagtg | ggtattcaaa | tatggccacc | agaggatatg | 4860 |
| tgtaaatata | agcacctgta | tttgcctgtt | gttgagaact | ggagggaaaa | caaaaaatgt | 4920 |
| ctggcaaccc | tttgcctttt | taaccgtaat | taattgacag | tttatttaga | gataagagtt | 4980 |
| ttcaaaaatc | tcttaactgc | cacaacccac | agagggtctt | gttttgccat | cttcagtggc | 5040 |
| tcacagatat | gatccaagtt | aacttgaaag | agatgagcag | tacccaggaa | attgtcctgc | 5100 |
| ctttaactct | ggctgtcctt | aattatgact | gtttaatgct | gaattttcca | tccgtctagt | 5160 |
| gtttgagggt | aaagaaaagc | ctttttttaaa | taagtatttc | tgtaaaacgg | catcggtggg | 5220 |
| atcttctgtg | ttgctatcac | gggtgaaaga | gggaaacatt | tcttattttt | attaagcaga | 5280 |
| gcattattta | cagaaagcca | ttgttgagaa | ttagttccca | catcatataa | atatccatta | 5340 |
| accattctaa | attgtaagag | aactccagtg | ttgctatgca | caaggaactc | tcctgggggc | 5400 |
| cttttttgc | atagcaatta | aaggtatgct | atttgtcagt | agccattttt | tgcagtgatt | 5460 |
| taaagaccaa | agttgtttta | cagctgtgtt | acccttaaag | gttttttttt | tatgtattaa | 5520 |
| atcaatttat | cactgtttga | agctttgaat | acctgcaatc | tttgccaaga | tacttttta | 5580 |
| tttaaaaaaa | taactgtgta | aatattaccc | tgtaatatta | tatatactta | ataaaacatt | 5640 |
| ttaagcta | | | | | 5648 |

<210> SEQ ID NO 6
<211> LENGTH: 331
<212> TYPE: PRT
<213> ORGANISM: Mus musculus

<400> SEQUENCE: 6

Met Trp Pro Leu Ala Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Thr Asp Gln Asn
65              70                  75                  80

Phe Thr Ser Ala Lys Ile Ser Val Ser Asp Leu Ile Asn Gly Ile Ala
            85                  90                  95

Ser Leu Lys Met Asp Lys Arg Asp Ala Met Val Gly Asn Tyr Thr Cys
        100                 105                 110

Glu Val Thr Glu Leu Ser Arg Glu Gly Lys Thr Val Ile Glu Leu Lys
    115                 120                 125

Asn Arg Thr Ala Phe Asn Thr Asp Gln Gly Ser Ala Cys Ser Tyr Glu
130             135                 140

Glu Lys Gly Gly Cys Lys Leu Val Ser Trp Phe Ser Pro Asn Glu
145                 150                 155                 160

Lys Ile Leu Ile Val Ile Phe Pro Ile Leu Ala Ile Leu Leu Phe Trp
            165                 170                 175

Gly Lys Phe Gly Ile Leu Thr Leu Lys Tyr Lys Ser Ser His Thr Asn
        180                 185                 190

Lys Arg Ile Ile Leu Leu Val Ala Gly Leu Val Leu Thr Val Ile
    195                 200                 205

Val Val Val Gly Ala Ile Leu Leu Ile Pro Gly Glu Lys Pro Val Lys
210             215                 220

Asn Ala Ser Gly Leu Gly Leu Ile Val Ile Ser Thr Gly Ile Leu Ile
225                 230                 235                 240

Leu Leu Gln Tyr Asn Val Phe Met Thr Ala Phe Gly Met Thr Ser Phe
            245                 250                 255

Thr Ile Ala Ile Leu Ile Thr Gln Val Leu Gly Tyr Val Leu Ala Leu
        260                 265                 270

Val Gly Leu Cys Leu Cys Ile Met Ala Cys Glu Pro Val His Gly Pro
    275                 280                 285

Leu Leu Ile Ser Gly Leu Gly Ile Ile Ala Leu Ala Glu Leu Leu Gly
290             295                 300

Leu Val Tyr Met Lys Phe Val Ala Ser Asn Gln Arg Thr Ile Gln Pro
305                 310                 315                 320

Pro Arg Lys Ala Val Glu Glu Pro Leu Asn Glu
            325                 330

<210> SEQ ID NO 7
<211> LENGTH: 5618
<212> TYPE: DNA
<213> ORGANISM: Mus musculus

<400> SEQUENCE: 7
gcctacaccg ggagagcagg gaggaggagt tggactgagg ttgggcggct ccgaggtcca    60
gggcgagctt ggccagaggg agtagagagc agcggggctg cgcagggacg cgtgccgtga   120
gttccggtga gcgtgtgtgt cccatgctcc cgtctttcag gccggcccag gacacgaagc   180
cggaagagag ctggctggag ggacgggggc cgtgagcaga gagtgcaacc cgcgcagccc   240

```
cggggacagg ctgattcttg gcgctctccg ccggagcctg cccagggctg ggtgtgaggc    300
tggcgtcacg tcaacgagca gaggcggcca ggcggggcgg agtgcgcgtg cgcggggcgg    360
cgagcacgcg cgcgcgcgca cccccgggca gcctgggcgg ccgctcctgc ctgtcactgc    420
tgcggcgctg ctggtcggtc gtttcccttg aaggcagcag cggaggcggc ggctgctcca    480
gacacctgcg gcggcgaccc cccggcggcg cggagatgtg gcccttggcg gcggcgctgt    540
tgctgggctc ctgctgctgc ggttcagctc aactactgtt tagtaacgtc aactccatag    600
agttcacttc atgcaatgaa actgtggtca tcccttgcat cgtccgtaat gtggaggcgc    660
aaagcaccga agaaatgttt gtgaagtgga agttgaacaa atcgtatatt ttcatctatg    720
atggaaataa aaatagcact actacagatc aaaactttac cagtgcaaaa atctcagtct    780
cagacttaat caatggcatt gcctctttga aaatggataa gcgcgatgcc atggtgggaa    840
actacacttg cgaagtgaca gagttatcca gagaaggcaa aacagttata gagctgaaaa    900
accgcacggt tcgtggtttt tctccaaatg aaaagatcct cattgttatt ttcccaattt    960
tggctatact cctgttctgg ggaaagtttg gtattttaac actcaaatat aaatccagcc   1020
atacgaataa gagaatcatt ctgctgctcg ttgccgggct ggtgctcaca gtcatcgtgg   1080
ttgttggagc catccttctc atcccaggag aaaagcccgt gaagaatgct tctggacttg   1140
gcctcattgt aatctctacg gggatattaa tactacttca gtacaatgtg tttatgacag   1200
cttttggaat gacctctttc accattgcca tattgatcac tcaagtgctg ggctacgtcc   1260
ttgctttggt cgggctgtgt ctctgcatca tggcatgtga gccagtgcac ggccccttt    1320 tgatttcagg tttggggatc atagctctag cagaactact tggattagtt tatatgaagt   1380
ttgtcgcttc caaccagagg actatccaac ctcctaggaa agctgtagag gaacccctta   1440
acgcatttaa agagtcaaaa ggaatgatga atgacgaata ggtgaaggga agtgacggac   1500
tgtaacttgg aagtcagaaa tggaagaata cagttgtcta agcaccaggt cttcacgact   1560
cacagctgga aggaacagac aacagtaact gacttccatc caggaaaaca tgtcacataa   1620
atgattacta agtttatatt caaagcagct gtacttaca taataaaaa aatatgatgt   1680 gctgtgtaac caattggaat cccattttc tattgtttct actcaactag gggcaaacgt   1740
ttcaggggca acttccaaga atgatgcttg ttagatccta gagtctctga acactgagtt   1800
taaattgatt ccgagtgaga ctcgccaagc actaacctga gggttagtta cccagagata   1860
cctatgaaaa acagtggtat ccagcaagcc ttagtaaact caggttgcca gcagctttgc   1920
cacttccgct gctagctgaa taacaagact gccacttctg ggtcatagtg atagagactg   1980
aagtagaaaa acgaatgtgg ttgggcaaat cccgtgtggc ccctctgtgt gctatgatat   2040
tgatggcact ggtgtcttca ttcttggggg ttgccatcat tcacacacac ccctttgaca   2100
tacagtgcac cccagttttg aatacatttt ttttgcaccc tgtcccgttc tgctactttg   2160
atttgcgtta tgatatatat atatatatat aataccttt tcctctctta aacatggtcc   2220
tgtgacacaa tagtcagttg cagaaaggag ccagacttat tcgcaaagca ctgtgctcaa   2280
actcttcaga aaaaaggaa aaaaaaaaa agctatagtt gtaacatatg tattccagac   2340
ctctggttta aaggcaaaag aaaaaaaatc tacagtgttt cttctcatgt tttctgatcg   2400
gaggcatgac aaagcaagac tgaaatctga actgtgtctc ctgcatggca acacgtgtct   2460
ccgtcaggcc ctcgcaaggc ccggggaggg ggttctacgc ctcttgtctc tttgttgcat   2520
gctgaacact catcgccttc ctactgtatc ctgcctcctg cagcctccct cttcctcctc   2580
```

```
ctcttcctct tcctcctctt cctcctcctc ctcctcttcc tccaagtttg aaaggtcaaa    2640
caaaactacc acattcccta cccagttaga agaaaaccac cgtcctgaca gttgtgatcg    2700
catggagtac ttttagatta ttagcacctg tttttacctc gtttgtgggc gtgtttgtat    2760
gtgcacatgt atgaagtcgg cacatgcacc ttctgtatgg gcagaggcgt ggcatctaca    2820
gaagagcaga tgccaacttt gtgcttttag tgaatacatt aaaaaaaaaa aaccaacggt    2880
ccttattgag tggaattcta tttgatgcaa atatttgagc tctttaagac tttaaaacta    2940
gataatgtgc caagctttta ggactgctca ccagtgccct ctgaagaaac accagtactt    3000
tttcctgttt gtgtaataaa ggcatatttg tatttgtgtt tgcatcacta atggttattt    3060
cttcttagtc cactgaatgt ttccatgtgc ctctcgtatg ccaaacttttt tgtcatcttt    3120 catgtgggga ccaaatggtt tgtctgtggc aaacctaaac ctatgacctg ctgaggcctc    3180
tcagaaaact gaccacagta ccaagatagt acttcgcaaa gaaaagtagg ttccctccct    3240
ggttttgtag ctgtcgccaa tattagcgta attccaagga gctgaacgcc tttatataaa    3300
tctgatggca ccctgatgctt ttagttctga aaatatttac actcggatca tgttgttgat    3360
gacttaaaca aagttttgat gaagagagca aaaaaaaagc aggtggattt ggaacagttt    3420
cagggttttt tttgtttttt gtttttgtt tttgtttttt tttttttatt tttgttttc     3480 tgttctctgt tagaaaagtc aggtgttctc tgtcaggcta tctttatagt caatttttt    3540 tacgaactaa agtagtacct tttaatatgt agtcaacgcc cctctgctcg gggttcagtt    3600
ttgggtctta accagctgtc atgttctcta tgctgcctgc cacttgaggc actgagtgcc    3660
ctagacagtc ccatcggtgg tagccaggga aacgaaagac gaactcaact cttgctccta    3720
ataatcaact ctctgtatga aggatggcag cattaagagt cctcctgcct gggcattatt    3780
gggccagttc accctcttta aatcaaaccc gcagtggctc ccagttctcg tcccatcaga    3840
tttaaattgc taacagtatg gggggcacca cgcatctgtt ttgtcccaca atgcgctttt    3900
ctctcccaaa tcccgatttc tgctgtcata gcctctattc aatttttatt tattgtctgc    3960
cctccactta tacaatcgta gagagcaatg ccatttgtca cttctgcaa cagtttttg     4020 agcctttatg gctgaatccc atttttcttc tctttcaaac tgtttgctcc attgctcctc    4080
ccgcacggct gtccgtacag tcatcccatc catctggggg cctcttttcat ctctcaccct    4140 tcctggtgct tcgtggatct ctgcttacct ctgtgggttt tttttttttt tttttgactta    4200 ttcttctcac tggactttaa gattacttcc acagcgaaag tgctgcctcc cttttctgcc    4260
cgcagtgttc tgcgtacttt agatactact cagtgctgac atttgatggc aaaagttgcc    4320
tgcacttaaa tttctctttt taatagggtg aactagagtt ggagttttt tctcttttt     4380 ctcttttctc tctctctctc tctctctctc tctctctctc tctctctctc cctccctccc    4440
tccctccctc cctccctccc tctctctctc ttttttcttc tttcttttctt tctttcttc    4500 tttcttcctt tctttcttc tttcttttt tgacaaatct cacaggcttt gagaattata    4560
aaaggtgaca gttcacctga aaatcacagg tctggtctgt ttaaattgtt gagaaatatc    4620
cgattaaaag tcttgtggct gtgtcctaat aggctctctt tcaggacgtt gtagtcaata    4680
gagtggctga accatacttg agtttataaa gctcaaaaac tgatgcaccc actctgctat    4740
tatcgtgtta gtaagagttc agctgtatat cattgtctag gtttatcttg tcctacagtg    4800
ggtattcaaa tatggccacc agaggatatg tgtaaatata agcacctgta tttgcctgtt    4860
gttgagaact ggagggaaaa caaaaaatgt ctggcaaccc tttgccttt taaccgtaat    4920 taattgacag tttatttaga gataagagtt ttcaaaaatc tcttaactgc cacaacccac    4980
```

```
agagggtctt gtttttgccat cttcagtggc tcacagatat gatccaagtt aacttgaaag    5040
agatgagcag tacccaggaa attgtcctgc ctttaactct ggctgtcctt aattatgact    5100
gtttaatgct gaattttcca tccgtctagt gtttgagggt aaagaaaagc cttttttaaa    5160
taagtatttc tgtaaaacgg catcggtggg atcttctgtg ttgctatcac gggtgaaaga    5220
gggaaacatt tcttattttt attaagcaga gcattattta cagaaagcca ttgttgagaa    5280
ttagttccca catcatataa atatccatta accattctaa attgtaagag aactccagtg    5340
ttgctatgca caaggaactc tcctgggggc cttttttgc atagcaatta aaggtatgct    5400
atttgtcagt agccattttt tgcagtgatt taaagaccaa agttgtttta cagctgtgtt    5460
acccttaaag gttttttttt tatgtattaa atcaatttat cactgtttga agctttgaat    5520
acctgcaatc tttgccaaga tacttttta tttaaaaaaa taactgtgta aatattaccc    5580
tgtaatatta tatatactta ataaaacatt ttaagcta                            5618
```

<210> SEQ ID NO 8
<211> LENGTH: 321
<212> TYPE: PRT
<213> ORGANISM: Mus musculus

<400> SEQUENCE: 8

```
Met Trp Pro Leu Ala Ala Leu Leu Leu Gly Ser Cys Cys Cys Gly
 1               5                  10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Val Ser Trp Phe Ser Pro Asn Glu Lys Ile Leu Ile Val
    130                 135                 140

Ile Phe Pro Ile Leu Ala Ile Leu Leu Phe Trp Gly Lys Phe Gly Ile
145                 150                 155                 160

Leu Thr Leu Lys Tyr Lys Ser Ser His Thr Asn Lys Arg Ile Ile Leu
                165                 170                 175

Leu Leu Val Ala Gly Leu Val Leu Thr Val Ile Val Val Gly Ala
            180                 185                 190

Ile Leu Leu Ile Pro Gly Glu Lys Pro Val Lys Asn Ala Ser Gly Leu
        195                 200                 205

Gly Leu Ile Val Ile Ser Thr Gly Ile Leu Ile Leu Gln Tyr Asn
    210                 215                 220

Val Phe Met Thr Ala Phe Gly Met Thr Ser Phe Thr Ile Ala Ile Leu
225                 230                 235                 240

Ile Thr Gln Val Leu Gly Tyr Val Leu Ala Leu Val Gly Leu Cys Leu
                245                 250                 255
```

Cys Ile Met Ala Cys Glu Pro Val His Gly Pro Leu Leu Ile Ser Gly
            260                 265                 270

Leu Gly Ile Ile Ala Leu Ala Glu Leu Leu Gly Leu Val Tyr Met Lys
        275                 280                 285

Phe Val Ala Ser Asn Gln Arg Thr Ile Gln Pro Pro Arg Lys Ala Val
        290                 295                 300

Glu Glu Pro Leu Asn Ala Phe Lys Glu Ser Lys Gly Met Met Asn Asp
305                 310                 315                 320

Glu

<210> SEQ ID NO 9
<211> LENGTH: 5021
<212> TYPE: DNA
<213> ORGANISM: Homo sapiens

<400> SEQUENCE: 9

| | | | | | | |
|---|---|---|---|---|---|---|
| agtgggagcg | cgcgtgcgcg | cggccgtgca | gcctgggcag | tgggtcctgc | ctgtgacgcg | 60 |
| cggcggcggt | cggtcctgcc | tgtaacggcg | gcggcggctg | ctgctccgga | cacctgcggc | 120 |
| ggcggcggcg | accccgcggc | gggcgcggag | atgtggcccc | tggtagcggc | gctgttgctg | 180 |
| ggctcggcgt | gctgcggatc | agctcagcta | ctatttaata | aaacaaaatc | tgtagaattc | 240 |
| acgttttgta | atgacactgt | cgtcattcca | tgctttgtta | ctaatatgga | ggcacaaaac | 300 |
| actactgaag | tatacgtaaa | gtggaaattt | aaaggaagag | atatttacac | ctttgatgga | 360 |
| gctctaaaca | gtccactgt | ccccactgac | tttagtagtg | caaaaattga | agtctcacaa | 420 |
| ttactaaaag | gagatgcctc | tttgaagatg | gataagagtg | atgctgtctc | acacacagga | 480 |
| aactacactt | gtgaagtaac | agaattaacc | agagaaggtg | aaacgatcat | cgagctaaaa | 540 |
| tatcgtgttg | tttcatggtt | ttctccaaat | gaaaatattc | ttattgttat | tttcccaatt | 600 |
| tttgctatac | tcctgttctg | gggacagttt | ggtattaaaa | cacttaaata | tagatccggt | 660 |
| ggtatggatg | agaaaacaat | tgctttactt | gttgctggac | tagtgatcac | tgtcattgtc | 720 |
| attgttggag | ccattctttt | cgtcccaggt | gaatattcat | taagaatgc | tactggcctt | 780 |
| ggtttaattg | tgacttctac | agggatatta | atattacttc | actactatgt | gtttagtaca | 840 |
| gcgattggat | taacctcctt | cgtcattgcc | atattggtta | ttcaggtgat | agcctatatc | 900 |
| ctcgctgtgg | ttggactgag | tctctgtatt | gcggcgtgta | taccaatgca | tggccctctt | 960 |
| ctgatttcag | gtttgagtat | cttagctcta | gcacaattac | ttggactagt | ttatatgaaa | 1020 |
| tttgtggaat | aactgaagtg | aagtgatgga | ctccgatttg | gagagtagta | agacgtgaaa | 1080 |
| ggaatacact | tgtgtttaag | caccatggcc | ttgatgattc | actgttgggg | agaagaaaca | 1140 |
| agaaaagtaa | ctggttgtca | cctatgagac | ccttacgtga | ttgttagtta | agttttatt | 1200 |
| caaagcagct | gtaatttagt | taataaaata | attatgatct | atgttgtttg | cccaattgag | 1260 |
| atccagtttt | ttgttgttat | ttttaatcaa | ttagggcaa | tagtagaatg | gacaatttcc | 1320 |
| aagaatgatg | cctttcaggt | cctagggcct | ctggcctcta | ggtaaccagt | ttaaattggt | 1380 |
| tcagggtgat | aactacttag | cactgccctg | gtgattaccc | agagatatct | atgaaaacca | 1440 |
| gtggcttcca | tcaaaccttt | gccaactcag | gttcacagca | gctttgggca | gttatggcag | 1500 |
| tatggcatta | gctgagaggt | gtctgccact | tctgggtcaa | tggaataata | aattaagtac | 1560 |
| aggcaggaat | ttggttggga | gcatcttgta | tgatctccgt | atgatgtgat | attgatggag | 1620 |
| atagtggtcc | tcattcttgg | gggttgccat | tcccacattc | ccccttcaac | aaacagtgta | 1680 |
| acaggtcctt | cccagattta | gggtactttt | attgatggat | atgttttcct | tttattcaca | 1740 |

```
taaccccttg aaaccctgtc ttgtcctcct gttacttgct tctgctgtac aagatgtagc    1800
accttttctc ctctttgaac atggtctagt gacacggtag caccagttgc aggaaggagc    1860
cagacttgtt ctcagagcac tgtgttcaca cttttcagca aaaatagcta tggttgtaac    1920
atatgtattc ccttcctctg atttgaaggc aaaaatctac agtgtttctt cacttctttt    1980
ctgatctggg gcatgaaaaa agcaagattg aaatttgaac tatgagtctc ctgcatggca    2040
acaaaatgtg tgtcaccatc aggccaacag gccagccctt gaatgggat ttattactgt      2100 tgtatctatg ttgcatgata acattcatc accttcctcc tgtagtcctg cctcgtactc     2160
cccttcccct atgattgaaa agtaaacaaa acccacattt cctatcctgg ttagaagaaa    2220
attaatgttc tgacagttgt gatcgcctgg agtactttta acttttagc attcgttttt     2280 tacctgtttg tggatgtgtg tttgtatgtg catacgtatg agataggcac atgcatcttc    2340
tgtatggaca aaggtggggt acctacagga gagcaaaggt taattttgtg cttttagtaa    2400
aaacatttaa atacaaagtt ctttattggg tggaattata tttgatgcaa atatttgatc    2460
acttaaaact tttaaaactt ctaggtaatt tgccacgctt tttgactgct caccaatacc    2520
ctgtaaaaat acgtaattct tcctgttgt gtaataagat attcatattt gtagttgcat      2580
taataatagt tatttcttag tccatcagat gttcccgtgt gcctcttta tgccaaattg      2640 attgtcatat ttcatgttgg gaccaagtag tttgcccatg gcaaacctaa atttatgacc    2700
tgctgaggcc tctcagaaaa ctgagcatac tagcaagaca gctcttcttg aaaaaaaaaa    2760
tatgtataca caaatatata cgtatatcta tatatacgta tgtatataca cacatgtata    2820
ttcttccttg attgtgtagc tgtccaaaat aataacatat atagagggag ctgtattcct    2880
ttatacaaat ctgatggctc ctgcagcact ttttccttct gaaatatttt acattttgct    2940
aacctagttt gttactttaa aaatcagttt tgatgaaagg agggaaaagc agatggactt    3000
gaaaaagatc caagctccta ttagaaaagg tatgaaaatc tttatagtaa aattttttat    3060
aaactaaagt tgtacctttt aatatgtagt aaactctcat ttatttgggg ttcgctcttg    3120
gatctcatcc atccattgtg ttctctttaa tgctgcctgc cttttgaggc attcactgcc    3180
ctagacaatg ccaccagaga tagtggggga aatgccagat gaaaccaact cttgctctca    3240
ctagttgtca gcttctctgg ataagtgacc acagaagcag gagtcctcct gcttgggcat    3300
cattgggcca gttccttctc tttaaatcag atttgtaatg gctcccaaat tccatcacat    3360
cacatttaaa ttgcagacag tgttttgcac atcatgtatc tgttttgtcc cataatatgc    3420
tttttactcc ctgatcccag tttctgctgt tgactcttcc attcagtttt atttattgtg    3480
tgttctcaca gtgacaccat ttgtcctttt ctgcaacaac cttccagct acttttgcca       3540 aattctattt gtcttctcct tcaaaacatt tccctttgca gttcctcttc atctgtgtag    3600
ctgctctttt gtctcttaac ttaccattcc tatagtactt tatgcatctc tgcttagttc    3660
tattagtttt ttggccttgc tcttctcctt gattttaaaa ttccttctat agctagagct    3720
tttctttctt tcattctctc ttcctgcagt gttttgcata catcagaagc taggtacata    3780
agttaaatga ttgagagttg gctgtattta gatttatcac tttttaatag ggtgagcttg    3840
agagttttct ttctttctgt ttttttttt tgtttttttt tttttttttt tttttttttt      3900
ttttgactaa tttcacatgc tctaaaaacc ttcaaggtg attattttc tcctggaaac       3960 tccaggtcca ttctgtttaa atccctaaga atgtcagaat taaaataaca gggctatccc    4020
gtaattggaa atatttcttt tttcaggatg ctatagtcaa tttagtaagt gaccaccaaa    4080
```

```
ttgttatttg cactaacaaa gctcaaaaca cgataagttt actcctccat ctcagtaata    4140
aaaattaagc tgtaatcaac cttctaggtt tctcttgtct taaaatgggt attcaaaaat    4200
ggggatctgt ggtgtatgta tggaaacaca tactccttaa tttacctgtt gttggaaact    4260
ggagaaatga ttgtcgggca accgttattt ttttattgta tttttatttgg ttgagggatt    4320
tttttataaa cagtttttact tgtgtcatat tttaaaatta ctaactgcca tcacctgctg    4380
gggtcctttg ttaggtcatt ttcagtgact aatagggata atccaggtaa ctttgaagag    4440
atgagcagtg agtgaccagg cagttttttct gcctttagct ttgacagttc ttaattaaga    4500
tcattgaaga ccagctttct cataaatttc tcttttttgaa aaaagaaag catttgtact    4560
aagctcctct gtaagacaac atcttaaatc ttaaaagtgt tgttatcatg actggtgaga    4620
gaagaaaaca ttttgttttt attaaatgga gcattattta caaaaagcca ttgttgagaa    4680
ttagatccca catcgtataa atatctatta accattctaa ataaagagaa ctccagtgtt    4740
gctatgtgca agatcctctc ttggagcttt tttgcatagc aattaaaggt gtgctatttg    4800
tcagtagcca ttttttttgca gtgatttgaa gaccaaagtt gttttacagc tgtgttaccg    4860
ttaaaggttt ttttttttat atgtattaaa tcaattatc actgtttaaa gctttgaata    4920
tctgcaatct ttgccaaggt actttttat ttaaaaaaaa ataaactttt gtaaatatta    4980
ccctgtaata ttatatatac ttaataaaac attttaagct a                        5021
```

<210> SEQ ID NO 10
<211> LENGTH: 293
<212> TYPE: PRT
<213> ORGANISM: Homo sapiens

<400> SEQUENCE: 10

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
        130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

```
Gly Leu Gly Leu Ile Val Thr Ser Thr Gly Ile Leu Ile Leu Leu His
    210                 215                 220
Tyr Tyr Val Phe Ser Thr Ala Ile Gly Leu Thr Ser Phe Val Ile Ala
225                 230                 235                 240
Ile Leu Val Ile Gln Val Ile Ala Tyr Ile Leu Ala Val Val Gly Leu
                245                 250                 255
Ser Leu Cys Ile Ala Ala Cys Ile Pro Met His Gly Pro Leu Leu Ile
            260                 265                 270
Ser Gly Leu Ser Ile Leu Ala Leu Ala Gln Leu Leu Gly Leu Val Tyr
        275                 280                 285
Met Lys Phe Val Glu
    290

<210> SEQ ID NO 11
<211> LENGTH: 5288
<212> TYPE: DNA
<213> ORGANISM: Homo sapiens

<400> SEQUENCE: 11
```

| | | | | | |
|---|---|---|---|---|---|
| ggggagcagg | cggggagcg | ggcgggaagc | agtgggagcg | cgcgtgcgcg | cggccgtgca | 60 |
| gcctgggcag | tgggtcctgc | ctgtgacgcg | cggcggcggt | cggtcctgcc | tgtaacggcg | 120 |
| gcggcggctg | ctgctccaga | cacctgcggc | ggcggcggcg | accccgcggc | gggcgcggag | 180 |
| atgtggcccc | tggtagcggc | gctgttgctg | ggctcggcgt | gctgcggatc | agctcagcta | 240 |
| ctatttaata | aaacaaaatc | tgtagaattc | acgttttgta | atgacactgt | cgtcattcca | 300 |
| tgctttgtta | ctaatatgga | ggcacaaaac | actactgaag | tatacgtaaa | gtggaaattt | 360 |
| aaaggaagag | atatttacac | ctttgatgga | gctctaaaca | gtccactgtg | ccccactgac | 420 |
| tttagtagtg | caaaaattga | agtctcacaa | ttactaaaag | gagatgcctc | tttgaagatg | 480 |
| gataagagtg | atgctgtctc | acacacagga | aactacactt | gtgaagtaac | agaattaacc | 540 |
| agagaaggtg | aaacgatcat | cgagctaaaa | tatcgtgttg | tttcatggtt | ttctccaaat | 600 |
| gaaaatattc | ttattgttat | tttcccaatt | tttgctatac | tcctgttctg | gggacagttt | 660 |
| ggtattaaaa | cacttaaata | tagatccggt | ggtatggatg | agaaaacaat | tgctttactt | 720 |
| gttgctggac | tagtgatcac | tgtcattgtc | attgttggag | ccattctttt | cgtcccaggt | 780 |
| gaatattcat | aaagaatgc | tactggcctt | ggtttaattg | tgacttctac | agggatatta | 840 |
| atattacttc | actactatgt | gtttagtaca | gcgattggat | taacctcctt | cgtcattgcc | 900 |
| atattggtta | ttcaggtgat | agcctatatc | ctcgctgtgg | ttggactgag | tctctgtatt | 960 |
| gcggcgtgta | taccaatgca | tggccctctt | ctgatttcag | gtttgagtat | cttagctcta | 1020 |
| gcacaattac | ttggactagt | ttatatgaaa | tttgtggctt | ccaatcagaa | gactatacaa | 1080 |
| cctcctagga | ataactgaag | tgaagtgatg | gactccgatt | tggagagtag | taagacgtga | 1140 |
| aaggaataca | cttgtgttta | agcaccatgg | ccttgatgat | tcactgttgg | ggagaagaaa | 1200 |
| caagaaaagt | aactggttgt | cacctatgag | acccttacgt | gattgttagt | taagttttta | 1260 |
| ttcaaagcag | ctgtaattta | gttaataaaa | taattatgat | ctatgttgtt | tgcccaattg | 1320 |
| agatccagtt | ttttgttgtt | attttttaatc | aattagggc | aatagtagaa | tggacaattt | 1380 |
| ccaagaatga | tgcctttcag | gtcctagggc | ctctggcctc | taggtaacca | gtttaaattg | 1440 |
| gttcagggtg | ataactactt | agcactgccc | tggtgattac | ccagagatat | ctatgaaaac | 1500 |
| cagtggcttc | catcaaacct | tgccaactc | aggttcacag | cagctttggg | cagttatggc | 1560 |
| agtatggcat | tagctgagag | gtgtctgcca | cttctgggtc | aatggaataa | taaattaagt | 1620 |

-continued

```
acaggcagga atttggttgg gagcatcttg tatgatctcc gtatgatgtg atattgatgg    1680
agatagtggt cctcattctt gggggttgcc attcccacat tcccccttca acaaacagtg    1740
taacaggtcc ttcccagatt tagggtactt ttattgatgg atatgttttc cttttattca    1800
cataacccct tgaaaccctg tcttgtcctc ctgttacttg cttctgctgt acaagatgta    1860
gcaccttttc tcctctttga acatggtcta gtgacacggt agcaccagtt gcaggaagga    1920
gccagacttg ttctcagagc actgtgttca cacttttcag caaaaatagc tatggttgta    1980
acatatgtat tcccttcctc tgatttgaag gcaaaaatct acagtgtttc ttcacttctt    2040
ttctgatctg gggcatgaaa aaagcaagat tgaaatttga actatgagtc tcctgcatgg    2100
caacaaaatg tgtgtcacca tcaggccaac aggccagccc ttgaatgggg atttattact    2160
gttgtatcta tgttgcatga taaacattca tcaccttcct cctgtagtcc tgcctcgtac    2220 tcccctthccc ctatgattga aaagtaaaca aaacccacat ttcctatcct ggttagaaga    2280
aaattaatgt tctgacagtt gtgatcgcct ggagtacttt tagacttta gcattcgttt      2340 tttacctgtt tgtggatgtg tgtttgtatg tgcatacgta tgagataggc acatgcatct    2400
tctgtatgga caaaggtggg gtacctacag gagagcaaag gttaattttg tgcttttagt    2460
aaaaacattt aaatacaaag ttcttattg ggtggaatta tatttgatgc aaatatttga    2520
tcacttaaaa cttttaaaac ttctaggtaa tttgccacgc tttttgactg ctcaccaata    2580
ccctgtaaaa atacgtaatt cttcctgttt gtgtaataag atattcatat ttgtagttgc    2640
attaataata gttatttctt agtccatcag atgttcccgt gtgcctcttt tatgccaaat    2700
tgattgtcat atttcatgtt gggaccaagt agtttgccca tggcaaacct aaatttatga    2760
cctgctgagg cctctcagaa aactgagcat actagcaaga cagctcttct tgaaaaaaaa    2820
aatatgtata cacaaatata tacgtatatc tatatatacg tatgtatata cacacatgta    2880
tattcttcct tgattgtgta gctgtccaaa ataataacat atatagaggg agctgtattc    2940
ctttatacaa atctgatggc tcctgcagca cttttttcctt ctgaaaatat ttacattttg    3000
ctaacctagt ttgttacttt aaaaatcagt tttgatgaaa ggagggaaaa gcagatggac    3060
ttgaaaaaga tccaagctcc tattagaaaa ggtatgaaaa tctttatagt aaaatttttt    3120
ataaactaaa gttgtacctt ttaatatgta gtaaactctc atttatttgg ggttcgctct    3180
tggatctcat ccatccattg tgttctcttt aatgctgcct gccttttgag gcattcactg    3240
ccctagacaa tgccaccaga gatagtgggg gaaatgccag atgaaaccaa ctcttgctct    3300
cactagttgt cagcttctct ggataagtga ccacagaagc aggagtcctc ctgcttgggc    3360
atcattgggc cagttccttc tctttaaatc agatttgtaa tggctcccaa attccatcac    3420
atcacattta aattgcagac agtgttttgc acatcatgta tctgttttgt cccataatat    3480 gcttttact ccctgatccc agtttctgct gttgactctt ccattcagtt ttatttattg    3540
tgtgttctca cagtgacacc atttgtcctt ttctgcaaca accttccag ctactttgc    3600 caaattctat ttgtcttctc cttcaaaaca ttctcctttg cagttcctct tcatctgtgt    3660
agctgctctt ttgtctctta acttaccatt cctatagtac tttatgcatc tctgcttagt    3720
tctattagtt ttttggcctt gctcttctcc ttgattttaa aattccttct atagctagag    3780
ctttttcttc tttcattctc tcttcctgca gtgttttgca tacatcagaa gctaggtaca    3840
taagttaaat gattgagagt tggctgtatt tagatttatc acttttttaat aggggtgagct    3900 tgagagtttt cttttctttct gttttttttt tttgtttttt tttttttttt tttttttttt    3960
```

-continued

```
ttttttgact aatttcacat gctctaaaaa ccttcaaagg tgattatttt tctcctggaa    4020
actccaggtc cattctgttt aaatccctaa gaatgtcaga attaaaataa cagggctatc    4080
ccgtaattgg aaatatttct tttttcagga tgctatagtc aatttagtaa gtgaccacca    4140
aattgttatt tgcactaaca aagctcaaaa cacgataagt ttactcctcc atctcagtaa    4200
taaaaattaa gctgtaatca accttctagg tttctcttgt cttaaaatgg gtattcaaaa    4260
atggggatct gtggtgtatg tatggaaaca catactcctt aatttacctg ttgttggaaa    4320
ctggagaaat gattgtcggg caaccgttta ttttttattg tattttatt ggttgaggga     4380 tttttttata aacagtttta cttgtgtcat attttaaaat tactaactgc catcacctgc    4440
tggggtcctt tgttaggtca ttttcagtga ctaatagggga taatccaggt aactttgaag   4500
agatgagcag tgagtgacca ggcagttttt ctgcctttag ctttgacagt tcttaattaa    4560
gatcattgaa gaccagcttt ctcataaatt tctcttttg aaaaaagaa agcatttgta      4620 ctaagctcct ctgtaagaca acatcttaaa tcttaaaagt gttgttatca tgactggtga    4680
gagaagaaaa catttttgttt ttattaaatg gagcattatt tacaaaaagc cattgttgag   4740
aattagatcc cacatcgtat aaatatctat taaccattct aaataaagag aactccagtg    4800
ttgctatgtg caagatcctc tcttggagct tttttgcata gcaattaaag gtgtgctatt    4860
tgtcagtagc catttttttg cagtgatttg aagaccaaag ttgttttaca gctgtgttac    4920
cgttaaaggt ttttttttttt atatgtatta aatcaattta tcactgttta aagctttgaa   4980
tatctgcaat ctttgccaag gtactttttt atttaaaaaa aaacataact ttgtaaatat    5040
taccctgtaa tattatatat acttaataaa acatttaag ctattttgtt gggctatttc     5100
tattgctgct acagcagacc acaagcacat ttctgaaaaa tttaatttat taatgtatt     5160 ttaagttgct tatattctag gtaacaatgt aaagaatgat ttaaaatatt aattatgaat    5220
tttttgagta aatacccaa taagcttttta attagagcag agtttaatt aaaagttttta    5280 aatcagtc                                                             5288
```

<210> SEQ ID NO 12
<211> LENGTH: 305
<212> TYPE: PRT
<213> ORGANISM: Homo sapiens

<400> SEQUENCE: 12

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
```

```
                130             135             140
Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
                195                 200                 205

Gly Leu Gly Leu Ile Val Thr Ser Thr Gly Ile Leu Ile Leu Leu His
                210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
                275                 280                 285

Met Lys Phe Val Ala Ser Asn Gln Lys Thr Ile Gln Pro Pro Arg Asn
290                 295                 300

Asn
305

<210> SEQ ID NO 13
<211> LENGTH: 5078
<212> TYPE: DNA
<213> ORGANISM: Homo sapiens

<400> SEQUENCE: 13
agtgggagcg cgcgtgcgcg cggccgtgca gcctgggcag tgggtcctgc ctgtgacgcg        60
cggcggcggt cggtcctgcc tgtaacggcg gcggcggctg ctgctccgga cacctgcggc       120
ggcggcggcg accccgcggc gggcgcggag atgtggcccc tggtagcggc gctgttgctg       180
ggctcggcgt gctgcggatc agctcagcta ctatttaata aaacaaaatc tgtagaattc       240
acgttttgta atgacactgt cgtcattcca tgctttgtta ctaatatgga ggcacaaaac       300
actactgaag tatacgtaaa gtggaaattt aaaggaagag atatttacac ctttgatgga       360
gctctaaaca gtccactgtc cccactgac tttagtagtg caaaaattga agtctcacaa       420
ttactaaaag gagatgcctc tttgaagatg gataagagtc atgctgtctc acacacagga       480
aactacactt gtgaagtaac agaattaacc agagaaggtg aaacgatcat cgagctaaaa       540
tatcgtgttg tttcatggtt ttctccaaat gaaatattc ttattgttat tttcccaatt       600
tttgctatac tcctgttctg gggacagttt ggtattaaaa cacttaaata tagatccggt       660
ggtatggatg agaaaacaat tgctttactt gttgctggac tagtgatcac tgtcattgtc       720
attgttggag ccattctttt cgtcccaggt gaatattcat taagaatgc tactggcctt       780 ggtttaattg tgacttctac agggatatta atattacttc actactatgt gtttagtaca       840
gcgattggat taacctcctt cgtcattgcc atattggtta tcaggtgat agcctatatc       900 ctcgctgtgg ttggactgag tctctgtatt gcggcgtgta taccaatgca tggccctctt       960
ctgatttcag gttgagtat cttagctcta gcacaattac ttggactagt ttatatgaaa      1020
tttgtggctt ccaatcagaa gactatacaa cctcctagga agctgtaga ggaaccccctt      1080
```

```
aatgaataac tgaagtgaag tgatggactc cgatttggag agtagtaaga cgtgaaagga   1140
atacacttgt gtttaagcac catggccttg atgattcact gttggggaga agaaacaaga   1200
aaagtaactg gttgtcacct atgagaccct tacgtgattg ttagttaagt ttttattcaa   1260
agcagctgta atttagttaa taaaataatt atgatctatg ttgtttgccc aattgagatc   1320
cagttttttg ttgttatttt taatcaatta ggggcaatag tagaatggac aatttccaag   1380
aatgatgcct ttcaggtcct agggcctctg gcctctaggt aaccagttta aattggttca   1440
gggtgataac tacttagcac tgccctggtg attacccaga gatatctatg aaaaccagtg   1500
gcttccatca aacctttgcc aactcaggtt cacagcagct ttgggcagtt atggcagtat   1560
ggcattagct gagaggtgtc tgccacttct gggtcaatgg aataataaat taagtacagg   1620
caggaatttg gttgggagca tcttgtatga tctccgtatg atgtgatatt gatggagata   1680
gtggtcctca ttcttggggg ttgccattcc cacattcccc cttcaacaaa cagtgtaaca   1740
ggtccttccc agatttaggg tacttttatt gatggatatg ttttccttt attcacataa    1800 cccccttgaaa ccctgtcttg tcctcctgtt acttgcttct gctgtacaag atgtagcacc   1860
ttttctcctc tttgaacatg gtctagtgac acggtagcac cagttgcagg aaggagccag   1920
acttgttctc agagcactgt gttcacactt ttcagcaaaa atagctatgg ttgtaacata   1980
tgtattccct tcctctgatt tgaaggcaaa aatctacagt gtttcttcac ttctttttctg   2040 atctggggca tgaaaaaagc aagattgaaa tttgaactat gagtctcctg catggcaaca   2100
aaatgtgtgt caccatcagg ccaacaggcc agcccttgaa tggggattta ttactgttgt   2160
atctatgttg catgataaac attcatcacc ttcctcctgt agtcctgcct cgtactcccc    2220
ttcccctatg attgaaaagt aaacaaaacc cacatttcct atcctggtta agagaaaatt   2280
aatgttctga cagttgtgat cgcctggagt acttttagac ttttagcatt cgttttttac   2340
ctgtttgtgg atgtgtgttt gtatgtgcat acgtatgaga taggcacatg catcttctgt   2400
atggacaaag gtggggtacc tacaggagag caaaggttaa ttttgtgctt ttagtaaaaa   2460
catttaaata caaagttctt tattgggtgg aattatattt gatgcaaata tttgatcact   2520
taaaactttt aaaacttcta ggtaatttgc cacgcttttt gactgctcac caatacccct   2580
taaaaatacg taattcttcc tgtttgtgta ataagatatt catatttgta gttgcattaa   2640
taatagttat ttcttagtcc atcagatgtt cccgtgtgcc tcttttatgc caaattgatt   2700
gtcatatttc atgttgggac caagtagttt gcccatggca aacctaaatt tatgacctgc   2760
tgaggcctct cagaaaactg agcatactag caagacagct cttcttgaaa aaaaaaatat   2820
gtatacacaa atatatacgt atatctatat atacgtatgt atatacacac atgtatattc   2880
ttccttgatt gtgtagctgt ccaaaataat aacatatata gagggagctg tattcctta    2940 tacaaatctg atggctcctg cagcactttt tccttctgaa atatttaca ttttgctaac    3000 ctagtttgtt acttttaaaa tcagttttga tgaaaggagg gaaaagcaga tggacttgaa   3060
aaagatccaa gctcctatta gaaaaggtat gaaaatcttt atagtaaaat tttttataaa   3120
ctaaagttgt accttttaat atgtagtaaa ctctcattta tttggggttc gctcttggat   3180
ctcatccatc cattgtgttc tctttaatgc tgcctgcctt tgaggcatt cactgcccta    3240 gacaatgcca ccagagatag tgggggaaat gccagatgaa accaactctt gctctcacta   3300
gttgtcagct tctctggata agtgaccaca gaagcaggag tcctcctgct tgggcatcat   3360
tgggccagtt ccttctcttt aaatcagatt tgtaatggc cccaaattcc atcacatcac    3420
atttaaattg cagacagtgt tttgcacatc atgtatctgt tttgtcccat aatatgcttt    3480
```

-continued

```
ttactccctg atcccagttt ctgctgttga ctcttccatt cagttttatt tattgtgtgt   3540
tctcacagtg acaccatttg tccttttctg caacaacctt tccagctact tttgccaaat   3600
tctatttgtc ttctccttca aaacattctc ctttgcagtt cctcttcatc tgtgtagctg   3660
ctcttttgtc tcttaactta ccattcctat agtactttat gcatctctgc ttagttctat   3720
tagtttttttg gccttgctct ctccttgat tttaaaattc cttctatagc tagagctttt   3780
ctttctttca ttctctcttc ctgcagtgtt ttgcatacat cagaagctag gtacataagt   3840
taaatgattg agagttggct gtatttagat ttatcacttt ttaatagggt gagcttgaga   3900
gttttctttc tttctgtttt tttttttttgt tttttttttt tttttttttt tttttttttt   3960
tgactaattt cacatgctct aaaaaccttc aaaggtgatt attttctcc tggaaactcc    4020
aggtccattc tgtttaaatc cctaagaatg tcagaattaa aataacaggg ctatcccgta   4080
attggaaata tttctttttt caggatgcta tagtcaattt agtaagtgac caccaaattg   4140
ttatttgcac taacaaagct caaaacacga taagtttact cctccatctc agtaataaaa   4200
attaagctgt aatcaacctt ctaggtttct cttgtcttaa aatgggtatt caaaaatggg   4260
gatctgtggt gtatgtatgg aaacacatac tccttaattt acctgttgtt ggaaactgga   4320
gaaatgattg tcgggcaacc gtttattttt tattgtattt tatttggttg agggattttt   4380
ttataaacag ttttacttgt gtcatatttt aaaattacta actgccatca cctgctgggg   4440
tcctttgtta ggtcattttc agtgactaat agggataatc caggtaactt tgaagagatg   4500
agcagtgagt gaccaggcag ttttttctgcc tttagctttg acagttctta attaagatca   4560
ttgaagacca gctttctcat aaatttctct tttttgaaaaa aagaaagcat ttgtactaag   4620
ctcctctgta agacaacatc ttaaatctta aaagtgttgt tatcatgact ggtgagagaa   4680
gaaaacattt tgttttttatt aaatggagca ttatttacaa aaagccattg ttgagaatta   4740
gatcccacat cgtataaata tctattaacc attctaaata aagagaactc cagtgttgct   4800
atgtgcaaga tcctctcttg gagctttttt gcatagcaat taaaggtgtg ctatttgtca   4860
gtagccattt ttttgcagtg atttgaagac caaagttgtt ttacagctgt gttaccgtta   4920
aaggttttt tttttatatg tattaaatca atttatcact gtttaaagct ttgaatatct    4980
gcaatctttg ccaaggtact ttttttattta aaaaaaaaca taactttgta aatattaccc   5040
tgtaatatta tatatactta ataaaacatt ttaagcta                           5078
```

<210> SEQ ID NO 14
<211> LENGTH: 312
<212> TYPE: PRT
<213> ORGANISM: Homo sapiens

<400> SEQUENCE: 14

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
```

|  |  |  |  | 85 |  |  |  | 90 |  |  |  | 95 |  |  |
|---|---|---|---|---|---|---|---|---|---|---|---|---|---|---|

Ser Leu Lys Met Asp Lys Ser Asp Ala Val Ser His Thr Gly Asn Tyr
                100                 105                 110

Thr Cys Glu Val Thr Glu Leu Thr Arg Glu Gly Thr Ile Ile Glu
        115                 120                 125

Leu Lys Tyr Arg Val Val Ser Trp Phe Ser Pro Asn Glu Asn Ile Leu
        130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
                195                 200                 205

Gly Leu Gly Leu Ile Val Thr Ser Thr Gly Ile Leu Ile Leu Leu His
                210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
                275                 280                 285

Met Lys Phe Val Ala Ser Asn Gln Lys Thr Ile Gln Pro Pro Arg Lys
                290                 295                 300

Ala Val Glu Glu Pro Leu Asn Glu
305                 310

```
<210> SEQ ID NO 15
<211> LENGTH: 5346
<212> TYPE: DNA
<213> ORGANISM: Homo sapiens

<400> SEQUENCE: 15
```

| | | | | |
|---|---|---|---|---|
| ggggagcagg | cggggagcg | ggcgggaagc | agtgggagcg | cgcgtgcgcg cggccgtgca | 60 |
| gcctgggcag | tgggtcctgc | ctgtgacgcg | cggcggcggt | cggtcctgcc tgtaacggcg | 120 |
| gcggcggctc | tgctccaga | cacctgcggc | ggcggcggcg | accccgcggc gggcgcggag | 180 |
| atgtggcccc | tggtagcggc | gctgttgctg | ggctcggcgt | gctgcggatc agctcagcta | 240 |
| ctatttaata | aaacaaaatc | tgtagaattc | acgttttgta | atgacactgt cgtcattcca | 300 |
| tgctttgtta | ctaatatgga | ggcacaaaac | actactgaag | tatacgtaaa gtggaaattt | 360 |
| aaaggaagag | atatttacac | ctttgatgga | gctctaaaca | agtccactgt ccccactgac | 420 |
| tttagtagtg | caaaaattga | agtctcacaa | ttactaaaag | gagatgcctc tttgaagatg | 480 |
| gataagagtg | atgctgtctc | acacacagga | aactacactt | gtgaagtaac agaattaacc | 540 |
| agagaaggtg | aaacgatcat | cgagctaaaa | tatcgtgttg | tttcatggtt ttctccaaat | 600 |
| gaaaatattc | ttattgttat | tttcccaatt | tttgctatac | tcctgttctg ggacagtttt | 660 |
| ggtattaaaa | cacttaaata | tagatccggt | ggtatggatg | agaaaacaat tgctttactt | 720 |
| gttgctggac | tagtgatcac | tgtcattgtc | attgttggag | ccattctttt cgtcccaggt | 780 |
| gaatattcat | taagaatgc | tactggcctt | ggtttaattg | tgacttctac agggatatta | 840 |

```
atattacttc actactatgt gtttagtaca gcgattggat taacctcctt cgtcattgcc    900
atattggtta ttcaggtgat agcctatatc ctcgctgtgg ttggactgag tctctgtatt    960
gcggcgtgta taccaatgca tggccctctt ctgatttcag gtttgagtat cttagctcta   1020
gcacaattac ttggactagt ttatatgaaa tttgtggctt ccaatcagaa gactatacaa   1080
cctcctagga aagctgtaga ggaaccccctt aatgcattca aagaatcaaa aggaatgatg   1140
aatgatgaat aactgaagtg aagtgatgga ctccgatttg gagagtagta agacgtgaaa   1200
ggaatacact tgtgtttaag caccatggcc ttgatgattc actgttgggg agaagaaaca   1260
agaaaagtaa ctggttgtca cctatgagac ccttacgtga ttgttagtta agttttattt   1320
caaagcagct gtaatttagt taataaaata attatgatct atgttgtttg cccaattgag   1380
atccagtttt ttgttgttat ttttaatcaa ttaggggcaa tagtagaatg gacaatttcc   1440
aagaatgatg cctttcaggt cctagggcct ctggcctcta ggtaaccagt ttaaattggt   1500
tcagggtgat aactacttag cactgccctg gtgattaccc agagatatct atgaaaacca   1560
gtggcttcca tcaaaccttt gccaactcag gttcacagca gctttgggca gttatggcag   1620
tatggcatta gctgagaggt gtctgccact tctgggtcaa tggaataata aattaagtac   1680
aggcaggaat ttggttggga gcatcttgta tgatctccgt atgatgtgat attgatggag   1740
atagtggtcc tcattcttgg gggttgccat tcccacattc ccccttcaac aaacagtgta   1800
acaggtcctt cccagattta gggtacttttt attgatggat atgttttcct tttattcaca   1860
taaccccttg aaaccctgtc ttgtcctcct gttacttgct tctgctgtac aagatgtagc   1920
accttttctc ctctttgaac atggtctagt gacacggtag caccagttgc aggaaggagc   1980
cagacttgtt ctcagagcac tgtgttcaca cttttcagca aaaatagcta tggttgtaac   2040
atatgtattc ccttcctctg atttgaaggc aaaaatctac agtgtttctt cacttctttt   2100
ctgatctggg gcatgaaaaa agcaagattg aaatttgaac tatgagtctc ctgcatggca   2160
acaaaatgtg tgtcaccatc aggccaacag gccagcccctt gaatggggat ttattactgt   2220
tgtatctatg ttgcatgata aacattcatc accttcctcc tgtagtcctg cctcgtactc   2280
cccttcccct atgattgaaa agtaaacaaa acccacattt cctatcctgg ttagaagaaa   2340
attaatgttc tgacagttgt gatcgcctgg agtacttttta gacttttagc attcgttttt   2400
tacctgtttg tggatgtgtg tttgtatgtg catacgtatg agataggcac atgcatcttc   2460
tgtatggaca aggtggggt acctacagga gagcaaaggt taattttgtg cttttagtaa   2520
aaacatttaa atacaaagtt ctttattggg tggaattata tttgatgcaa atatttgatc   2580
acttaaaact tttaaaactt ctaggtaatt tgccacgctt tttgactgct caccaatacc   2640
ctgtaaaaat acgtaattct tcctgtttgt gtaataagat attcatattt gtagttgcat   2700
taataatagt tatttcttag tccatcagat gttcccgtgt gcctctttta tgccaaattg   2760
attgtcatat ttcatgttgg gaccaagtag tttgcccatg gcaaacctaa atttatgacc   2820
tgctgaggcc tctcagaaaa ctgagcatac tagcaagaca gctcttcttg aaaaaaaaaa   2880
tatgtataca caaatatata cgtatatcta tatatacgta tgtatataca cacatgtata   2940
ttcttccttg attgtgtagc tgtccaaaat aataacatat atagagggag ctgtattcct   3000
ttatacaaat ctgatggctc ctgcagcact ttttccttct gaaaatattt acattttgct   3060
aacctagttt gttactttaa aaatcagttt tgatgaaagg agggaaaagc agatggactt   3120
gaaaagatc caagctccta ttagaaaagg tatgaaaatc tttatagtaa aatttttat   3180
```

|  |  |  |  |  |  |
|---|---|---|---|---|---|
| aaactaaagt | tgtaccttttt | aatatgtagt | aaactctcat | ttatttgggg | ttcgctcttg | 3240 |
| gatctcatcc | atccattgtg | ttctctttaa | tgctgcctgc | cttttgaggc | attcactgcc | 3300 |
| ctagacaatg | ccaccagaga | tagtgggggga | aatgccagat | gaaaccaact | cttgctctca | 3360 |
| ctagttgtca | gcttctctgg | ataagtgacc | acagaagcag | gagtcctcct | gcttgggcat | 3420 |
| cattgggcca | gttccttctc | tttaaatcag | atttgtaatg | gctcccaaat | tccatcacat | 3480 |
| cacatttaaa | ttgcagacag | tgttttgcac | atcatgtatc | tgttttgtcc | cataatatgc | 3540 |
| ttttttactcc | ctgatcccag | tttctgctgt | tgactcttcc | attcagtttt | atttattgtg | 3600 |
| tgttctcaca | gtgacaccat | ttgtcctttt | ctgcaacaac | ctttccagct | acttttgcca | 3660 |
| aattctattt | gtcttctcct | tcaaaacatt | ctcctttgca | gttcctcttc | atctgtgtag | 3720 |
| ctgctcttttt | gtctcttaac | ttaccattcc | tatagtactt | tatgcatctc | tgcttagttc | 3780 |
| tattagttttt | ttggccttgc | tcttctcctt | gattttaaaa | ttccttctat | agctagagct | 3840 |
| tttctttcttt | tcattctctc | ttcctgcagt | gttttgcata | catcagaagc | taggtacata | 3900 |
| agttaaatga | ttgagagttg | gctgtattta | gatttatcac | ttttttaatag | ggtgagcttg | 3960 |
| agagttttct | ttctttctgt | tttttttttt | tgtttttttt | tttttttttt | tttttttttt | 4020 |
| ttttgactaa | tttcacatgc | tctaaaaacc | ttcaaaggtg | attattttttc | tcctggaaac | 4080 |
| tccaggtcca | ttctgtttaa | atccctaaga | atgtcagaat | taaaataaca | gggctatccc | 4140 |
| gtaattggaa | atatttctttt | tttcaggatg | ctatagtcaa | tttagtaagt | gaccaccaaa | 4200 |
| ttgttatttg | cactaacaaa | gctcaaaaca | cgataagttt | actcctccat | ctcagtaata | 4260 |
| aaaattaagc | tgtaatcaac | cttctaggtt | tctcttgtct | taaaatgggt | attcaaaaat | 4320 |
| ggggatctgt | ggtgtatgta | tggaaacaca | tactccttaa | tttacctgtt | gttggaaact | 4380 |
| ggagaaatga | ttgtcgggca | accgttattt | ttttattgta | ttttatttgg | ttgagggatt | 4440 |
| tttttataaa | cagttttact | tgtgtcatat | tttaaaatta | ctaactgcca | tcacctgctg | 4500 |
| gggtcctttg | ttaggtcatt | ttcagtgact | aataggata | atccaggtaa | ctttgaagag | 4560 |
| atgagcagtg | agtgaccagg | cagttttttct | gcctttagct | ttgacagttc | ttaattaaga | 4620 |
| tcattgaaga | ccagctttct | cataaattttc | tcttttttgaa | aaaaagaaag | catttgtact | 4680 |
| aagctcctct | gtaagacaac | atcttaaatc | ttaaaagtgt | tgttatcatg | actggtgaga | 4740 |
| gaagaaaaca | ttttgttttt | attaaatgga | gcattattta | caaaaagcca | ttgttgagaa | 4800 |
| ttagatccca | catcgtataa | atatctatta | accattctaa | ataaagagaa | ctccagtgtt | 4860 |
| gctatgtgca | agatcctctc | ttggagcttt | tttgcatagc | aattaaaggt | gtgctatttg | 4920 |
| tcagtagcca | ttttttttgca | gtgatttgaa | gaccaaagtt | gttttacagc | tgtgttaccg | 4980 |
| ttaaaggttt | tttttttttat | atgtattaaa | tcaattatc | actgtttaaa | gctttgaata | 5040 |
| tctgcaatct | ttgccaaggt | actttttttat | ttaaaaaaaa | acataacttt | gtaaatatta | 5100 |
| ccctgtaata | ttatatatac | ttaataaaac | attttaagct | attttgttgg | gctatttcta | 5160 |
| ttgctgctac | agcagaccac | aagcacattt | ctgaaaaatt | taatttatta | atgtattttt | 5220 |
| aagttgctta | tattctaggt | aacaatgtaa | agaatgattt | aaaatattaa | ttatgaattt | 5280 |
| tttgagtata | atacccaata | agcttttaat | tagagcagag | ttttaattaa | aagttttaaa | 5340 |
| tcagtc |  |  |  |  |  | 5346 |

<210> SEQ ID NO 16
<211> LENGTH: 323
<212> TYPE: PRT
<213> ORGANISM: Homo sapiens

<400> SEQUENCE: 16

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu
```

<210> SEQ ID NO 17
<211> LENGTH: 293
<212> TYPE: PRT
<213> ORGANISM: Artificial Sequence
<220> FEATURE:
<223> OTHER INFORMATION: Synthetic polypeptide

<400> SEQUENCE: 17

```
Met Trp Pro Leu Ala Ala Ala Leu Leu Leu Gly Ser Cys Cys Cys Gly
1               5                   10                  15

Ser Ala Gln Leu Leu Phe Asn Lys Thr Lys Ser Val Glu Phe Thr Phe
```

```
            20                  25                  30
Cys Asn Asp Thr Val Val Ile Pro Cys Phe Val Thr Asn Met Glu Ala
        35                  40                  45
Gln Asn Thr Thr Glu Val Tyr Val Lys Trp Lys Phe Lys Gly Arg Asp
    50                  55                  60
Ile Tyr Thr Phe Asp Gly Ala Leu Asn Lys Ser Thr Val Pro Thr Asp
65                  70                  75                  80
Phe Ser Ser Ala Lys Ile Glu Val Ser Gln Leu Leu Lys Gly Asp Ala
                85                  90                  95
Ser Leu Lys Met Asp Lys Ser Asp Ala Val Ser His Thr Gly Asn Tyr
            100                 105                 110
Thr Cys Glu Val Thr Glu Leu Thr Arg Glu Gly Glu Thr Ile Ile Glu
        115                 120                 125
Leu Lys Tyr Arg Val Val Ser Trp Phe Ser Pro Asn Glu Asn Ile Leu
    130                 135                 140
Ile Val Ile Phe Pro Ile Phe Ala Ile Leu Leu Phe Trp Gly Gln Phe
145                 150                 155                 160
Gly Ile Lys Thr Leu Lys Tyr Arg Ser Gly Gly Met Asp Glu Lys Thr
                165                 170                 175
Ile Ala Leu Leu Val Ala Gly Leu Val Ile Thr Val Ile Val Ile Val
            180                 185                 190
Gly Ala Ile Leu Phe Val Pro Gly Glu Tyr Ser Leu Lys Asn Ala Thr
        195                 200                 205
Gly Leu Gly Leu Ile Val Thr Ser Thr Gly Ile Leu Ile Leu Leu His
    210                 215                 220
Tyr Tyr Val Phe Ser Thr Ala Ile Gly Leu Thr Ser Phe Val Ile Ala
225                 230                 235                 240
Ile Leu Val Ile Gln Val Ile Ala Tyr Ile Leu Ala Val Val Gly Leu
                245                 250                 255
Ser Leu Cys Ile Ala Ala Cys Ile Pro Met His Gly Pro Leu Leu Ile
            260                 265                 270
Ser Gly Leu Ser Ile Leu Ala Leu Ala Gln Leu Leu Gly Leu Val Tyr
        275                 280                 285
Met Lys Phe Val Glu
    290

<210> SEQ ID NO 18
<211> LENGTH: 305
<212> TYPE: PRT
<213> ORGANISM: Artificial Sequence
<220> FEATURE:
<223> OTHER INFORMATION: Synthetic polypeptide

<400> SEQUENCE: 18

Met Trp Pro Leu Ala Ala Ala Leu Leu Leu Gly Ser Cys Cys Cys Gly
1               5                   10                  15
Ser Ala Gln Leu Leu Phe Asn Lys Thr Lys Ser Val Glu Phe Thr Phe
            20                  25                  30
Cys Asn Asp Thr Val Val Ile Pro Cys Phe Val Thr Asn Met Glu Ala
        35                  40                  45
Gln Asn Thr Thr Glu Val Tyr Val Lys Trp Lys Phe Lys Gly Arg Asp
    50                  55                  60
Ile Tyr Thr Phe Asp Gly Ala Leu Asn Lys Ser Thr Val Pro Thr Asp
65                  70                  75                  80
Phe Ser Ser Ala Lys Ile Glu Val Ser Gln Leu Leu Lys Gly Asp Ala
```

```
                        85                  90                  95
Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
        130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Arg Thr Ile Gln Pro Pro Arg Asn
    290                 295                 300

Arg
305

<210> SEQ ID NO 19
<211> LENGTH: 312
<212> TYPE: PRT
<213> ORGANISM: Artificial Sequence
<220> FEATURE:
<223> OTHER INFORMATION: Synthetic polypeptide

<400> SEQUENCE: 19

Met Trp Pro Leu Ala Ala Ala Leu Leu Leu Gly Ser Cys Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
```

```
                130                 135                 140
Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
                195                 200                 205

Gly Leu Gly Leu Ile Val Thr Ser Thr Gly Ile Leu Ile Leu Leu His
                210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
                275                 280                 285

Met Lys Phe Val Ala Ser Asn Gln Arg Thr Ile Gln Pro Pro Arg Lys
                290                 295                 300

Ala Val Glu Glu Pro Leu Asn Glu
305                 310

<210> SEQ ID NO 20
<211> LENGTH: 323
<212> TYPE: PRT
<213> ORGANISM: Artificial Sequence
<220> FEATURE:
<223> OTHER INFORMATION: Synthetic polypeptide

<400> SEQUENCE: 20

Met Trp Pro Leu Ala Ala Ala Leu Leu Leu Gly Ser Cys Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
                35                  40                  45

Gln Asn Thr Thr Glu Val Tyr Val Lys Trp Lys Phe Lys Gly Arg Asp
                50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
                115                 120                 125

Leu Lys Tyr Arg Val Val Ser Trp Phe Ser Pro Asn Glu Asn Ile Leu
                130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
```

```
                180                 185                 190
Gly Ala Ile Leu Phe Val Pro Gly Glu Tyr Ser Leu Lys Asn Ala Thr
            195                 200                 205
Gly Leu Gly Leu Ile Val Thr Ser Thr Gly Ile Leu Ile Leu Leu His
        210                 215                 220
Tyr Tyr Val Phe Ser Thr Ala Ile Gly Leu Thr Ser Phe Val Ile Ala
225                 230                 235                 240
Ile Leu Val Ile Gln Val Ile Ala Tyr Ile Leu Ala Val Val Gly Leu
                245                 250                 255
Ser Leu Cys Ile Ala Ala Cys Ile Pro Met His Gly Pro Leu Leu Ile
            260                 265                 270
Ser Gly Leu Ser Ile Leu Ala Leu Ala Gln Leu Leu Gly Leu Val Tyr
        275                 280                 285
Met Lys Phe Val Ala Ser Asn Gln Arg Thr Ile Gln Pro Pro Arg Lys
            290                 295                 300
Ala Val Glu Glu Pro Leu Asn Ala Phe Lys Glu Ser Lys Gly Met Met
305                 310                 315                 320
Asn Asp Glu

<210> SEQ ID NO 21
<211> LENGTH: 22
<212> TYPE: DNA
<213> ORGANISM: Artificial Sequence
<220> FEATURE:
<223> OTHER INFORMATION: Synthetic primer

<400> SEQUENCE: 21
tgcagaagtc actaggagga at                                          22

<210> SEQ ID NO 22
<211> LENGTH: 27
<212> TYPE: DNA
<213> ORGANISM: Artificial Sequence
<220> FEATURE:
<223> OTHER INFORMATION: Synthetic probe

<400> SEQUENCE: 22
tcagtcaact tcttctgggt tgtttcc                                     27

<210> SEQ ID NO 23
<211> LENGTH: 23
<212> TYPE: DNA
<213> ORGANISM: Artificial Sequence
<220> FEATURE:
<223> OTHER INFORMATION: Synthetic primer

<400> SEQUENCE: 23
gtgccagact cactttctat cca                                         23

<210> SEQ ID NO 24
<211> LENGTH: 22
<212> TYPE: DNA
<213> ORGANISM: Artificial Sequence
<220> FEATURE:
<223> OTHER INFORMATION: Synthetic primer

<400> SEQUENCE: 24
tgctgccaat atacggcttc tg                                          22

<210> SEQ ID NO 25
<211> LENGTH: 26
```

```
<212> TYPE: DNA
<213> ORGANISM: Artificial Sequence
<220> FEATURE:
<223> OTHER INFORMATION: Synthetic probe

<400> SEQUENCE: 25
cagctctcat agccaactat ggtgcc                                          26

<210> SEQ ID NO 26
<211> LENGTH: 22
<212> TYPE: DNA
<213> ORGANISM: Artificial Sequence
<220> FEATURE:
<223> OTHER INFORMATION: Synthetic primer

<400> SEQUENCE: 26
tcaagcagag cctggttatc tg                                              22

<210> SEQ ID NO 27
<211> LENGTH: 23
<212> TYPE: DNA
<213> ORGANISM: Artificial Sequence
<220> FEATURE:
<223> OTHER INFORMATION: Synthetic primer

<400> SEQUENCE: 27
gtcgtcattc catgctttgt tac                                             23

<210> SEQ ID NO 28
<211> LENGTH: 30
<212> TYPE: DNA
<213> ORGANISM: Artificial Sequence
<220> FEATURE:
<223> OTHER INFORMATION: Synthetic probe

<400> SEQUENCE: 28
tggaggcaca aaacactact gaagtatacg                                      30

<210> SEQ ID NO 29
<211> LENGTH: 22
<212> TYPE: DNA
<213> ORGANISM: Artificial Sequence
<220> FEATURE:
<223> OTHER INFORMATION: Synthetic primer

<400> SEQUENCE: 29
ggacagtgga cttgtttaga gc                                              22

<210> SEQ ID NO 30
<211> LENGTH: 21
<212> TYPE: DNA
<213> ORGANISM: Artificial Sequence
<220> FEATURE:
<223> OTHER INFORMATION: Synthetic primer

<400> SEQUENCE: 30
ggcttggtgg ctgattgttc t                                               21
```

<210> SEQ ID NO 31
<211> LENGTH: 28
<212> TYPE: DNA
<213> ORGANISM: Artificial Sequence
<220> FEATURE:
<223> OTHER INFORMATION: Synthetic probe

<400> SEQUENCE: 31
agcacccaaa ctgatatgcc tgtatttg                                            28

<210> SEQ ID NO 32
<211> LENGTH: 23
<212> TYPE: DNA
<213> ORGANISM: Artificial Sequence
<220> FEATURE:
<223> OTHER INFORMATION: Synthetic primer

<400> SEQUENCE: 32
tgggaactgg tgtttcaagt cta                                                 23

<210> SEQ ID NO 33
<211> LENGTH: 158
<212> TYPE: DNA
<213> ORGANISM: Artificial Sequence
<220> FEATURE:
<223> OTHER INFORMATION: Synthetic polynucleotide

<400> SEQUENCE: 33
gcagacatga ttacttcaga gctttcaaag ctagatactg taccttgcat attccaacac         60
gcgatcgcat tttaagattt tccatcctag tggaaagata tgatttgatt catcctattt        120
actttgtata ttaaagtaca gtagaacctg ccactttt                                158

<210> SEQ ID NO 34
<211> LENGTH: 160
<212> TYPE: DNA
<213> ORGANISM: Artificial Sequence
<220> FEATURE:
<223> OTHER INFORMATION: Synthetic polynucleotide

<400> SEQUENCE: 34
ggatccattt taagtaatag aataggattt ttaattgttc cagtgtttct gtgatagagc         60
tgtcctgcac agacctgttt ctcgagataa cttcgtataa tgtatgctat acgaagttat        120
atgcatggcc tccgcgccgg gttttggcgc ctcccgcggg                              160

<210> SEQ ID NO 35
<211> LENGTH: 160
<212> TYPE: DNA
<213> ORGANISM: Artificial Sequence
<220> FEATURE:
<223> OTHER INFORMATION: Synthetic polynucleotide

<400> SEQUENCE: 35
catgtctgga ataacttcgt ataatgtatg ctatacgaag ttatgctagt aactataacg         60
gtcctaaggt agcgactagc attagtatgg aaggtccgtc cactgtccag gttcctcttg        120
cggagctctt tgtctctctg gactctgtat acactgcttg                              160

```
<210> SEQ ID NO 36
<211> LENGTH: 239
<212> TYPE: DNA
<213> ORGANISM: Artificial Sequence
<220> FEATURE:
<223> OTHER INFORMATION: Synthetic polynucleotide

<400> SEQUENCE: 36
ggatccattt taagtaatag aataggattt ttaattgttc cagtgtttct gtgatagagc      60
tgtcctgcac agacctgttt ctcgagataa cttcgtataa tgtatgctat acgaagttat     120
gctagtaact ataacggtcc taaggtagcg actagcatta gtatggaagg tccgtccact     180
gtccaggttc ctcttgcgga gctctttgtc tctctggact ctgtatacac tgcttgcat     239
```

MOUSE HAVING A HUMANIZED CLUSTER OF DIFFERENTIATION 47 GENE

CROSS-REFERENCE TO RELATED APPLICATIONS

This application is a continuation of U.S. patent application Ser. No. 15/982,174, filed May 17, 2018, which is a continuation of U.S. patent application Ser. No. 14/951,825, filed Nov. 25, 2015, now abandoned, which claims the benefit of U.S. Provisional Patent Application Ser. No. 62/087,992, filed Dec. 5, 2014, which is incorporated herein by reference in its entirety.

INCORPORATION BY REFERENCE OF SEQUENCE LISTING

The Sequence Listing in the ASCII text file, named as 32584YX_10108US04_SequenceListing.txt of 92 KB, created on Nov. 6, 2020, and submitted to the United States Patent and Trademark Office via EFS-Web, is incorporated herein by reference.

BACKGROUND

Cancer therapy can be separated into four main categories: chemo/radio therapy, hormone therapy, targeted therapy, and immunotherapy. An intense focus of medical research and development has focused on targeted therapy and significant improvements have been made, yet cancer remains a major challenge to patients and to the healthcare industry worldwide. This major challenge is due, in part, to the ability of cancer cells to evade the monitoring mechanisms of the innate and adaptive immune systems, which is partly the result of inhibition of phagocytic clearance. Currently, no in vivo system exists to optimally determine the therapeutic potential of new cancer therapies that are designed to activate phagocytic clearance of cancer cells and determine the molecular aspects of how cancer cells provide inhibitory signals to macrophages and phagocytic cells. Such a system provides a source for assays in phagocytosis and macrophage functions in vivo, and identification of new cancer therapies that are targeted at providing an anti-tumor environment by promoting pro-phagocytic signals to the immune system.

SUMMARY

The present invention encompasses the recognition that it is desirable to engineer non-human animals to permit improved systems for identifying and developing new cancer therapeutics. The present invention also encompasses the recognition that it is desirable to engineer non-human animals to permit improved engraftment of human hematopoietic stem cells. Further, the present invention also encompasses the recognition that non-human animals having a humanized CD47 gene and/or otherwise expressing, containing, or producing a human or humanized CD47 polypeptide are desirable, for example for use in identifying and developing cancer therapeutics that overcome systemic toxicity associated with blockade of CD47 and overcome CD47-mediated inhibition of phagocytosis of tumor cells, and provide a more efficient in vivo system for engraftment of human hemotopoietic stem cells that provides an increase in homeostasis of a broader number of human cell types.

In some embodiments, the present invention provides a non-human animal having a genome comprising a CD47 gene that includes genetic material from two different species (e.g., a human and a non-human). In some embodiments, the CD47 gene of the non-human animals as described herein encodes a CD47 polypeptide that contains human and non-human portions, wherein the human and non-human portions are linked together and form a functional CD47 polypeptide.

In some embodiments, a non-human animal of the present invention comprises a CD47 gene that comprises an endogenous portion and a human portion, wherein the endogenous and human portions are operably linked to an endogenous promoter.

In some embodiments, an endogenous portion comprises exon 1 and the exons downstream of exon 7 of an endogenous CD47 gene. In some certain embodiments, exon 1 and the exons downstream of exon 7 of an endogenous CD47 gene are at least 50%, at least 55%, at least 60%, at least 65%, at least 70%, at least 75%, at least 80%, at least 85%, at least 90%, at least 95%, or at least 98% identical to the corresponding exon 1 and the exons downstream of exon 7 of a mouse CD47 gene that appears in Table 3. In some embodiments, exon 1 and the exons downstream of exon 7 of an endogenous CD47 gene are identical to the corresponding exon 1 and the exons downstream of exon 7 of a mouse CD47 gene that appears in Table 3.

In some embodiments, a human portion encodes amino acids 16-292 of a human CD47 polypeptide. In some embodiments, a human portion encodes amino acids 19-292 of a human CD47 polypeptide. In some embodiments, a human portion encodes amino acids 19-141 of a human CD47 polypeptide. In some embodiments, a human portion encodes amino acids 19-127 of a human CD47 polypeptide. In some embodiments, a human portion comprises exons 2-7 of a human CD47 gene.

In some embodiments, exons 2-7 of a human CD47 gene are at least 50%, at least 55%, at least 60%, at least 65%, at least 70%, at least 75%, at least 80%, at least 85%, at least 90%, at least 95%, or at least 98% identical to the corresponding exons 2-7 of a human CD47 gene that appears in Table 3. In some embodiments, exons 2-7 of a human CD47 gene are identical to the corresponding exons 2-7 of a human CD47 gene that appears in Table 3.

In some embodiments, a non-human animal of the present invention expresses a CD47 polypeptide comprising an extracellular portion of a human CD47 polypeptide and an intracellular portion of an endogenous CD47 polypeptide. In some embodiments, a CD47 polypeptide comprises a transmembrane portion of a human CD47 polypeptide. In other embodiments, a CD47 polypeptide comprises a transmembrane portion of a non-human CD47 polypeptide. In some embodiments, a CD47 polypeptide is translated in a cell of a non-human animal with a non-human signal peptide. In some certain embodiments, a non-human signal peptide is a rodent (e.g., a mouse or a rat) signal peptide.

In some embodiments, a CD47 polypeptide of the present invention is expressed from an endogenous non-human CD47 gene.

In some embodiments, an intracellular portion of an endogenous CD47 polypeptide comprises an intracytoplasmic tail that has an amino acid sequence that is at least 50%, at least 55%, at least 60%, at least 65%, at least 70%, at least 75%, at least 80%, at least 85%, at least 90%, at least 95%, or at least 98% identical to an intracytoplasmic tail of a mouse CD47 polypeptide that appears in Table 3. In some embodiments, an intracellular portion of the endogenous CD47 polypeptide comprises an intracytoplasmic tail that has an amino acid sequence that is identical to an intracytoplasmic tail of a mouse CD47 polypeptide that appears in Table 3.

In some embodiments, an extracellular portion of a human CD47 polypeptide comprises amino acids corresponding to residues 19-141 of a human CD47 polypeptide. In some embodiments, an extracellular portion of a human CD47 polypeptide comprises amino acids corresponding to residues 19-127 of a human CD47 polypeptide. In some embodiments, the extracellular portion of a human CD47 polypeptide comprises an amino acid sequence that is at least 50%, at least 55%, at least 60%, at least 65%, at least 70%, at least 75%, at least 80%, at least 85%, at least 90%, at least 95%, or at least 98% identical to a corresponding amino acid sequence of an extracellular portion of a human CD47 polypeptide that appears in Table 3. In some embodiments, an extracellular portion of a human CD47 polypeptide comprises an amino acid sequence that is identical to a corresponding amino acid sequence of an extracellular portion of a human CD47 polypeptide that appears in Table 3.

In some embodiments, the present invention provides a CD47 polypeptide encoded by the CD47 gene of a non-human animal as described herein. In some certain embodiments, an encoded CD47 polypeptide comprises an amino acid sequence that is at least 50%, at least 55%, at least 60%, at least 65%, at least 70%, at least 75%, at least 80%, at least 85%, at least 90%, at least 95%, or at least 98% identical to SEQ ID NO: 17, SEQ ID NO: 18, SEQ ID NO: 19 or SEQ ID NO: 20. In some certain embodiments, an encoded CD47 polypeptide comprises an amino acid sequence that is identical to SEQ ID NO: 17, SEQ ID NO: 18, SEQ ID NO: 19 or SEQ ID NO: 20.

In some embodiments, the present invention provides a humanized CD47 gene comprising one or more exons of a non-human CD47 gene operably linked to one or more exons of a human CD47 gene. In some certain embodiments, a humanized CD47 gene of the present invention comprises non-human exons that encode an intracellular portion of a CD47 polypeptide and human exons that encode an extracellular portion of a human CD47 polypeptide. In some embodiments, a humanized CD47 gene also comprises human exons that encode a transmembrane portion of a human CD47 polypeptide. In some certain embodiments, a humanized CD47 gene of the present invention comprises non-human exons that encode a signal peptide, in whole or in part, and an intracellular portion of a CD47 polypeptide, and human exons that encode an extracellular portion and optionally a transmembrane portion of a CD47 polypeptide.

In some embodiments, the present invention provides an isolated cell or tissue from a non-human animal as described herein. In some embodiments, the present invention provides an isolated cell or tissue comprising a CD47 gene as described herein. In some embodiments, a cell is selected from a dendritic cell, lymphocyte (e.g., a B or T cell), macrophage and a monocyte. In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and a combination thereof.

In some embodiments, the present invention provides a non-human embyronic stem cell whose genome comprises a CD47 gene as described herein. In some embodiments, a non-human embyronic stem cell is a mouse embyronic stem cell and is from a 129 strain, C57BL/6 strain or a BALB/c strain. In some embodiments, a non-human embyronic stem cell is a mouse embyronic stem cell and is from a mixture of 129 and C57BL/6 strains.

In some embodiments, the present invention provides the use of a non-human embryonic stem cell as described herein to make a non-human animal. In some certain embodiments, a non-human embryonic stem cell is a mouse embyronic stem cell and is used to make a mouse comprising a CD47 gene as described herein. In some certain embodiments, a non-human embryonic stem cell is a rat embyronic stem cell and is used to make a rat comprising a CD47 gene as described herein.

In some embodiments, the present invention provides a non-human embyro comprising, made from, obtained from, or generated from a non-human embyronic stem cell comprising a CD47 gene as described herein. In some certain embodiments, a non-human embryo is a rodent embyro. In some embodiments, a rodent embryo is a mouse embryo. In some embodiments, a rodent embryo is a rat embryo.

In some embodiments, the present invention provides a method of making a non-human animal that expresses a CD47 polypeptide from an endogenous CD47 gene, wherein the CD47 polypeptide comprises a human sequence, the method comprising inserting a genomic fragment into an endogenous CD47 gene in a non-human embryonic stem cell, said genomic fragment comprising a nucleotide sequence that encodes a human CD47 polypeptide in whole or in part; obtaining a non-human embryonic stem cell comprising an endogenous CD47 gene that comprises the nucleotide sequence that encodes a human CD47 polypeptide in whole or in part; and creating a non-human animal using the non-human embryonic stem cell comprising said nucleotide sequence that encodes a human CD47 polypeptide in whole or in part.

In some embodiments, a human sequence comprises amino acids corresponding to residues 19-141 (or 19-292) of a human CD47 polypeptide. In some embodiments, a human sequence comprises amino acids corresponding to residues 19-127 of a human CD47 polypeptide.

In some embodiments, a nucleotide sequence comprises exons 2-7 of a human CD47 gene. In some embodiments, a nucleotide sequence comprises one or more selection markers. In some embodiments, a nucleotide sequence comprises one or more site-specific recombination sites.

In some embodiments, the method further comprises a step of inserting a genomic fragment into an endogenous SIRPα gene of a non-human embryonic stem cell, said genomic fragment comprising a nucleotide sequence that encodes a human SIRPα polypeptide in whole or in part (e.g., encodes an extracellular portion of a human SIRPα polypeptide). In some certain embodiments, a genomic fragment comprising a nucleotide sequence that encodes a human SIRPα polypeptide in whole or in part (e.g., encodes an extracellular portion of a human SIRPα polypeptide) is inserted into an endogenous SIRPα gene of the non-human embryonic stem cell prior to an insertion into an endogenous CD47 gene.

In some embodiments, the method further comprises breeding a non-human animal comprising an endogenous CD47 gene that includes a nucleotide sequence that encodes a human CD47 polypeptide, in whole or in part, with a second non-human animal, said second non-human animal having a genome comprising a SIRPα gene that encodes a SIRPα polypeptide comprising an extracellular portion of a human SIRPα polypeptide (e.g., amino acids corresponding to residues 28-362 of a human SIRPα polypeptide) and an intracellular portion of an endogenous SIRPα polypeptide.

In some embodiments, the present invention provides a method of providing a non-human animal whose genome comprises a CD47 gene that encodes an extracellular portion of a human CD47 polypeptide linked to an intracellular portion of an endogenous CD47 polypeptide, the method comprising modifying the genome of a non-human animal so that it comprises a CD47 gene that encodes the extracellular portion of a human CD47 polypeptide linked to the intracellular portion of an endogenous CD47 polypeptide thereby providing said non-human animal. In some embodiments, a CD47 gene encodes a CD47 polypeptide that comprises an extracellular portion and a transmembrane portion of a human CD47 polypeptide linked to an intracellular portion of an endogenous non-human CD47 polypeptide. In other embodiments, a CD47 gene encodes a CD47 polypeptide that comprises an extracellular portion of a human CD47 polypeptide linked to a transmembrane portion and an intracellular portion of an endogenous non-human CD47 polypeptide.

In some embodiments, the modifying the genome of a non-human animal is performed in a non-human embryonic stem cell. In some certain embodiments, the non-human embryonic stem cell is a rodent embryonic stem cell; in some embodiments, a mouse embryonic stem cell; in some embodiments, a rat embryonic stem cell.

In some embodiments, the method further comprises modifying the genome of the non-human animal so that it comprises a SIRPα gene that encodes the extracellular portion of a human SIRPα polypeptide (e.g., amino acids corresponding to residues 28-362 of a human SIRPα polypeptide) linked to the intracellular portion of an endogenous SIRPα polypeptide. In some certain embodiments, the modifying the genome of the non-human animal so that it comprises a SIRPα gene that encodes the extracellular portion of a human SIRPα polypeptide (e.g., amino acids corresponding to residues 28-362 of a human SIRPα polypeptide) linked to the intracellular portion of an endogenous SIRPα polypeptide is performed prior to modifying the genome of the non-human animal so that it comprises a CD47 gene that encodes the extracellular portion and optionally a transmembrane portion of a human CD47 polypeptide linked to the intracellular portion of an endogenous CD47 polypeptide.

In some embodiments, the method further comprises breeding a non-human animal whose genome comprises a CD47 gene that encodes an extracellular portion of a human CD47 polypeptide linked to an intracellular portion of an endogenous CD47 polypeptide with a second non-human animal, said second non-human animal having a genome comprising a SIRPα gene that encodes a SIRPα polypeptide comprising an extracellular portion of a human SIRPα polypeptide (e.g., amino acids corresponding to residues 28-362 of a human SIRPα polypeptide) and an intracellular portion of an endogenous SIRPα polypeptide.

In some embodiments, the present invention provides a non-human animal obtainable by methods as described herein.

In some embodiments, the present invention provides a method of engrafting human cells into a non-human animal, the method comprising steps of providing a non-human animal whose genome comprises a CD47 gene that encodes the extracellular portion of a human CD47 polypeptide linked to the intracellular portion of an endogenous CD47 polypeptide; and transplanting one or more human cells into said non-human animal. In some certain embodiments, the method further comprises a step of assaying engraftment of the one or more human cells in said non-human animal. In some certain embodiments, a step of assaying comprises comparing the engraftment of the one or more human cells to the engraftment in one or more wild-type non-human animals or in one or more non-human animals whose genome does not comprise a CD47 gene that encodes the extracellular portion of a human CD47 polypeptide linked to the intracellular portion of an endogenous CD47 polypeptide.

In some embodiments, human cells are hematopoietic stem cells. In some embodiments, human cells are transplanted intravenously. In some embodiments, human cells are transplanted intraperitoneally. In some embodiments, human cells are transplanted subcutaneously.

In some embodiments, the present invention provides a method of assessing the therapeutic efficacy of a drug targeting human cells, the method comprising providing a non-human animal whose genome comprises a CD47 gene that encodes an extracellular portion of a human CD47 polypeptide linked to an intracellular portion of an endogenous CD47 polypeptide; transplanting one or more human cells into said non-human animal; administering a drug candidate to said non-human animal; and monitoring the human cells in the non-human animal to determine the therapeutic efficacy of the drug candidate.

In some embodiments, human cells are cancer cells and the drug candidate is an anti-cancer drug candidate. In some certain embodiments, a drug candidate is an antibody.

In some embodiments, a non-human animal further comprises human immune cells. In some certain embodiments, a drug candidate is a bi-specific antibody that binds human CD47 and an antigen on transplanted human cancer cells.

In some embodiments, the present invention provides a method comprising providing one or more cells whose genome includes a CD47 gene that encodes an extracellular portion of a human CD47 polypeptide linked to an intracellular portion of an endogenous CD47 polypeptide; incubating the one or more cells with a labeled substrate; and measuring phagocytosis of the labeled substrate by the one or more cells. In some embodiments, the substrate is fluorescently labeled. In some embodiments, the substrate is labeled with an antibody. In some embodiments, the substrate is one or more red blood cells. In some embodiments, the substrate is one or more bacterial cells. In some embodiments, the substrate is one or more tumor cells.

In some embodiments, the present invention provides a method comprising providing a non-human animal whose genome includes a CD47 gene that encodes an extracellular portion of a human CD47 polypeptide linked to an intracellular portion of an endogenous CD47 polypeptide; exposing the non-human animal to an antigen; and measuring phagocytosis of the antigen by one or more cells of the non-human animal. In some embodiments, the step of exposing comprises exposing the non-human animal to an antigen that is fluorescently labeled. In some embodiments, the step of exposing comprises exposing the non-human animal to one or more cells that comprise the antigen. In some embodiments, the step of exposing comprises exposing the non-human animal to one or more human cells comprising the antigen or to one or more bacterial cells comprising the antigen. In some embodiments, the step of exposing comprises exposing the non-human animal to one or more cells that have been transformed with the antigen so that the antigen is expressed on the surface of the one or more transformed cells. In some embodiments, the step of exposing comprises exposing the non-human animal to one or more tumor cells that comprise the antigen.

In some embodiments, the present invention provides methods for identification or validation of a drug or vaccine, the method comprising the steps of delivering a drug or vaccine to a non-human animal whose genome includes a CD47 gene that encodes an extracellular portion of a human CD47 polypeptide linked to an intracellular portion of an endogenous CD47 polypeptide, and monitoring one or more of the immune response to the drug or vaccine, the safety profile of the drug or vaccine, or the effect on a disease or condition. In some embodiments, monitoring the safety profile includes determining if the non-human animal exhibits a side effect or adverse reaction as a result of delivering the drug or vaccine. In some embodiments, a side effect or adverse reaction is selected from morbidity, mortality, alteration in body weight, alteration of the level of one or more enzymes (e.g., liver), alteration in the weight of one or more organs, loss of function (e.g., sensory, motor, organ, etc.), increased susceptibility to one or more diseases, alterations to the genome of the non-human animal, increase or decrease in food consumption and complications of one or more diseases.

In some embodiments, the present invention provides use of a non-human animal as described herein in the development of a drug or vaccine for use in medicine, such as use as a medicament.

In some embodiments, the present invention provides use of a non-human animal as described herein in the manufacture of a medicament for the treatment of cancer or a neoplasm.

In some embodiments, the present invention provides use of a non-human animal as described herein to assess the efficacy of a therapeutic drug targeting human cells. In various embodiments, a non-human animal of the present invention is transplanted with human cells and a drug candidate targeting said human cells is administered to the animal. In some embodiments, efficacy of the drug is determined by monitoring the human cells in the non-human animal after the administration of the drug.

In some embodiments, the present invention provides a non-human animal or cell as described herein for use in the development and/or identification of a drug (e.g., an antibody) for therapy or diagnosis.

In some embodiments, the present invention provides a non-human animal or cell as described herein for use in the development and/or identification of a drug (e.g., an antibody) for the treatment, prevention or amelioration of cancer or a neoplasm.

In some embodiments, the present invention provides a method of assessing the pharmacokinetics of a drug targeting human CD47, the method comprising the steps of administering the drug to a non-human animal as described herein, and performing an assay to determine one or more pharmacokinetic properties of the drug targeting human CD47.

In some embodiments, the present invention provides a method of assessing the on-target toxicity of a drug targeting human CD47, the method comprising the steps of administering the drug to a non-human animal as described herein, and performing an assay for one or more parameters associated with on-target toxicity of a drug.

In some embodiments, the present invention provides a method of assessing the off-target toxicity of a drug targeting human CD47, the method comprising the steps of administering the drug to a non-human animal as described herein, and performing an assay for one or more parameters associated with off-target toxicity of a drug.

In many embodiments, a non-human animal as described herein is a rodent whose genome includes a CD47 gene that encodes an extracellular portion of a human CD47 polypeptide linked to an intracellular portion of an endogenous CD47 polypeptide; in some embodiments, a rodent is a mouse; in some embodiments, a rodent is a rat.

In some embodiments, a drug targeting human CD47 is a CD47 antagonist. In some certain embodiments, a CD47 antagonsit is an anti-CD47 antibody. In some embodiments, a drug targeting human CD47 is a CD47 agonist.

In various embodiments, a CD47 gene of the present invention includes a CD47 gene as described herein. In various embodiments, a CD47 polypeptide of the present invention includes a CD47 polypeptide as described herein.

In various embodiments, a non-human animal of the present invention does not detectably express a full-length endogenous non-human CD47 polypeptide. In various embodiments, a non-human animal of the present invention does not detectably express an extracellular portion of an endogenous CD47 polypeptide. In various embodiments, a non-human animal of the present invention does not detectably express an extracellular portion of both an endogenous CD47 polypeptide and an endogenous SIRPα polypeptide.

In various embodiments, an extracellular portion of a human CD47 polypeptide comprises amino acids corresponding to residues 19-141 of a human CD47 polypeptide as described herein.

In various embodiments, an N-terminal immunoglobulin V domain of a human CD47 polypeptide comprises amino acids corresponding to residues 19-127 of a human CD47 polypeptide as described herein.

In various embodiments, non-human animals, cells, tissues, embryonic stem cells and/or embryos of the present invention have a genome that further comprises a SIRPα gene that encodes a SIRPα polypeptide comprising an extracellular portion of a human SIRPα polypeptide (e.g., amino acids corresponding to residues 28-362 of a human SIRPα polypeptide) and an intracellular portion of an endogenous SIRPα polypeptide.

In various embodiments, a non-human animal of the present invention is a rodent; in some embodiments, a mouse; in some embodiments, a rat.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The Drawings included herein, which are composed of the following Figures, are for illustration purposes only and not for limitation.

DEFINITIONS

Figure 1:
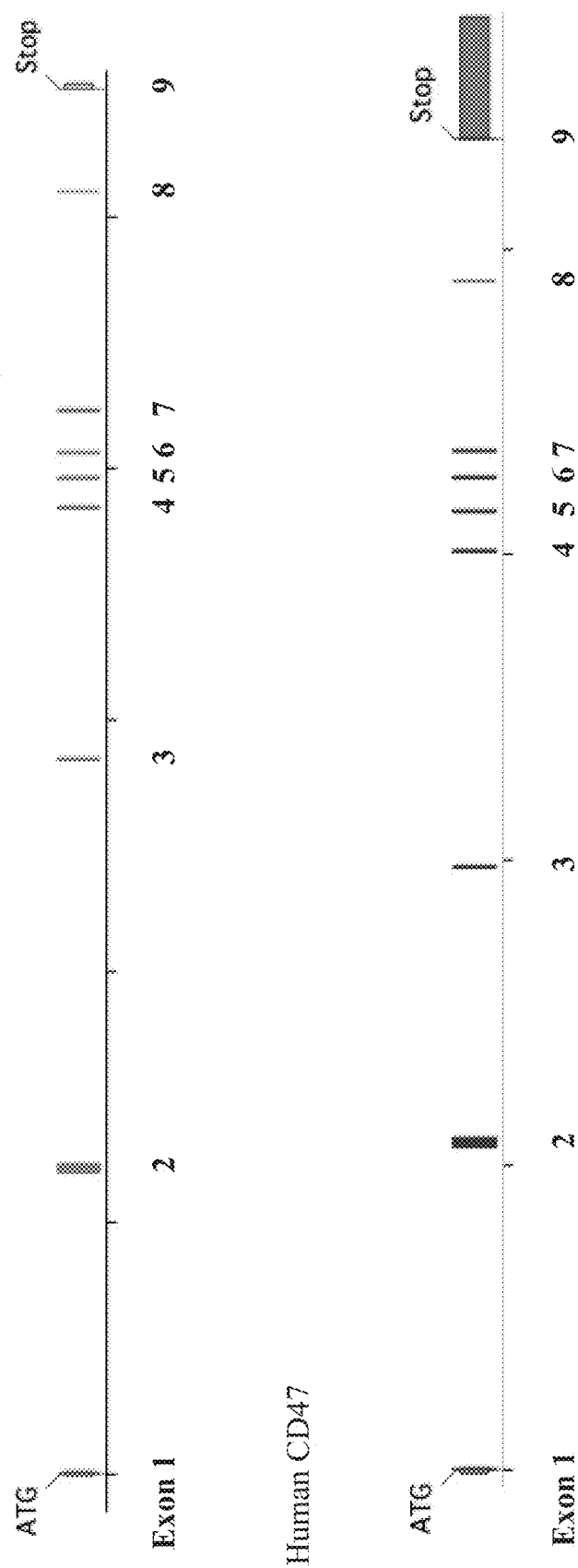
FIG. 1 shows a diagram, not to scale, of the genomic organization of a non-human (e.g., mouse) and human Cluster of Differentiation 47 (CD47) genes. Exons are numbered beneath each exon.

This invention is not limited to particular methods and experimental conditions described herein, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned herein are hereby incorporated by reference.

The term "approximately", as applied herein to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "biologically active", as used herein, refers to a characteristic of any agent that has activity in a biological system, in vitro or in vivo (e.g., in an organism). For instance, an agent that, when present in an organism, has a biological effect within that organism, is considered to be biologically active. In particular embodiments, where a protein or polypeptide is biologically active, a portion of that protein or polypeptide that shares at least one biological activity of the protein or polypeptide is typically referred to as a "biologically active" portion.

The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

The term "conservative", as used herein to describe a conservative amino acid substitution, refers to substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include: aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet et al. (1992) Exhaustive Matching of the Entire Protein Sequence Database, *Science* 256:1443-45, hereby incorporated by reference. In some embodiments, the substitution is a moderately conservative substitution wherein the substitution has a nonnegative value in the PAM250 log-likelihood matrix.

The term "control", as used herein, refers to the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. As used herein, a "control" may refer to a "control animal". A "control animal" may have a modification as described herein, a modification that is different as described herein, or no modification (i.e., a wild-type animal). In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

The term "disruption", as used herein, refers to the result of a homologous recombination event with a DNA molecule (e.g., with an endogenous homologous sequence such as a gene or gene locus. In some embodiments, a disruption may achieve or represent an insertion, deletion, substitution, replacement, missense mutation, or a frame-shift of a DNA sequence(s), or any combination thereof. Insertions may include the insertion of entire genes or fragments of genes, e.g., exons, which may be of an origin other than the endogenous sequence (e.g., a heterologous sequence). In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter sequence of a gene or an encoded gene product (e.g., an encoded protein). In some embodiments, a disruption may truncate or fragment a gene or an encoded gene product (e.g., an encoded protein). In some embodiments, a disruption may extend a gene or an encoded gene product; in some such embodiments, a disruption may achieve assembly of a fusion protein. In some embodiments, a disruption may affect level but not activity of a gene or gene product. In some embodiments, a disruption may affect activity but not level of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

The terms "determining", "measuring", "evaluating", "assessing", "assaying" and "analyzing" are used interchangeably herein to refer to any form of measurement, and include determining if an element is present or not. These terms include both quantitative and/or qualitative determinations. Assaying may be relative or absolute. "Assaying for the presence of" can be determining the amount of something present and/or determining whether or not it is present or absent.

The phrase "endogenous locus" or "endogenous gene", as used herein, refers to a genetic locus found in a parent or reference organism prior to introduction of a disruption, deletion, replacement, alteration, or modification as described herein. In some embodiments, the endogenous locus has a sequence found in nature. In some embodiments, the endogenous locus is a wild type locus. In some embodiments, the reference organism is a wild-type organism. In some embodiments, the reference organism is an engineered organism. In some embodiments, the reference organism is a laboratory-bred organism (whether wild-type or engineered).

The phrase "endogenous promoter" refers to a promoter that is naturally associated, e.g., in a wild-type organism, with an endogenous gene.

The term "heterologous", as used herein, refers to an agent or entity from a different source. For example, when used in reference to a polypeptide, gene, or gene product or present in a particular cell or organism, the term clarifies that the relevant polypeptide, gene, or gene product: 1) was engineered by the hand of man; 2) was introduced into the cell or organism (or a precursor thereof) through the hand of man (e.g., via genetic engineering): and/or 3) is not naturally produced by or present in the relevant cell or organism (e.g., the relevant cell type or organism type).

The term "host cell", as used herein, refers to a cell into which a heterologous (e.g., exogenous) nucleic acid or protein has been introduced. Persons of skill upon reading this disclosure will understand that such terms refer not only to the particular subject cell, but also is used to refer to the progeny of such a cell. Because certain modifications may occur in succeeding generations due to either mutation or environmental influences, such progeny may not, in fact, be identical to the parent cell, but are still included within the scope of the term "host ce" as used herein. In some embodiments, a host cell is or comprises a prokaryotic or eukaryotic cell. In general, a host cell is any cell that is suitable for receiving and/or producing a heterologous nucleic acid or protein, regardless of the Kingdom of life to which the cell is designated. Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, W138, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell). In some embodiments, a host cell is or comprises an isolated cell. In some embodiments, a host cell is part of a tissue. In some embodiments, a host cell is part of an organism.

The term "humanized", is used herein in accordance with its art-understood meaning to refer to nucleic acids or proteins whose structures (i.e., nucleotide or amino acid sequences) include portions that correspond substantially or identically with structures of a particular gene or protein found in nature in a non-human animal, and also include portions that differ from that found in the relevant particular non-human gene or protein and instead correspond more closely with comparable structures found in a corresponding human gene or protein. In some embodiments, a "humanized" gene is one that encodes a polypeptide having substantially the amino acid sequence as that of a human polypeptide (e.g., a human protein or portion thereof—e.g., characteristic portion thereof). To give but one example, in the case of a membrane receptor, a "humanized" gene may encode a polypeptide having an extracellular portion having an amino acid sequence as that of a human extracellular portion and the remaining sequence as that of a non-human (e.g., mouse) polypeptide. In some embodiments, a humanized gene comprises at least a portion of a DNA sequence of a human gene. In some embodiment, a humanized gene comprises an entire DNA sequence of a human gene. In some embodiments, a humanized protein comprises a sequence having a portion that appears in a human protein. In some embodiments, a humanized protein comprises an entire sequence of a human protein and is expressed from an endogenous locus of a non-human animal that corresponds to the homolog or ortholog of the human gene.

The term "identity", as used herein in connection with a comparison of sequences, refers to identity as determined by a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008).

The term "isolated", as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when: a) by virtue of its origin or source of derivation is not associated with some or all of the components that accompany it in its native state in nature; b) it is substantially free of other polypeptides or nucleic acids of the same species from the species that produces it in nature; or c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components: a) with which it is associated in nature; and/or b) with which it was associated when initially produced.

The phrase "non-human animal", as used herein, refers to any vertebrate organism that is not a human. In some embodiments, a non-human animal is acyclostome, a bony fish, a cartilaginous fish (e.g., a shark or a ray), an amphibian, a reptile, a mammal, or a bird. In some embodiments, a non-human mammal is a primate, a goat, a sheep, a pig, a dog, a cow, or a rodent. In some embodiments, a non-human animal is a rodent such as a rat or a mouse.

The phrase "nucleic acid", as used herein, in its broadest sense, refers to any compound and/or substance that is or can be incorporated into an oligonucleotide chain. In some embodiments, a "nucleic acid" is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a "nucleic acid" is, comprises, or consists of one or more natural nucleic acid residues. In some embodiments, a "nucleic acid" is, comprises, or consists of one or more nucleic acid analogs. In some embodiments, a nucleic acid analog differs from a "nucleic acid" in that it does not utilize a phosphodiester backbone. For example, in some embodiments, a "nucleic acid" is, comprises, or consists of one or more "peptide nucleic acids", which are known in the art and have peptide bonds instead of phosphodiester bonds in the backbone, are considered within the scope of the present invention. Alternatively or additionally, in some embodiments, a "nucleic acid" has one or more phosphorothioate and/or 5'-N-phosphoramidite linkages rather than phosphodiester bonds. In some embodiments, a "nucleic acid" is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a "nucleic acid" is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a "nucleic acid" comprises one or more modified sugars (e.g., 2'-fluororibose, ribose, 2'-deoxyribose, arabinose, and hexose) as compared with those in natural nucleic acids. In some embodiments, a "nucleic acid" has a nucleotide sequence that encodes a functional gene product such as an RNA or protein. In some embodiments, a "nucleic acid" includes one or more introns. In some embodiments, a "nucleic acid" is prepared by one or more of isolation from a natural source, enzymatic synthesis by polymerization based on a complementary template (in vivo or in vitro), reproduction in a recombinant cell or system, and chemical synthesis. In some embodiments, a "nucleic acid" is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a "nucleic acid" is single stranded; in some embodiments, a "nucleic acid" is double stranded. In some embodiments, a "nucleic acid" has a nucleotide sequence comprising at least one element that encodes, or is the complement of a sequence that encodes, a polypeptide. In some embodiments, a "nucleic acid" has enzymatic activity.

The phrase "operably linked", as used herein, refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence", as used herein, refers to polynucleotide sequences, which are necessary to effect the expression and processing of coding sequences to which they are ligated. "Expression control sequences" include: appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

The term "polypeptide", as used herein, refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that contains portions that occur in nature separately from one another (i.e., from two or more different organisms, for example, human and non-human portions). In some embodiments, a polypeptide has an amino acid sequence that is engineered in that it is designed and/or produced through action of the hand of man.

The term "recombinant", as used herein, is intended to refer to polypeptides (e.g., CD47 polypeptides as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., (1997) *TIB Tech.* 15:62-70; Azzazy H., and Highsmith W. E., (2002) *Clin Biochem.* 35:425-445; Gavilondo J. V., and Larrick J. W. (2002) *BioTechniques* 29:128-145; Hoogenboom H., and Chames P. (2000) *Immunology Today* 21:371-378), antibodies isolated from an animal (e.g., a mouse) that is transgenic for human immunoglobulin genes (see e.g., Taylor, L. D., et al. (1992) *Nuc. Acid Res.* 20:6287-6295; Kellermann S-A., and Green L. L. (2002) *Current Opinion in Biotechnology* 13:593-597: Little M. el al. (2000) *Immunology Today* 21:364-370; Murphy, A. J., et al. (2014) *Proc. Natl. Acad. Sci. U.S.A.* 111(14):5153-5158) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements result from mutagenesis (e.g., in vivo or in vitro) of a known sequence element, e.g., from a natural or synthetic source. For example, in some embodiments, a recombinant polypeptide is comprised of sequences found in the genome of a source organism of interest (e.g., human, mouse, etc.). In some embodiments, a recombinant polypeptide has an amino acid sequence that resulted from mutagenesis (e.g., in vitro or in vivo, for example in a non-human animal), so that the amino acid sequences of the recombinant polypeptides are sequences that, while originating from and related to polypeptides sequences, may not naturally exist within the genome of a non-human animal in vivo.

The term "replacement" is used herein to refer to a process through which a "replaced" nucleic acid sequence (e.g., a gene) found in a host locus (e.g., in a genome) is removed from that locus, and a different, "replacement" nucleic acid is located in its place. In some embodiments, the replaced nucleic acid sequence and the replacement nucleic acid sequences are comparable to one another in that, for example, they are homologous to one another and/or contain corresponding elements (e.g., protein-coding elements, regulatory elements, etc.). In some embodiments, a replaced nucleic acid sequence includes one or more of a promoter, an enhancer, a splice donor site, a splice receiver site, an intron, an exon, an untranslated region (UTR); in some embodiments, a replacement nucleic acid sequence includes one or more coding sequences. In some embodiments, a replacement nucleic acid sequence is a homolog of the replaced nucleic acid sequence. In some embodiments, a replacement nucleic acid sequence is an ortholog of the replaced sequence. In some embodiments, a replacement nucleic acid sequence is or comprises a human nucleic acid sequence. In some embodiments, including where the replacement nucleic acid sequence is or comprises a human nucleic acid sequence, the replaced nucleic acid sequence is or comprises a rodent sequence (e.g., a mouse or rat sequence). The nucleic acid sequence so placed may include one or more regulatory sequences that are part of source nucleic acid sequence used to obtain the sequence so placed (e.g., promoters, enhancers, 5'- or 3'-untranslated regions, etc.). For example, in various embodiments, the replacement is a substitution of an endogenous sequence with a heterologous sequence that results in the production of a gene product from the nucleic acid sequence so placed (comprising the heterologous sequence), but not expression of the endogenous sequence; the replacement is of an endogenous genomic sequence with a nucleic acid sequence that encodes a protein that has a similar function as a protein encoded by the endogenous sequence (e.g., the endogenous genomic sequence encodes a CD47 protein, and the DNA fragment encodes one or more human CD47 proteins). In various embodiments, an endogenous gene or fragment thereof is replaced with a corresponding human gene or fragment thereof. A corresponding human gene or fragment thereof is a human gene or fragment that is an ortholog of, or is substantially similar or the same in structure and/or function, as the endogenous gene or fragment thereof that is replaced.

The phrase "cluster of differentiation 47protein" or "CD47protein", as used herein, refers to a multi-pass transmembrane protein that belongs to the immunoglobulin superfamily and has an extracellular amino-terminal immunoglobulin V domain, five transmembrane domains and a short carboxyl-terminal intracellular tail. CD47 is expressed on the cell surface and is involved in interactions between membrane surface proteins such as, for example, integrins, SIRPα and thrombospondin-1 (TSP-1). CD47 is expressed in normal tissues and up-regulated in many human cancers. CD47 has been shown to be involved in several cellular processes such as, for example, apoptosis, proliferation, adhesion and migration. Several alternatively spliced CD47 isoforms have been identified between mouse and man. By way of illustration, nucleotide and amino acid sequences of mouse and human CD47 genes are provided in Table 3. Persons of skill upon reading this disclosure will recognize that one or more endogenous CD47 genes in a genome (or all) can be replaced by one or more heterologous CD47 genes (e.g., polymorphic variants, subtypes or mutants, genes from another species, humanized forms, etc.).

A "CD47-expressing cell", as used herein, refers to a cell that expresses a CD47 transmembrane protein. In some embodiments, a CD47-expressing cell expresses a CD47 transmembrane protein on its surface. In some embodiments, a CD47 protein expressed on the surface of the cell in an amount sufficient to mediate cell-to-cell interactions via the CD47 transmembrane protein expressed on the surface of the cell. Exemplary CD47-expressing cells include neurons, immune cells, keratinocytes, and circulating cells. CD47-expressing cells regulate the interaction of immune cells and circulating cells to regulate various cellular processes such as adhesion, cell proliferation and/or apoptosis, angiogenesis and inflammation. In some embodiments, non-human animals of the present invention demonstrate regulation of various cellular processes (as described herein) via humanized CD47 proteins expressed on the surface of one more cells of the non-human animal.

The term "reference" is used herein to describe a standard or control agent, cohort, individual, population, sample, sequence or value against which an agent, animal, cohort, individual, population, sample, sequence or value of interest is compared. In some embodiments, a reference agent, cohort, individual, population, sample, sequence or value is tested and/or determined substantially simultaneously with the testing or determination of the agent, cohort, individual, population, sample, sequence or value of interest. In some embodiments, a reference agent, cohort, individual, population, sample, sequence or value is a historical reference, optionally embodied in a tangible medium. In some embodiments, a reference may refer to a control. As used herein, a "reference" may refer to a "reference animal". A "reference animal" may have a modification as described herein, a modification that is different as described herein or no modification (i.e., a wild-type animal). Typically, as would be understood by those skilled in the art, a reference agent, animal, cohort, individual, population, sample, sequence or value is determined or characterized under conditions comparable to those utilized to determine or characterize the agent, animal (e.g., a mammal), cohort, individual, population, sample, sequence or value of interest.

The term "substantially", as used herein, refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The phrase "substantial homology", as used herein, refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized in Table 1 and 2.

TABLE 1

| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gin | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.7 |

TABLE 2

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al. (1990) Basic local alignment search tool, *J. Mol. Biol.,* 215(3): 403-410; Altschul et al. (1997) *Methods in Enzymology*; Altschul et al., "Gapped BLAST and PSI-BLAST: anew generation of protein database search programs", *Nucleic Acids Res.* 25-3389-3402; Baxevanis et al. (1998) Bioinformatics: APractical Guide to the Analysis of Genes and Proteins, Wiley; and Misener et al. (eds.) (1999) Bioinformatics Methods and Protocols (*Methods in Molecular Biology*, Vol. 132), Humana Press. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence. In some embodiments, the relevant stretch is at least 10, 15, 20, 25, 30, 35, 40, 45, 50, or more residues.

The phrase "substantial identity", as used herein, refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al. (1990) Basic local alignment search tool, *J. Mol. Biol.*, 215(3): 403-410; Altschul et al., *Methods in Enzymology*; Altschul et al. (1997), *Nucleic Acids Res.* 25:3389-3402; Baxevanis et al. (1998) Bioinformatics: A Practical Guide to the Analysis of Genes and Proteins, Wiley; and Misener et al., (eds.) (1999) Bioinformatics Methods and Protocols (*Methods in Molecular Biology*, Vol. 132), Humana Press. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, or more residues.

The phrase "targeting vector" or "targeting construct", as used herein, refers to a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., loxP or Frt sites) are also included. In some embodiments, a targeting construct of the present invention further comprises a nucleic acid sequence or gene of particular interest, a selectable marker, control and or regulatory sequences, and other nucleic acid sequences that allow for recombination mediated through exogenous addition of proteins that aid in or facilitate recombination involving such sequences. In some embodiments, a targeting construct of the present invention further comprises a gene of interest in whole or in part, wherein the gene of interest is a heterologous gene that encodes a protein, in whole or in part, that has a similar function as a protein encoded by an endogenous sequence. In some embodiments, a targeting construct of the present invention further comprises a humanized gene of interest, in whole or in part, wherein the humanized gene of interest encodes a protein, in whole or in part, that has a similar function as a protein encoded by the endogenous sequence.

The term "variant", as used herein, refers to an entity that shows significant structural identity with a reference entity, but differs structurally from the reference entity in the presence or level of one or more chemical moieties as compared with the reference entity. In many embodiments, a "variant" also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A "variant", by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs. double, E vs. Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a "variant polypeptide" may differ from a reference polypeptide as a result of one or more differences in amino acid sequence and/or one or more differences in chemical moieties (e.g., carbohydrates, lipids, etc.) covalently attached to the polypeptide backbone. In some embodiments, a "variant polypeptide" shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a "variant polypeptide" does not share at least one characteristic sequence element with a reference polypeptide. In some embodiments, the reference polypeptide has one or more biological activities. In some embodiments, a "variant polypeptide" shares one or more of the biological activities of the reference polypeptide. In some embodiments, a "variant polypeptide" lacks one or more of the biological activities of the reference polypeptide. In some embodiments, a "variant polypeptide" shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a "variant" has 10, 9, 8, 7, 6, 5, 4, 3, 2, or 1 substituted residue as compared with a parent. Often, a "variant" has a very small number (e.g., fewer than 5, 4, 3, 2, or 1) number of substituted functional residues (i.e., residues that participate in a particular biological activity). Furthermore, a "variant" typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

The term "vector", as used herein, refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

The term "wild-type", as used herein, has its art-understood meaning that refers to an entity having a structure and/or activity as found in nature in a "normal" (as contrasted with mutant, diseased, altered, etc.) state or context. Those of ordinary skill in the art will appreciate that wild-type genes and polypeptides often exist in multiple different forms (e.g., alleles).

DETAILED DESCRIPTION OF CERTAIN EMBODIMENTS

The present invention provides, among other things, improved and/or engineered non-human animals having humanized genetic material encoding a cluster of differentiation 47 (CD47) gene for determining the therapeutic efficacy of CD47 antagonists (e.g., an anti-CD47 antibody) for the treatment of cancer, and assays in transplant engraftment, activation and phagocytosis and signal transduction. It is contemplated that such non-human animals provide an improvement in determining the therapeutic efficacy of CD47 antagonists and their potential for CD47 blockade. It is also contemplated that such non-human animals provide an improvement in transplant engraftment of human cells. Therefore, the present invention is particularly useful for the development of anti-CD47 therapies for the treatment of various cancers, as well as for maintaining human hematopoietic cells in non-human animals. In particular, the present invention encompasses the humanization of a murine CD47 gene resulting in expression of a humanized CD47 protein on the surface of cells of the non-human animal. Such humanized CD47 proteins have the capacity to provide a source of human CD47 cells for determining the efficacy of anti-CD47 therapeutics to activate phagocytosis of tumor cells. Further, such humanized CD47 proteins have the capacity to recognize engrafted human cells via engagement of other cell surface proteins and ligands present on the surface of the engrafted human cells (e.g., SIRPα). In some embodiments, non-human animals of the present invention are capable of activating phagocytosis via blockade of CD47 signaling through the humanized CD47 protein expressed on the surface of cells of the non-human animal. In some embodiments, non-human animals of the present invention are capable of receiving transplanted human hematopoietic cells; in some embodiments, such non-human mammals develop and/or have an immune system comprising human cells. In some embodiments, humanized CD47 proteins have a sequence corresponding to the N-terminal immunoglobulin V domain of a human CD47 protein. In some embodiments, humanized CD47 proteins have a sequence corresponding to an N-terminal portion of a human CD47 protein that comprises an extracellular portion and a transmembrane portion of a human CD47 protein, wherein the extracellular portion includes the N-terminal immunoglobulin V domain of the human CD47 protein and the transmembrane portion includes the five transmembrane domains of the human CD47 protein. In some embodiments, humanized CD47 proteins have a sequence corresponding to the intracytoplasmic tail of a non-human (e.g., murine) CD47 protein. In some embodiments, humanized CD47 proteins have a sequence corresponding to amino acid residues 19-292 (or 19-141, or 19-127) of a human CD47 protein. In some embodiments, non-human animals of the present invention comprise an endogenous CD47 gene that contains genetic material from the non-human animal and a heterologous species (e.g., a human). In some embodiments, non-human animals of the present invention comprise a humanized CD47 gene, wherein the humanized CD47 gene comprises exons of a human CD47 gene that encode an extracellular portion including the N-terminal immunoglobulin V domain of a human CD47 gene. In some embodiments, the humanized CD47 gene comprises human CD47 exons, e.g., exons 2-7, encoding an N-terminal portion of a human CD47 protein that comprises an extracellular portion and a transmembrane portion of a human CD47 protein, wherein the extracellular portion includes the N-terminal immunoglobulin V domain of the human CD47 protein and the transmembrane portion includes the five transmembrane domains of the human CD47 protein. In some embodiments, the humanized CD47 gene comprises non-human CD47 exons that encode the signal peptide, in whole or in part, and the intracytoplasmic tail of a non-human CD47 protein. In some embodiments, the humanized CD47 gene comprises non-human CD47 exon 1 and exon(s) downstream of exon 7 that encode the intracytoplasmic tail and the 3' UTR. Depending on the isoforms, there may be one or more exons downstream of exon 7, with the stop codon and the 3' UTR being present in the last exon for all isoforms. For example, isoform 2 of both mouse and human CD47 shown in Table 3 have two exons downstream of exon 7, designated as exon 8 and 9.

Various aspects of the invention are described in detail in the following sections. The use of sections is not meant to limit the invention. Each section can apply to any aspect of the invention. In this application, the use of "or" means "and/or" unless stated otherwise.

Cluster of Differentiation 47 (CD47) Gene

CD47, originally named integrin-associated protein (IAP) for its role in signal transduction from integrins on immune cells, is a transmembrane protein that includes an N-terminal immunoglobulin V (IgV) domain, five transmembrane domains, and a short C-terminal intracytoplasmic tail. The intracytoplasmic tail differs in length according to four alternatively spliced isoforms that have been identified. CD47 (or IAP) was initially described as being expressed on all tissues (isoform 2), neurons (isoform 4) and keratinocytes and macrophages (isoform 1; see Reinhold et al. (1995) *J. Cell Sci.* 108:3419-3425). Little is known about isoform 3 despite this form having the second longest intracytoplasmic tail among the four isoforms. In addition to integrins, CD47 is known to interact with several other cell surface proteins such as, for example, thrombospondin and members of the SIRP family. Most notably, CD47 interacts with SIRPα and leads to bidirectional signaling that regulates a variety of cell-to-cell responses such as, for example, inhibition of phagocytosis and T cell activation. Indeed, CD47-SIRPα interaction has come into focus in recent years for its role in providing tumor cells with the capacity to evade immune surveillance. CD47 binding to SIRPα normally provides protection through anti-phagocytic signals ("don't eat me") for normal cells. However, it has been discovered that tumors also express anti-phagocytic signals, including CD47, to evade destruction by phagocytosis. Interestingly, CD47 is known to be upregulated in several hematologic cancers and contribute to both the growth and dissemination of tumors (Chao et al. (2012) *Curr Opin Immunol.* 24(2): 225-232).

The complete effects of targeting CD47 and the CD47-SIRPα pathway as a new treatment for cancer are unknown and some possible toxicities have been explored. A more thorough and detailed understanding of CD47 signaling and the CD47-SIRPα pathway is needed to develop better targeted therapies for cancer treatment of the future.

CD47 Sequences

Exemplary CD47 sequences for mouse and human are set forth in Table 3. For mRNA sequences, bold font indicates coding sequence, and consecutive exons, where indicated, are separated by alternating underlined text. For mouse and human protein sequences, signal peptides are underlined, extracellular sequences are bold font and intracytoplasmic sequences are italicized. For humanized protein sequences, non-human sequences are indicated in regular font, human sequences are indicated in bold font, and signal peptides are underlined. As shown, the isoforms differ in the number of exons. For example, isoforms 1-4 of the human CD47 gene have a total of 8, 9, 10 and 11 exons, respectively, with exons 2-7 of each isoform encoding the extracellular domain and the five transmembrane domains.

TABLE 3

```
Mouse CD47 mRNA isoform 1 (XM_006521810.1)
GCCTACACCGGGAGAGCAGGGAGGAGGAGTTGGACTGAGGTTGGGCGGCTC
CGAGGTCCAGGGCGAGCTTGGCCAGAGGGAGTAGAGAGCAGCGGGGCTGC
GCAGGGACGCGTGCCGTGAGTTCCGGTGAGCGTGTGTGTCCCATGCTCCCGT
CTTTCAGGCCGGCCCAGGACACGAAGCGGAAGAGAGCTGGCTGGAGGGAC
GGGGGCCGTGAGCAGAGAGTGCAACCCGCGCAGCCCCGGGGACAGGCTGA
TTCTTGGCGCTCTCCGCCGGAGCCTGCCCAGGGCTGGGTGTGAGGCTGGCGT
CACGTCAACGAGCAGAGGCGGCCAGGCGGGGCGGAGTGCGCGTGCGCGGG
GCGGCGAGCACGCGCGCGCGCGCACCCCCGGGCAGCCTGGGCGGCCGCTCC
TGCCTGTCACTGCTGCGGCGCTGCTGGTCGGTCGTTTCCCTTGAAGGCAGCA
GCGGAGGCGGCGGCTGCTCCAGACACCTGCGGCGGCGACCCCCCGGCGGCG
CGGAGATGTGGCCCTTGGCGGCGGCGCTGTTGCTGGGCTCCTGCTGCT
GCGGTTCAGCTCAACTACTGTTTAGTAACGTCAACTCCATAGAGTTCAC
TTCATGCAATGAAACTGTGGTCATCCCTTGCATCGTCCGTAATGTGGAG
GCGCAAAGCACCGAAGAAATGTTTGTGAAGTGGAAGTTGAACAAATCG
TATATTTTCATCTATGATGGAAATAAAAATAGCACTACTACAGATCAAA
ACTTTTACCAGTGCAAAAATCTCAGTCTCAGACTTAATCAATGGCATTGC
CTCTTTGAAAATGGATAAGCGCGATGCCATGGTGGGAAACTACACTTGC
GAAGTGACAGAGTTATCCAGAGAAGGCAAAACAGTTATAGAGCTGAAA
AACCGCACGGCCTTCAACACTGACCAAGGATCAGCCTGTTCTTACGAGG
AGGAGAAAGGAGGTTGCAAATTAGTTTCGTGGTTTTCTCCAAATGAAAA
GATCCTCATTGTTATTTTCCCAATTTTGGCTATACTCCTGTTCTGGGGAA
AGTTTGGTATTTTAACACTCAAATATAAATCCAGCCATACGAATAAGAG
AATCATTCTGCTGCTCGTTGCCGGGCTGGTGCTCACAGTCATCGTGGTT
GTTGGAGCCATCCTTCTCATCCCAGGAGAAAAGCCCGTGAAGAATGCTT
CTGGACTTGGCCTCATTGTAATCTCTACGGGGATATTAATACTACTTCA
GTACAATGTGTTTATGACAGCTTTTGGAATGACCTCTTTCACCATTGCC
ATATTGATCACTCAAGTGCTGGGCTACGTCCTTGCTTTGGTCGGGCTGT
GTCTCTGCATCATGGCATGTGAGCCAGTGCACGGCCCCCTTTTGATTTC
AGGTTTGGGGATCATAGCTCTAGCAGAACTACTTGGATTAGTTTATATG
AAGTTTGTCGAATAGGTGAAGGGAAGTGACGGACTGTAACTTGGAAGTCA
GAAATGGAAGAATACAGTTGTCTAAGCACCAGGTCTTCACGACTCACAGCT
GGAAGGAACAGACAACAGTAACTGACTTCCATCCAGGAAAACATGTCACAT
AAATGATTACTAAGTTTATATTCAAAGCAGCTGTACTTTACATAATAAAAAA
AATATGATGTGCTGTGTAACCAATTGGAATCCCATTTTTCTATTGTTTCTACT
CAACTAGGGGCAAACGTTTCAGGGGCAACTTCCAAGAATGATGCTTGTTAG
ATCCTAGAGTCTCTGAACACTGAGTTTAAATTGATTCCGAGTGAGACTCGCC
AAGCACTAACCTGAGGGTTAGTTACCCAGAGATACCTATGAAAAACAGTGG
TATCCAGCAAGCCTTAGTAAACTCAGGTTGCCAGCAGCTTTGCCACTTCCGC
TGCTAGCTGAATAACAAGACTGCCACTTCTGGGTCATAGTGATAGAGACTG
AAGTAGAAAAACGAATGTGGTTGGGCAAATCCCGTGTGGCCCCTCTGTGTG
CTATGATATTGATGGCACTGGTGTCTTCATTCTTGGGGGTTGCCATCATTCAC
ACACACCCCTTTGACATACAGTGCACCCCAGTTTTGAATACATTTTTTTTGCA
CCCTGTCCCGTTCTGCTACTTTGATTTGCGTTATGATATATATATATATATAT
AATACCTTTTCTCCTCTTTAAACATGGTCCTGTGACACAATAGTCAGTTGCA
GAAAGGAGCCAGACTTATTCGCAAAGCACTGTGCTCAAACTCTTCAGAAAA
AAAGGAAAAAAAAAAAAGCTATAGTTGTAACATATGTATTCCAGACCTCT
GGTTTAAAGGCAAAAGAAAAAAATCTACAGTGTTTCTTCTCATGTTTTCTG
ATCGGAGGCATGACAAAGCAAGACTGAAATCTGAACTGTGTCTCCTGCATG
GCAACACGTGTCTCCGTCAGGCCCTCGCAAGGCCCGGGGAGGGGGTTCTAC
GCCTCTTGTCTCTTTGTTGCATGCTGAACACTCATCGCCTTCCTACTGTATCC
TGCCTCCTGCAGCCTCCCTCTTCCTCCTCCTCTTCCTCTTCCTCCTCTTCCTCC
TCCTCCTCCTCTTCCTCCAAGTTTGAAAGGTCAAACAAAACTACCACATTCC
CTACCCAGTTAGAAGAAAACCACCGTCCTGACAGTTGTGATCGCATGGAGT
ACTTTTAGATTATTAGCACCTGTTTTTACCTCGTTTGTGGGCGTGTTTGTATG
TGCACATGTATGAAGTCGGCACATGCACCTTCTGTATGGGCAGAGGCGTGG
CATCTACAGAAGAGCAGATGCCAACTTTGTGCTTTTAGTGAATACATTAAAA
AAAAAAAACCAACGGTCCTTATTGAGTGGAATTCTATTTGATGCAAATATTT
GAGCTCTTTAAGACTTTAAAACTAGATAATGTGCCAAGCTTTTAGGACTGCT
CACCAGTGCCCTCTGAAGAAACACCAGTACTTTTTCCTGTTTGTGTAATAAA
```

TABLE 3-continued

```
GGCATATTTGTATTTGTGTTTGCATCACTAATGGTTATTTCTTCTTAGTCCAC
TGAATGTTTCCATGTGCCTCTCGTATGCCAAACTTTTTGTCATCTTTCATGTG
GGGACCAAATGGTTTGTCTGTGGCAAACCTAAACCTATGACCTGCTGAGGCC
TCTCAGAAAACTGACCACAGTACCAAGATAGTACTTCGCAAAGAAAAGTAG
GTTCCCTCCCTGGTTTTGTAGCTGTCGCCAATATTAGCGTAATTCCAAGGAG
CTGAACGCCTTTATATAAATCTGATGGCACCTGATGCTTTTAGTTCTGAAAA
TATTTACACTCGGATCATGTTGTTGATGACTTAAACAAAGTTTTGATGAAGA
GAGCAAAAAAAAAGCAGGTGGATTTGGAACAGTTTCAGGGTTTTTTTTGTTT
TTTGTTTTTTGTTTTTGTTTTTTTTTTTTATTTTTGTTTTTCTGTTCTCTGTTAG
AAAAGTCAGGTGTTCTCTGTCAGGCTATCTTTATAGTCAATTTTTTTTACGAA
CTAAAGTAGTACCTTTTAATATGTAGTCAACGCCCCTCTGCTCGGGGTTCAG
TTTTGGGTCTTAACCAGCTGTCATGTTCTCTATGCTGCCTGCCACTTGAGGCA
CTGAGTGCCCTAGACAGTCCCATCGGTGGTAGCCAGGGAAACGAAAGACGA
ACTCAACTCTTGCTCCTAATAATCAACTCTCTGTATGAAGGATGGCAGCATT
AAGAGTCCTCCTGCCTGGGCATTATTGGGCCAGTTCACCCTCTTTAAATCAA
ACCCGCAGTGGCTCCCAGTTCTCGTCCCATCAGATTTAAATTGCTAACAGTA
TGGGGGGCACCACGCATCTGTTTTGTCCCACAATGCGCTTTTCTCTCCCAAA
TCCCGATTTCTGCTGTCATAGCCTCTATTCAATTTTTATTTATTGTCTGCCCTC
CACTTATACAATCGTAGAGAGCAATGCCATTTGTCACTTTCTGCAACAGTTT
TTTGAGCCTTTATGGCTGAATCCCATTTTTCTTCTCTTTCAAACTGTTTGCTCC
ATTGCTCCTCCCGCACGGCTGTCCGTACAGTCATCCCATCCATCTGGGGGCC
TCTTTCATCTCTCACCCTTCCTGGTGCTTCGTGGATCTCTGCTTACCTCTGTG
GGTTTTTTTTTTTTTTTGACTTATTCTTCTCACTGGACTTTAAGATTACTTC
CACAGCGAAAGTGCTGCCTCCCTTTTCTGCCCGCAGTGTTCTGCGTACTTTA
GATACTACTCAGTGCTGACATTTGATGGCAAAAGTTGCCTGCACTTAAATTT
CTCTTTTTAATAGGGTGAACTAGAGTTGGAGTTTTTTTCTCTTTTTTCTCTTTT
CTCTCTCTCTCTCTCTCTCTCTCTCTCTCTCTCTCTCTCCCTCCCTCCCTC
CCTCCCTCCCTCCCTCTCTCTCTCTTTTCTTTCTTTCTTTCTTTCT
TTCTTTCTTTCTTTCTTTCTTTCTTTTTTGACAAATCTCACAGGCTTTGA
GAATTATAAAAGGTGACAGTTCACCTGAAAATCACAGGTCTGGTCTGTTTAA
ATTGTTGAGAAATATCCGATTAAAAGTCTTGTGGCTGTGTCCTAATAGGCTC
TCTTTCAGGACGTTGTAGTCAATAGAGTGGCTGAACCATACTTGAGTTTATA
AAGCTCAAAAACTGATGCACCCACTCTGCTATTATCGTGTTAGTAAGAGTTC
AGCTGTATATCATTGTCTAGGTTTATCTTGTCCTACAGTGGGTATTCAAATAT
GGCCACCAGAGGATATGTGTAAATATAAGCACCTGTATTTGCCTGTTGTTGA
GAACTGGAGGGAAAACAAAAAATGTCTGGCAACCCTTTGCCTTTTTAACCGT
AATTAATTGACAGTTTATTTAGAGATAAGAGTTTTCAAAAATCTCTTAACTG
CCACAACCCACAGAGGGTCTTGTTTTGCCATCTTCAGTGGCTCACAGATATG
ATCCAAGTTAACTTGAAAGAGATGAGCAGTACCCAGGAAATTGTCCTGCCTT
TAACTCTGGCTGTCCTTAATTATGACTGTTTAATGCTGAATTTTCCATCCGTC
TAGTGTTTGAGGGTAAAGAAAAGCCTTTTTTAAATAAGTATTTCTGTAAAAC
GGCATCGGTGGGATCTTCTGTGTTGCTATCACGGGTGAAAGAGGGAAACAT
TTCTTATTTTTATTAAGCAGAGCATTATTTACAGAAAGCCATTGTTGAGAATT
AGTTCCCACATCATATAAATATCCATTAACCATTCTAAATTGTAAGAGAACT
CCAGTGTTGCTATGCACAAGGAACTCTCCTGGGGCCTTTTTTTGCATAGCA
ATTAAAGGTATGCTATTTGTCAGTAGCCATTTTTTGCAGTGATTTAAAGACC
AAAGTTGTTTTACAGCTGTGTTACCCTTAAAGGTTTTTTTTTTATGTATTAAA
TCAATTTATCACTGTTTGAAGCTTTGAATACCTGCAATCTTTGCCAAGATACT
TTTTTATTTAAAAAAATAACTGTGTAAATATTACCCTGTAATATTATATATAC
TTAATAAAACATTTTAAGCTA (SEQ ID NO: 1)
```

Mouse CD47 amino acid isoform 1 (XP_006521873.1)
MWPLAAALLLGSCCCGSAQLLFSNVNSIEFTSCNETVVIPCIVRNVEAQSTEE
MFVKWKLNKSYIFIYDGNKNSTTTDQNFTSAKISVSDLINGIASLKMDKRDA
MVGNYTCEVTELSREGKTVIELKNRTAFNTDQGSACSYEEEKGGCKLVSW
FSPNEKILIVIFPILAILLFWGKFGILTLKYKSSHTNKRIILLLVAGLVLTVIVVVG
AILLIPGEKPVKNASGLGLIVISTGILILLQYNVFMTAFGMTSFTIAILITQVLGYV
LALVGLCLCIMACEPVHGPLLISGLGIIALAELLGLVYMKFVE (SEQ ID NO: 2)

Mouse CD47 mRNA isoform 2 (XM_006521811.1)
```
GCCTACACCGGGAGAGCAGGGAGGAGGAGTTGGACTGAGGTTGGGCGGCTC
CGAGGTCCAGGGCGAGCTTGGCCAGAGGGAGTAGAGAGCAGCGGGGCTGC
GCAGGGACGCGTGCCGTGAGTTCCGGTGAGCGTGTGTGCCCATGCTCCCGT
CTTTCAGGCCGGCCCAGGACACGAAGCCGGAAGAGAGCTGGCTGGAGGGAC
GGGGGCCGTGAGCAGAGAGTGCAACCCGCGCAGCCCCGGGGACAGGCTGA
TTCTTGGCGCTCTCCGCCGGAGCCTGCCCAGGGCTGGGTGTGAGGCTGGCGT
CACGTCAACGAGCAGAGGCGGCCAGGCGGGGCGGAGTGCGCGTGCGCGGG
GCGGCGAGCACGCGCGCGCGCACCCCCGGGCAGCCTGGGCGGCCGCTCC
TGCCTGTCACTGCTGCGGCGCTGCTGGTCGGTCGTTTCCCTTGAAGGCAGCA
GCGGAGGCGGCGGCTGCTCCAGACACCTGCGGCGGCGACCCCCCGGCGGCG
CGGAG**ATGTGGCCCTTGGCGGCGGCGCTGTTGCTGGGCTCCTGCTGCT
GCGGTTCAGCTCAACTACTGTTTAGTAACGTCAACTCCATAGAGTTCAC
TTCATGCAATGAAACTGTGGTCATCCCTTGCATCGTCCGTAATGTGGAG
GCGCAAAGCACCGAAGAAATGTTTGTGAAGTGGAAGTTGAACAAATCG
TATATTTTCATCTATGATGGAAATAAAAATAGCACTACTACAGATCAAA
ACTTTACCAGTGGAAAAATCTCAGTCTCAGACTTAATCAATGGCATTGC
CTCTTTGAAAATGGATAAGCGCGATGCCATGGTGGGAAACTACACTTGC
GAAGTGACAGAGTTATCCGAGAAGGCAAAACAGTTATAGAGCTGAAA
AACCGCACGGTTTCGTGGTTTTCTCCAAATGAAAAGATCCTCATTGTTA
TTTTCCCAATTTTGGCTATACTCCTGTTCTGGGGAAAGTTTGGTATTTA**
```

TABLE 3-continued

```
ACACTCAAATATAAATCCAGCCATACGAATAAGAGAATCATTCTGCTGC
TCGTTGCCGGGCTGGTGCTCACAGTCATCGTGGTTGTTGGAGCCATCCT
TCTCATCCCAGGAGAAAAGCCCGTGAAGAATGCTTCTGGACTTGGCCTC
ATTGTAATCTCTACGGGGATATTAATACTACTTCAGTACAATGTGTTTAT
GACAGCTTTTGGAATGACCTCTTTCACCATTGCCATATTGATCACTCAA
GTGCTGGGCTACGTCCTTGCTTTGGTCGGGCTGTGTCTCTGCATCATGG
CATGTGAGCCAGTGCACGGCCCCCTTTTGATTTCAGGTTTGGGGATCAT
AGCTCTAGCAGAACTACTTGGATTAGTTTATATGAAGTTTGTCGCTTCC
AACCAGAGGACTATCCAACCTCCTAGGAATAGGTGAAGGGAAGTGACGG
ACTGTAACTTGGAAGTCAGAAATGGAAGAATACAGTTGTCTAAGGACCAGG
TCTTCACGACTCACAGCTGGAAGGAACAGACAACAGTAACTGACTTCCATC
CAGGAAAACATGTCACATAAATGATTACTAAGTTTATATTCAAAGCAGCTGT
ACTTTACATAATAAAAAAAATATGATGTGCTGTGTAACCAATTGGAATCCCA
TTTTTCTATTGTTTCTACTCAACTAGGGGCAAACGTTTCAGGGGCAACTTCCA
AGAATGATGCTTGTTAGATCCTAGAGTCTCTGAACACTGAGTTTAAATTGAT
TCCGAGTGAGACTCGCCAAGCACTAACCTGAGGGTTAGTTACCCAGAGATA
CCTATGAAAACAGTGGTATCCAGCAAGCCTTAGTAAACTCAGGTTGCCAG
CAGCTTTGCCACTTCCGCTGCTAGCTGAATAACAAGACTGCCACTTCTGGGT
CATAGTGATAGAGACTGAAGTAGAAAAACGAATGTGGTTGGGCAAATCCCG
TGTGGCCCCTCTGTGTGCTATGATATTGATGGCACTGGTGTCTTCATTCTTGG
GGGTTGCCATCATTCACACACACCCCTTTGACATACAGTGCACCCCAGTTTT
GAATACATTTTTTTTGCACCCTGTCCCGTTCTGCTACTTTGATTTGCGTTATG
ATATATATATATATATATAATACCTTTTCTCCTCTTTAAACATGGTCCTGTGA
CACAATAGTCAGTTGCAGAAAGGAGCCAGACTTATTCGCAAAGCACTGTGC
TCAAACTCTTCAGAAAAAAAGGAAAAAAAAAAAAAAGCTATAGTTGTAACAT
ATGTATTCCAGACCTCTGGTTTAAAGGCAAAAGAAAAAAAAATCTACAGTGT
TTCTTCTCATGTTTTCTGATCGGAGGCATGACAAAGCAAGACTGAAATCTGA
ACTGTGTCTCCTGCATGGCAACACGTGTCTCCGTCAGGCCCTCGCAAGGCCC
GGGGAGGGGGTTCTACGCCTCTTGTCTCTTTGTTGCATGCTGAACACTCATC
GCCTTCCTACTGTATCCTGCCTCCTGCAGCCTCCCTCTTCCTCCTCCTCTTCCT
CTTCCTCCTCTTCCTCCTCCTCCTCTTCCTCCAAGTTTGAAAGGTCAAAC
AAAACTACCACATTCCCTACCCAGTTAGAAGAAAACCACCGTCCTGACAGTT
GTGATCGCATGGAGTACTTTTAGATTATTAGCACCTGTTTTTACCTCGTTTGT
GGGCGTGTTTGTATGTGCACATGTATGAAGTCGGCACATGCACCTTCTGTAT
GGGCAGAGGCGTGGCATCTACAGAAGAGCAGATGCCAACTTTGTGCTTTTA
GTGAATACATTAAAAAAAAAAAAACCAACGGTCCTTATTGAGTGGAATTCTA
TTTGATGCAAATATTTGAGCTCTTTAAGACTTTAAAACTAGATAATGTGCCA
AGCTTTTAGGACTGCTCACCAGTGCCCTCTGAAGAAACACCAGTACTTTTTC
CTGTTTGTGTAATAAAGGCATATTTGTATTTGTGTTTGCATCACTAATGGTTA
TTTCTTCTTAGTCCACTGAATGTTTCCATGTGCCTCTCGTATGCCAAACTTTT
TGTCATCTTTCATGTGGGGACCAAATGGTTTGTCTGTGGCAAACCTAAACCT
ATGACCTGCTGAGGCCTCTCAGAAAACTGACCACAGTACCAAGATAGTACT
TCGCAAAGAAAAGTAGGTTCCCTCCCTGGTTTTGTAGCTGTCGCCAATATTA
GCGTAATTCCAAGGAGCTGAACGCTTTATATAAATCTGATGGCACCTGATG
CTTTTAGTTCTGAAAATATTTACACTCGGATCATGTTGTTGATGACTTAAACA
AAGTTTTGATGAAGAGAGCAAAAAAAAAAGCAGGTGGATTTGGAACAGTTTC
AGGGTTTTTTTTGTTTTTTGTTTTTGTTTTTGTTTTTTTTTTTATTTTTGTTT
TTCTGTTCTCTGTTAGAAAAGTCAGGTGTTCTCTGTCAGGCTATCTTTATAGT
CAATTTTTTTACGAACTAAAGTAGTACCTTTTAATATGTAGTCAACGCCCCT
CTGCTCGGGGTTCAGTTTTGGGTCTTAACCAGCTGTCATGTTCTCTATGCTGC
CTGCCACTTGAGGCACTGAGTGCCCTAGACAGTCCCATCGGTGGTAGCCAG
GGAAACGAAAGACGAACTCAACTCTTGCTGCTAATAATCAACTCTCTGTATG
AAGGATGGCAGCATTAAGAGTCCTCCTGCCTGGGCATTATTGGGCCAGTTCA
CCCTCTTTAAATCAAACCCGCAGTGGCTCCCAGTTCTCGTCCCATCAGATTT
AAATTGCTAACAGTATGGGGGCACCACGCATCTGTTTTGTCCCACAATGCG
CTTTTCTCTCCCAAATCCCGATTTCTGCTGTCATAGCCTCTATTCAATTTTAT
TTATTGTCTGCCCTCCACTTATACAATCGTAGAGAGCAATGCCATTTGTCACT
TTCTGCAACAGTTTTTTGAGCCTTTATGGCTGAATCCCATTTTTCTTCTCTTTC
AAACTGTTTGCTCCATTGCTCCTCCCGCACGGCTGTCCGTACAGTCATCCCAT
CCATCTGGGGGCCTCTTTCATCTCTCACCCTTCCTGGTGCTTCGTGGATCTCT
GCTTACCTCTGTGGGTTTTTTTTTTTTTTTTGACTTATTCTTCTCACTGGACT
TTAAGATTACTTCCACAGCGAAAGTGCTGCCTCCCTTTTCTGCCCGCAGTGTT
CTGCGTACTTTAGATACTACTCAGTGCTGACATTTGATGGCAAAAGTTGCCT
GCACTTAAATTTCTCTTTTTAATAGGGTGAACTAGAGTTGGAGTTTTTTCTC
TTTTTTCTCTTTTCTCTCTCTCTCTCTCTCTCTCTCTCTCTCTCTCTCTCTCT
CCCTCCCTCCCTCCCTCCCTCCCTCCCTCTCTCTCTTTTTCTTTCTTTC
TTTCTTTCTTTCTTTCTTTCTTTCTTTCTTTCTTTTTTTGACAAATCT
CACAGGCTTTGAGAATTATAAAAGGTGACAGTTCACCTGAAAATCACAGGT
CTGGTCTGTTTAAATTGTTGAGAAATATCCGATTAAAGTCTTGTGGCTGTG
TCCTAATAGGCTCTCTTTCAGGACGTTGTAGTCAATAGAGTGGCTGAACCAT
ACTTGAGTTTATAAAGCTCAAAAACTGATGCACCCACTCTGCTATTATCGTG
TTAGTAAGAGTTCAGCTGTATATCATTGTCTAGGTTTATCTTGTCCTACAGTG
GGTATTCAAATATGGCCACCAGAGGATATGTGTAAATATAAGCACCTGTATT
TGCCTGTTGTTGAGAACTGGAGGGAAAACAAAAAATGTCTGGCAACCCTTT
GCCTTTTTAACCGTAATTAATTGACAGTTTATTTAGAGATAAGAGTTTTCAA
AAATCTCTTAACTGCCACAACCCACAGAGGGTCTTGTTTTGCCATCTTCAGT
GGCTCACAGATATGATCCAAGTTAACTTGAAAGAGATGAGCAGTACCCAGG
AAATTGTCCTGCCTTTAACTCTGGCTGTCCTTAATTATGACTGTTTAATGCTG
AATTTTCCATCCGTCTAGTGTTTGAGGGTAAAGAAAAGCCTTTTTTAAATAA
GTATTTCTGTAAAACGGCATCGGTGGGATCTTCTGTGTTGCTATCACGGGTG
```

TABLE 3-continued

AAAGAGGGAAACATTTCTTATTTTTATTAAGCAGAGCATTATTTACAGAAAG
CCATTGTTGAGAATTAGTTCCCACATCATATAAATATCCATTAACCATTCTA
AATTGTAAGAGAACTCCAGTGTTGCTATGCACAAGGAACTCTCCTGGGGGC
CTTTTTTTGCATAGCAATTAAAGGTATGCTATTTGTCAGTAGCCATTTTTTGC
AGTGATTTAAAGACCAAAGTTGTTTTACAGCTGTGTTACCCTTAAAGGTTTT
TTTTTTATGTATTAAATCAATTTATCACTGTTTGAAGCTTTGAATACCTGCAA
TCTTTGCCAAGATACTTTTTTATTTAAAAAAATAACTGTGTAAATATTACCCT
GTAATATTATATATACTTAATAAAACATTTTAAGCTA (SEQ ID NO: 3)

Mouse CD47 amino acid isoform 2 (XP_006521874.1)
MWPLAAALLLGSCCCGSAQLLFSNVNSIEFTSCNETVVIPCIVRNVEAQSTEE
MFVKWKLNKSYIFIYDGNKNSTTTDQNFTSAKISVSDLINGLASLKMDKRDA
MVGNYTCEVTELSREGKTVIELKNRTVSWFSPNEKILIVIFPILAILLFWGKFG
ILTLKYKSSHTNKRIILLLVAGLVLTVIVVVGAILLIPGEKPVKNASGLGLIVISTG
ILILLQYNVFMTAFGMTSFTIAILITQVLGYVLALVGLCLCIMACEPVHGPLLISG
LGIIALAELLGLVYMKFV*ASNQRTIQPPRNR* (SEQ ID NO: 4)

Mouse CD47 mRNA isoform 3 (XM_006521807.1)
GCCTACACCGGGAGAGCAGGGAGGAGGAGTTGGACTGAGGTTGGGCGGCTC
CGAGGTCCAGGGCGAGCTTGGCCAGAGGGAGTAGAGAGCAGCGGGGCTGC
GCAGGGACGCGTGCCGTGAGTTCCGGTGAGCGTGTGTGCCCATGCTCCCGT
CTTTCAGGCCGGGCCAGGACACGAAGCCGGAAGAGAGCTGGCTGGAGGGAC
GGGGGCCGTGAGCAGAGAGTGCAACCGGCGCAGCCCCGGGGACAGGCTGA
TTCTTGGCGCTCTCCGCCGGAGCCTGCCCAGGGCTGGGTGTGAGGCTGGCGT
CACGTCAACGAGCAGAGGCGGCCAGGCGGGGCGGAGTGCGCGTGCGCGGG
GCGGCGAGCACGCGCGCGCGCGCACCCCCGGGCAGCCTGGGCGGCCGCTCC
TGCCTGTCACTGCTGCGGCGCTGCTGGTCGGTCGTTTCCCTTGAAGGCAGCA
GCGGAGGCGGCGGCTGCTCCAGACACCTGCGGCGGCGACCCCCCGGCGGCG
CGGAGATGTGGCCCTTGGCGGCGGCGCTGTTGCTGGGCTCCTGCTGCT
GCGGTTCAGCTCAACTACTGTTTAGTAACGTCAACTCCATAGAGTTCAC
TTCATGCAATGAAACTGTGGTCATCCCTTGCATCGTCCGTAATGTGGAG
GCGCAAAGCACCGAAGAAATGTTTGTGAAGTGGAAGTTGAACAAATCG
TATATTTTCATCTATGATGGAAATAAAAATAGCACTACTACAGATCAAA
ACTTTACCAGTGCAAAAATCTCAGTCTCAGACTTAATCAATGGCATTGC
CTCCTTTGAAAATGGATAAGCGCGATGCCATGGTGGGAAACTACACTTGC
GAAGTGACAGAGTTATCCAGAGAAGGCAAAACAGTTATAGAGCTGAAA
AACCGCACGGCCTTCAACACTGACCAAGGATCAGCCTGTTCTTACGAGG
AGGAGAAAGGAGGTTGCAAATTAGTTTCGTGGTTTTCTCCAAATGAAAA
GATCCTCATTGTTATTTTCCCAATTTTGGCTATACTCCTGTTCTGGGGAA
AGTTTGGTATTTTAACACTCAAATATAAATCCAGCCATACGAATAAGAG
AATCATTCTGCTGCTCGTTGCCGGGCTGGTGCTCACAGTCATCGTGGTT
GTTGGAGCCATCCTTCTCATCCCAGGAGAAAAGCCCGTGAAGAATGCTT
CTGGACTTGGCCTCATTGTAATCTCTACGGGGATATTAATACTACTTCA
GTACAATGTGTTTATGACAGCTTTTGGAATGACCTCTTTCACCATTGCC
ATATTGATCACTCAAGTGCTGGGCTACGTCCTTGCTTTGGTCGGGCTGT
GTCTCTGCATCATGGCATGTGAGCCAGTGCACGGCCCCCTTTTGATTTC
AGGTTTGGGGATCATAGCTCTAGCAGAACTACTTGGATTAGTTTATATG
AAGTTTGTCGCTTCCAACCAGAGGACTATCCAACCTCCTAGGAAAGCTG
TAGAGGAACCCCTTAACGAATAGGTGAAGGGAAGTGAGGGACTGTAACTT
GGAAGTCAGAAATGGAAGAATACAGTTGTCTAAGCACCAGGTCTTCACGAC
TCACAGCTGGAAGGAACAGACAACAGTAACTGACTTCCATCCAGGAAAACA
TGTCACATAAATGATTACTAAGTTTATATTCAAAGCAGCTGTACTTTACATA
ATAAAAAAAATATGATGTGCTGTGTAACCAATTGGAATCCCATTTTTCTATT
GTTTCTACTCAACTAGGGGCAAACGTTTCAGGGGCAACTTCCAAGAATGATG
CTTGTTAGATCCTAGAGTCTCTGAACACTGAGTTTAAATTGATTCCGAGTGA
GACTCGCCAAGCACTAACCTGAGGGTTAGTTACCCAGAGATACCTATGAAA
AACAGTGGTATCCAGCAAGCCTTAGTAAACTCAGGTTGCCAGCAGCTTTGCC
ACTTCCGCTGCTAGCTGAATAACAAGACTGCCACTTCTGGGTCATAGTGATA
GAGACTGAAGTAGAAAAACGAATGTGGTTGGGCAAATCCCGTGTGGCCCCT
CTGTGTGCTATGATATTGATGGCACTGGTGTCTTCATTCTTGGGGGTTGCCAT
CATTCACACACACCCCTTTGACATACAGTGCACCCCAGTTTTGAATACATTT
TTTTTGCACCCTGTCCCGTTCTCGCTACTTTGATTTGCGTTATGATATATAT
ATATATATAATACCTTTTCTCCTCTTTAAACATGGTCCTGTGACACAATAGTC
AGTTGCAGAAAGGAGCCAGACTTATTCGCAAAGCACTGTGCTCAAACTCTTC
AGAAAAAAAGGAAAAAAAAAAAAAAGCTATAGTTGTAACATATGTATTCCAG
ACCTCTGGTTTAAAGGCAAAAGAAAAAAAATCTACAGTGTTTCTTCTCATGT
TTTCTGATCGGAGGCATGACAAAGCAAGACTGAAATCTGAACTGTGTCTCCT
GCATGGCAACACGTGTCTCCGTCAGGCCCTCGCAAGGCCCGGGGAGGGGT
TCTACGCCTCTTGTCTCTTTGTTGCATGCTGAACACTCATCGCCTTCCTACTG
TATCCTGCCTCCTGCAGCCTCCCTCTTCCTCCTCCTCTTCCTCTTCCTCCTCTT
CCTCCTCCTCCTCTTCCTCCAAGTTTGAAAGGTCAAACAAAACTACCAC
ATTCCCTACCCAGTTAGAAGAAAACCACCGTCCTGACAGTTGTGATCGCATG
GAGTACTTTTAGATTATTAGCACCTGTTTTTACCTCGTTTGTGGGCGTGTTTG
TATGTGCACATGTATGAAGTCGGCACATGCACCTTCTGTATGGGCAGAGGCG
TGGCATCTACAGAAGAGCAGATGCCAACTTTGTGCTTTTAGTGAATACATTA
AAAAAAAAAACCAACGGTCCTTATTGAGTGGAATTCTATTTGATGCAAAT
ATTTGAGCTCTTTAAGACTTTAAAACTAGATAATGTGCCAAGCTTTTAGGAC
TGCTCACCAGTGCCCTCTGAAGAAACACCAGTACTTTTTCCTGTTTGTGTAAT
AAAGGCATATTTGTATTTGTGTTTGCATCACTAATGGTTATTCTTCTTAGTC
CACTGAATGTTTCCATGTGCCTCTCGTATGCCAAACTTTTTGTCATCTTTCAT TABLE 3-continued

```
GTGGGGACCAAATGGTTTGTCTGTGGCAAACCTAAACCTATGACCTGCTGAG
GCCTCTCAGAAAACTGACCACAGTACCAAGATAGTACTTCGCAAAGAAAAG
TAGGTTCCCTCCCTGGTTTTGTAGCTGTCGCAATATTAGCGTAATTCCAAG
GAGCTGAACGCCTTTATATAAATCTGATGGCACCTGATGCTTTTAGTTCTGA
AAATATTTACACTCGGATCATGTTGTTGATGACTTAAACAAAGTTTTGATGA
AGAGAGCAAAAAAAAGCAGGTGGATTGGAACAGTTTCAGGGTTTTTTTT
GTTTTTTGTTTTTTGTTTTTGTTTTTTTTTTTATTTTTGTTTTTCTGTTCTCTG
TTAGAAAAGTCAGGTGTTCTCTGTCAGGCTATCTTTATAGTCAATTTTTTTA
CGAACTAAAGTAGTACCTTTTAATATGTAGTCAACGCCCCTCTGCTCGGGGT
TCAGTTTTGGGTCTTAACCAGCTGTCATGTTCTCTATGCTGCCTGCCACTTGA
GGCACTGAGTGCCCTAGACAGTCCCATCGGTGGTAGCCAGGGAAACGAAAG
ACGAACTCAACTCTTGCTCCTAATAATCAACTCTCTGTATGAAGGATGGCAG
CATTAAGAGTCCTCCTGCCTGGGCATTATTGGGCAGTTCACCCTCTTTAAA
TCAAACCCGCAGTGGCTCCCAGTTCTCGTCCCATCAGATTTAAATTGCTAAC
AGTATGGGGGGCACCACGCATCTGTTTTGTCCCACAATGCGCTTTTCTCTCC
CAAATCCCGATTTCTGCTGTCATAGCCTCTATTCAATTTTTATTTATTGTCTG
CCCTCCACTTATACAATCGTAGAGAGCAATGCCATTTGTCACTTTCTGCAAC
AGTTTTTTGAGCCTTTATGGCTGAATCCCATTTTTCTTCTCTTTCAAACTGTTT
GCTCCATTGCTCCTCCCGCACGGCTGTCCGTACAGTCATCCCATCCATCTGG
GGGCCTCTTTCATCTCTCACCCTTCCTGGTGCTTCGTGGATCTCTGCTTACCT
CTGTGGGTTTTTTTTTTTTTTTGACTTATTCTTCTCACTGGACTTTAAGATT
ACTTCCACAGCGAAACTGCTGCCTCCCTTTTCTGCCCGCAGTGTTCTGCGTA
CTTTAGATACTACTCAGTGCTGACATTTGATGGCAAAAGTTGCCTGCACTTA
AATTTCTCTTTTTAATAGGGTGAACTAGAGTTGGAGTTTTTTTCTCTTTTTTCT
CTTTTCTCTCTCTCTCTCTCTCTCTCTCTCTCTCTCTCTCTCTCTCCCTCCCT
CCCTCCCTCCCTCCCTCCCTCTCTCTCTTTTTCTTTCTTTCTTTCTTTC
TTTCTTTCTTTCTTTCTTTCTTTCTTCTTTTTTGACAAATCTCACAGGC
TTTGAGAATTATAAAAGGTGACAGTTCACCTGAAAATCACAGGTCTGGTCTG
TTTAAATTGTTGAGAAATATCCGATTAAAAGTCTTGTGGCTGTGTCCTAATA
GGCTCTCTTTCAGGACGTTGTAGTCAATAGAGTGGCTGAACCATACTTGAGT
TTATAAAGCTCAAAAACTGATGCACCCACTCTGCTATTATCGTGTTAGTAAG
AGTTCAGCTGTATATCATTGTCTAGGTTTATCTTGTCCTACAGTGGGTATTCA
AATATGGCCACCAGAGGATATGTGTAAATATAAGCACCTGTATTTGCCTGTT
GTTGAGAACTGGAGGGAAAACAAAAAATGTCTGGCAACCCTTTGCCTTTTA
ACCGTAATTAATTGACAGTTTATTTAGAGATAAGAGTTTTCAAAAATCTCTT
AACTGCCACAACCCACAGAGGGTCTTGTTTTGCCATCTTCAGTGGCTCACAG
ATATGATCCAAGTTAACTTGAAAGAGATGAGCAGTACCCAGGAAATTGTCC
TGCCTTTAACTCTGGCTGTCCTTAATTATGACTGTTTAATGCTGAATTTTCCA
TCCGTCTAGTGTTTGAGGGTAAAGAAAAGCCTTTTTTAAATAAGTATTTCTG
TAAAACGGCATCGGTGGGATCTTCTGTGTTGCTATCACGGGTGAAAGAGGG
AAACATTTCTTATTTTTATTAAGCAGAGCATTATTTACAGAAACCCATTGTT
GAGAATTAGTTCCCACATCATATAAATATCCATTAACCATTCTAAATTGTAA
GAGAACTCCAGTGTTGCTATGCACAAGGAACTCTCCTGGGGCCCTTTTTTG
CATAGCAATTAAAGGTATGCTATTTGTCAGTAGCCATTTTTTGCAGTGATTT
AAAGACCAAAGTTGTTTTACAGCTGTGTTACCCTTAAAGGTTTTTTTTTATG
TATTAAATCAATTTATCACTGTTTGAAGCTTTGAATACCTGCAATCTTTGCCA
AGATACTTTTTTATTTAAAAAAAATAACTGTGTAAATATTACCCTGTAATATTA
TATATACTTAATAAAACATTTTAAGCTA (SEQ ID NO: 5)
```

Mouse CD47 amino acid isoform 3 (XP_006521870.1)
MWPLAAALLLGSCCCGSA**QLLFSNVNSIEFTSCNETVVIPCIVRNVEAQSTEE
MFVKWKLNKSYIFIYDGNKNSTTTDQNFTSAKISVSDLINGIASLKMDKRDA
MVGNVTCEVTELSREGKTVIELKNRTAFNTDQGSACSYEEEKGGCKLVSW
FSPNEK**ILIVIFPILAILLFWGKFGILTLKYKSSHTNKRIILLLVAGLVLTVIVVG
AILLIPGEKPVKNASGLGLIVISTGILILLQYNVFMTAFGMTSFTIAILITQVLGYV
LALVGLCLCIMACEPVHGPLLISGLGIIALAELLGLVYMKFV*ASNQRTIQPPRKAV
EEPLNE* (SEQ ID NO: 6)

Mouse CD47 mRNA isoform 4 (XM_006521808.1)
```
GCCTACACCGGGAGAGCAGGGAGGAGGAGTTGGACTGAGGTTGGGCGGCTC
CGAGGTCCAGGGCGAGCTTGGCCAGAGGGAGTAGAGAGCAGCGGGGCTGC
GCAGGGACGCGTGCCGTGAGTTCCGGTGAGCGTGTGTGTCCCATGCTCCCGT
CTTTCAGGCCGGCCCAGGACACGAAGCCGGAAGAGAGCTGGCTGGAGGGAC
GGGGGCCGTGAGCAGAGAGTGCAACCCGCGCAGCCCCGGGGACAGGCTGA
TTCTTGGCGCTCTCCGCCGGAGCCTGCCCAGGGCTGGGTGTGAGGCTGGCGT
CACGTCAACGAGCAGAGGCGGCCAGGCGGGGCGGAGTGCGCGTGCGCGGG
GCGGCGAGCACGCGCGCGCGCGCACCCCCGGGCAGCCTGGGCGGCCGCTCC
TGCCTGTCACTGCTGCGGCGCTGCTGGTCGGTCGTTTCCCTTGAAGGCAGCA
GCGGAGGCGGCGGCTGCTGCAGACACCTGCGGCGGCGACGCCGCGGCGGCG
CGGAG**ATGTGGCCCTTGGCGGCGGCGCTGTTGCTGGGCTCCTGCTGCT
GCGGGTTCAGCTCAACTACTGTTTAGTAACGTCAACTCCATAGAGTTCAC
TTCATGCAATGAAACTGTGGTCATCCCTTGCATCGTCCGTAATGTGGAG
GCGCAAAGCACCGAAGAAATGTTTGTGAAGTGGAAGTTGAACAAATCG
TATATTTTCATCTATGATGGAAATAAAAATAGCACTACTACAGATCAAA
ACTTTACCAGTGCAAAATCTCAGTCTCAGACTTAATCAATGGCATTGC
CTCTTTGAAAATGGATAAGCGCGATGCCATGGTGGGAAACTACACTTGC
GAAGTGACAGAGTTATCCAGAGAAGGCAAACAGTTATAGAGCTGAAA
AACCGCACGGTTTCGTGGTTTTCTCCAAATGAAAAGATCCTCATTGTTA
TTTTCCCAATTTTGGCTATACTCCTGTTCTGGGGAAAGTTTGGTATTTTA
ACACTCAAATATAAATCCAGCCATACGAATAAGAGAATCATTCTGCTGC**
```

TABLE 3-continued

```
TCGTTGCCGGGCTGGTGCTCACAGTCATCGTGGTTGTTGGAGCCATCCT
TCTCATCCCAGGAGAAAAGCCCGTGAAGAATGCTTCTGGACTTGGCCTC
ATTGTAATCTCTACGGGGATATTAATACTACTTCAGTACAATGTGTTTAT
GACAGCTTTTGGAATGACCTCTTTCACCATTGCCATATTGATCACTCAA
GTGCTGGGCTACGTCCTTGCTTTGGTCGGGCTGTGTCTCTGCATCATGG
CATGTGAGCCAGTGCACGGCCCCCTTTTGATTTCAGGTTTGGGGATCAT
AGCTCTAGCAGAACTACTTGGATTAGTTTATATGAAGTTTGTCGCTTCC
AACCAGAGGACTATCCAACCTCCTAGGAAAGCTGTAGAGGAACCCCTTA
ACGCATTTAAAGAGTCAAAAGGAATGATGAATGACGAATAGGTGAAGGG
AAGTGACGGACTGTAACTTGGAAGTCAGAAATGGAAGAATACAGTTGTCTA
AGCACCAGGTCTTCACGACTCACAGCTGGAAGGAACAGACAACAGTAACTG
ACTTCCATCCAGGAAAACATGTCACATAAATGATTACTAAGTTTATATTCAA
AGCAGCTGTACTTTACATAATAAAAAAAATATGATGTGCTGTGTAACCAATT
GGAATCCCATTTTTCTATTGTTTCTACTCAACTAGGGGCAAACGTTTCAGGG
GCAACTTCCAAGAATGATGCTTGTTAGATCCTAGAGTCTCTGAACACTGAGT
TTAAAATTGATTCCGAGTGAGACTCGCCAAGCACTAACCTGAGGGTTAGTTAC
CCAGAGATACCTATGAAAAACAGTGGTATCCAGCAAGCCTTAGTAAACTCA
GGTTGCCAGCAGCTTTGCCACTTCCGCTGCTAGCTGAATAACAAGACTGCCA
CTTCTGGGTCATAGTGATAGAGACTGAAGTAGAAAAACGAATGTGGTTGGG
CAAATCCCGTGTGGCCCCTCTGTGTGCTATGATATTGATGGCACTGGTGTCT
TCATTCTTGGGGGTTGCCATCATTCACACACACCCCTTTGACATACAGTGCA
CCCCAGTTTTGAATACATTTTTTTTGCACCCTGTCCCGTTCTGCTACTTTGATT
TGCGTTATGATATATATATATATATAATACCTTTTCTCCTCTTTAAACATC
GTCCTGTGACACAATAGTCAGTTGCAGAAAGGAGCCAGACTTATTCGCAAA
GCACTGTGCTCAAACTCTTCAGAAAAAAAGGAAAAAAAAAAAAAGCTATAG
TTGTAACATATGTATTCCAGACCTCTGGTTTAAAGGCAAAAGAAAAAAAAT
CTACAGTGTTTCTTCTCATGTTTTCTGATCGGAGGCATGACAAAGCAAGACT
GAAATCTGAACTGTGTCTCCTGCATGGCAACACGTGTCTCCGTCAGGCCCTC
GCAAGGCCCGGGGAGGGGGTTCTACGCCTCTTGTCTCTTTGTTGCATGCTGA
ACACTCATCGCCTTCCTACTGTATCCTGCCTCCTGCAGCCTCCCTCTTCCTCC
TCCTCTTCCTCTTCCTCCTCTTCCTCCTCCTCCTCTTCCTCCAAGTTTGAA
AGGTCAAACAAAACTACCACATTCCCTACCCAGTTAGAAGAAAACCACCGT
CCTGACAGTTGTGATCGCATGGAGTACTTTTAGATTATTAGCACCTGTTTTA
CCTCGTTTGTGGGCGTGTTTGTATGTGCACATGTATGAAGTCGGCACATGCA
CCTTCTGTATGGGCAGAGGCGTGGCATCTACAGAAGAGCAGATGCCAACTT
TGTGCTTTTAGTGAATACATTAAAAAAAAAAAACCAACGGTCCTTATTGAGT
GGAATTCTATTTGATGCAAATATTTGAGCTCTTTAAGACTTTAAAACTAGAT
AATGTGCCAAGCTTTTAGGACTGCTCACCAGTGCCCTCTGAAGAAACACCAG
TACTTTTTCCTGTTTGTGTAATAAAGGCATATTTGTATTTGTGTTTGCATCAC
TAATGGTTATTTCTTCTTAGTCCACTGAATGTTTCCATGTGCCTCTCGTATGC
CAAACTTTTTGTCATCTTTCATGTGGGGACCAAATGGTTTGTCTGTGGCAAA
CCTAAACCTATGACCTGCTGAGGCCTCTCAGAAAACTGACCACAGTACCAA
GATAGTACTTCGCAAAGAAAAGTAGGTTCCCTCCCTGGTTTTGTAGCTGTCG
CCAATATTAGCGTAATTCCAAGGAGCTGAACGCCTTTATATAAATCTGATGG
CACCTGATGCTTTTAGTTCTGAAAATATTTACACTCGGATCATGTTGTTGATG
ACTTAAACAAAGTTTTGATGAAGAGAGCAAAAAAAAAGCAGGTGGATTTGG
AACAGTTTCAGGGTTTTTTTGTTTTTTGTTTTTGTTTTTGTTTTTTTTTTTT
ATTTTTGTTTTTCTGTTCTCTGTTAGAAAAGTCAGGTGTTCTCTGTCAGGCTA
TCTTTATAGTCAATTTTTTTACGAACTAAAGTAGTACCTTTTAATATGTAGT
CAACGCCCTCTGCTCGGGGTTCAGTTTTGGGTCTTAACCAGCTGTCATGTTC
TCTATGCTGCCTGCCACTTGAGGCACTGAGTGCCCTAGACAGTCCCATCGGT
GGTAGCCAGGGAAACGAAAGACGAACTCAACTCTTGCTCCTAATAATCAAC
TCTCTGTATGAAGGATGGCAGCATTAAGAGTCCTCCTGCCTGGGCATTATTG
GGCCAGTTCACCCTCTTTAAATCAAACCCGCAGTGGCTCCCAGTTCTCGTCC
CATCAGATTTAAATTGCTAACAGTATGGGGGGCACCACGCATCTGTTTTGTC
CCACAATGCGCTTTTCTCTCCCAAATCCCGATTTCTGCTGTCATAGCCTCTAT
TCAATTTTTATTTATTGTCTGCCCTCCACTTATACAATCGTAGAGAGCAATGC
CATTTGTCACTTTCTGCAACAGTTTTTTGAGCCTTTATGGCTGAATCCCATTT
TTCTTCTCTTTCAAACTGTTTGCTCCATTGCTCCTCCCGCACGGCTGTCCGTA
CAGTCATCCCATCCATCTGGGGGCCTCTTTCATCTCTCACCCTTCCTGGTGCT
TCGTGGATCTCTGCTTACCTCTGTGGGTTTTTTTTTTTTTTTGACTTATTCTT
CTCACTGGACTTTAAGATTACTTCCACAGCGAAAGTGCTGCCTCCCTTTTCTG
CCCGCAGTGTTCTGCGTACTTTAGATACTACTCAGTGCTGACATTTGATGGC
AAAAGTTGCCTGCACTTAAATTTCTCTTTTTAATAGGGTGAACTAGAGTTGG
AGTTTTTTTTCTCTTTTTTCTCTTTTCTCTCTCTCTCTCTCTCTCTCTCTCT
CTCTCTCTCTCCCTCCCTCCCTCCCTCCCTCCCTCCCTCCCTCTCTCTCT
TTTTCTTTCTTTCTTTCTTTCTTTCTTTCTTTCTTTCTTTCTTTCTTTT
TTTGACAAATCTCACAGGCTTTGAGAATTATAAAAGGTGACAGTTCACCTGA
AAATCACAGGTCTGGTCTGTTTAAATTGTTGAGAAATATCCGATTAAAAGTC
TTGTGGCTGTGTCCTAATAGGCTCTCTTTCAGGACGTTGTAGTCAATAGAGT
GGCTGAACCATACTTGAGTTTATAAAGCTCAAAAACTGATGCACCCACTCTG
CTATTATCGTGTTAGTAAGAGTTCAGCTGTATATCATTGTCTAGGTTTATCTT
GTCCTACAGTGGGTATTCAAATATGGCCACCAGAGGATATGTGTAAATATA
AGCACCTGTATTTGCCTGTTGTTGAGAACTGGAGGGAAAACAAAAAATGTC
TGGCAACCCTTTGCCTTTTTAACCGTAATTAATTGACAGTTTATTTAGAGATA
AGAGTTTTCAAAAATCTCTTAACTGCCACAACCCACAGAGGGTCTTGTTTTG
CCATCTTCAGTGGCTCACAGATATGATCCAAGTTAACTTGAAAGAGATGAGC
AGTACCCAGGAAATTGTCCTGCCTTTAACTCTGGCTGTCCTTAATTATGACT
GTTTAATGCTGAATTTTCCATCCGTCTAGTGTTTGAGGGTAAAGAAAAGCCT
TTTTTAAATAAGTATTTCTGTAAAACGGGATCGGTGGGATCTTCTGTGTTGCT
```

TABLE 3-continued

```
ATCACGGGTGAAAGAGGGAAACATTTCTTATTTTTATTAAGCAGAGCATTAT
TTACAGAAAGCCATTGTTGAGAATTAGTTCCCACATCATATAAATATCCATT
AACCATTCTAAATTGTAAGAGAACTCCAGTGTTGCTATGCACAAGGAACTCT
CCTGGGGGCCTTTTTTTGCATAGCAATTAAAGGTATGCTATTTGTCAGTAGC
CATTTTTTGCAGTGATTTAAAGACCAAAGTTGTTTTACAGCTGTGTTACCCTT
AAAGGTTTTTTTTTTATGTATTAAATCAATTTATCACTGTTTGAAGCTTTGAA
TACCTGCAATCTTTGCCAAGATACTTTTTTATTTAAAAAAATAACTGTGTAA
ATATTACCCTGTAATATTATATATACTTAATAAAACATTTTAAGCTA (SEQ ID
NO: 7)

Mouse CD47 amino acid isoform 4 (XP_006521871.1)
MWPLAAALLLGSCCCGSA**QLLFSNVNSIEFTSCNETVVIPCIVRNVEAQSTEE
MFVKWKLNKSYIFIYDGNKNSTTTDQNFTSAKISVSDLINGIASLKMDKRDA
MVGNYTCEVTELSREGKTVIELKNRTVSWFSPNEK**ILIVIFPILAILLFWGKFG
ILTLKYKSSHTNKRIILLLVAGLVLTVIVVVGAILLIPGEKPVKNASGLGLIVISTG
ILILLQYNVFMTAFGMTSFTIAILITQVLGYVLALVGLCLCIMACEPVHGPLLISG
LGIIALAELLGLVYMKFV*ASNQRTIQPPRKAVEEPLNAFKESKGMMNDE* (SEQ ID
NO: 8)

Human CD47 mRNA isoform 1 (XM_005247909.1)
AGTGGGAGCGCGCGTGCGCGCGGCCGTGCAGCCTGGGCAGTGGGTCCTGCC
TGTGACGCGCGGCGGCGGTCGGTCCTGCCTGTAACGGCGGCGGCGGCTGCT
GCTCCGGACACCTGCGGCGGCGGCGGCGACCCCGCGGCGGGCGCGGAG**AT
GTGGCCCCTGGTAGCGGCGCTGTTGCTGGGCTCGGCGTGCTGCGGATC
AGCTCAGCTACTATTTAATAAAACAAAATCTGTAGAATTCACGTTTTGTA
ATGACACTGTCGTCATTCCATGCTTTGTTACTAATATGGAGGCACAAAA
CACTACTGAAGTATACGTAAAGTGGAAATTTAAAGGAAGAGATATTTAC
ACCTTTGATGGAGCTCTAAACAAGTCCACTGTCCCCACTGACTTTAGTA
GTGCAAAAATTGAAGTCTCACAATTACTAAAAGGAGATGCCTCTTTGAA
GATGGATAAGAGTGATGCTGTCTCACACACAGGAAACTACACTTGTGAA
GTAACAGAATTAACCAGAGAAGGTGAAACGATCATCGAGCTAAAATATC
GTGTTGTTTCATGGTTTTCTCCAAATGAAAATATTCTTATTGTTATTTTC
CCAATTTTTGCTATACTCCTGTTCTGGGGACAGTTTGGTATTAAAACAC
TTAAATATAGATCCGGTGGTATGGATGAGAAAACAATTGCTTTACTTGT
TGCTGGACTAGTGATCACTGTCATTGTCATTGTTGGAGCCATTCTTTTC
GTCCCAGGTGAATATTCATTAAAGAATGCTACTGGCCTTGGTTTAATTG
TGACTTCTACAGGGATATTAATATTACTTCACTACTATGTGTTTAGTACA
GCGATTGGATTAACCTCCTTCGTCATTGCCATATTGGTTATTCAGGTGA
TAGCCTATATCCTCGCTGTGGTTGGACTGAGTCTCTGTATTGCGGCGTG
TATACCAATGCATGGCCCTCTTCTGATTTCAGGTTTGAGTATCTTAGCT
CTAGCACAATTACTTGGACTAGTTTATATGAAATTTGTGAATAA**CTGAA
GTGAAGTGATGGACTCCGATTTGGAGAGTAGTAAGACGTGAAAGGAATACA
CTTGTGTTTAAGCACCATGGCCTTGATGATTCACTGTTGGGGAGAAGAAACA
AGAAAAGTAACTGGTTGTCACCTATGAGACCCTTACGTGATTGTTAGTTAAG
TTTTTATTCAAAGCAGCTGTAATTTAGTTAATAAAATAATTATGATCTATGTT
GTTTGCCCAATTGAGATCCAGTTTTTTGTTGTTATTTTTAATCAATTAGGGGC
AATAGTAGAATGGACAATTTCCAAGAATGATGCCTTTCAGGTCCTAGGGCCT
CTGGCCTCTAGGTAACCAGTTTAAATTGGTTCAGGGTGATAACTACTTAGCA
CTGCCCTGGTGATTACCCAGAGATATCTATGAAACCAGTGGCTTCCATCAA
ACCTTTGCCAACTCAGGTTCACAGCAGCTTTGGGCAGTTATGGCAGTATGGC
ATTAGCTGAGAGGTGTCTGCCACTTCTGGGTCAATGGAATAATAAATTAAGT
ACAGGCAGGAATTTGGTTGGGAGCATCTTGTATGATCTCCGTATGATGTGAT
ATTGATGGAGATAGTGGTCCTCATTCTTGGGGGTTGCCATTCCCACATTCCC
CCTTCAACAAACAGTGTAACAGGTCCTTCCCAGATTTAGGGTACTTTTATTG
ATGGATATGTTTTCCTTTTATTCACATAACCCCTTGAAACCCTGTCTTGTCCT
CCTGTTACTTGCTTCTGCTGTACAAGATGTAGCACCTTTTCTCCTCTTTGAAC
ATGGTCTAGTGACACGGTAGCACCAGTTGCAGGAAGGAGCCAGACTTGTTC
TCAGAGCACTGTGTTCACACTTTTCAGCAAAAATAGCTATGGTTGTAACATA
TGTATTCCCTTCCTCTGATTTGAAGGCAAAAATCTACAGTGTTTCTTCACTTC
TTTTCTGATCTGGGGCATGAAAAAAGCAAGATTGAAATTTGAACTATGAGTC
TCCTGCATGGGAACAAAATGTGTGTCACCATCAGGCCAACAGGCCAGCCCTT
GAATGGGGATTTATTACTGTTGTATCTATGTTGCATGATAAACATTCATCAC
CTTCCTCCTGTAGTCCTGCCTCGTACTCCCCTTCCCCTATGATTGAAAAGTAA
ACAAAACCCACATTTCCTATCCTGGTTAGAAGAAAATTAATGTTCTGACAGT
TGTGATCGCCTGGAGTACTTTTAGACTTTTAGCATTCGTTTTTTACCTGTTTG
TGGATGTGTGTTTGTATGTGCATACGTATGAGATAGGCACATGCATCTTCTG
TATGGACAAAGGTGGGGTACCTACAGGAGAGCAAAGGTTAATTTTTGTGCTT
TTAGTAAAAACATTTAAATACAAAGTTCTTTATTGGGTGGAATTATATTTGA
TGCAAATATTTGATCACTTAAAACTTTTAAAACTTCTAGGTAATTTGCCACG
CTTTTTTGACTGCTCACCAATACCCTGTAAAAATACGTAATTCTTCCTGTTTGT
GTAATAAGATATTCATATTTGTAGTTGCATTAATAATAGTTATTTCTTAGTCC
ATCAGATGTTCCCGTGTGCCTCTTTTATGCCAAATTGATTGTCATATTTCATG
TTGGGACCAAGTAGTTTCCCCATGGCAAACCTAAATTTATGACCTGCTGAGG
CCTCTCAGAAAACTGAGCATACTAGCAAGACAGCTCTTCTTGAAAAAAAAA
ATATGTATACACAAATATATACGTATATCTATATATACGTGAAAGCTACAA
ACATGTATATTCTTCCTTGATTGTGTAGCTGTCCAAAATAATAACATATATA
GAGGGAGCTGTATTCCTTTATACAAATCTGATGGCTCCTGCAGCACTTTTTC
CTTCTGAAAATATTTACATTTTGCTAACCTAGTTTGTTACTTTAAAAATCAGT
TTTGATGAAAGGAGGGAAAAGCAGATGGACTTGAAAAAGATCCAAGCTCCT
ATTAGAAAAGGTATGAAAATCTTTATAGTAAAATTTTTTATAAACTAAAGTT
```

TABLE 3-continued

```
GTACCTTTTAATATGTAGTAAACTCTCATTTATTTGGGGTTCGCTCTTGGATC
TCATCCATCCATTGTGTTCTCTTTAATGCTGCCTGCCTTTTGAGGCATTCACT
GCCCCTAGACAATGCCACCAGAGATAGTGGGGGAAATGCCAGATGAAACCAA
CTCTTGCTCTCACTAGTTGTCAGCTTCTCTGGATAAGTGACCACAGAAGCAG
GAGTCCTCCTGCTTGGGCATCATTGGGCCAGTTCCTTCTCTTTAAATCAGATT
TGTAATGGCTCCCAAATTCCATCACATCACATTTAAATTGCAGACAGTGTTT
TGCACATCATGTATCTGTTTTGTCCCATAATATGCTTTTTACTCCCTGATCCC
AGTTTCTGCTCTTGACTCTTCCATTCAGTTTTATTTATTGTGTTGTTCTCACAGT
GACACCATTTGTCCTTTTCTGCAACAACCTTTCCAGCTACTTTTGCCAAATTC
TATTTGTCTTCTCCTTCAAAACATTCTCCTTTGCAGTTCCTCTTCATCTGTGTA
GCTGCTCTTTTGTCTCTTAACTTACCATTCCTATAGTACTTTATGCATCTCTGC
TTAGTTCTATTAGTTTTTTGGCCTTGCTCTTCTCCTTGATTTTAAAATTCCTTC
TATAGCTAGAGCTTTTCTTTCTTTCATTCTCTCTTCCTGCAGTGTTTTGCATAC
ATCAGAAGCTAGGTACATAAGTTAAATGATTGAGAGTTGGCTGTATTTAGAT
TTATCACTTTTTAATAGGGTGAGCTTGAGAGTTTTCTTTCTTTCTGTTTTTTTT
TTTTGTTTTTTTTTTTTTTTTTTTTTTTTTTTTTGACTAATTTCACATGCTCT
AAAAACCTTTCAAAGGTGATTATTTTTCTCCTGGAAACTCCAAGTCCATTCTG
TTTAAATCCCTAAGAATGTCAGAATTAAAATAACAGGGCTATCCCGTAATTG
GAAATATTTCTTTTTTCAGGATGCTATAGTCAATTTAGTAAGTGACCACCAA
ATTGTTATTTGCACTAACAAAGCTCAAAACACGATAAGTTTACTCCTCCATC
TCAGTAATAAAAATTAAGCTGTAATCAACCTTCTAGGTTTCTCTTGTCTTAA
AATGGGTATTCAAAAATGGGGATCTGTGGTGTATGTATGGAAACACATACT
CCTTAATTTACCTGTTGTTGGAAACTGGAGAAATGATTGTCGGGCAACCGTT
TATTTTTTATTGTATTTTATTTGGTTGAGGGATTTTTTTATAAACAGTTTTACT
TGTGTCATATTTTAAAATTACTAACTGCCATCACCTGCTGGGTCCTTTGTTA
GGTCATTTTCAGTGACTAATAGGGATAATCCAGGTAACTTTGAAGAGATGA
GCAGTGAGTGACCAGGCAGTTTTTCTGCCTTTAGCTTTGACAGTTCTTAATTA
AGATCATTGAAGACCAGCTTTCTCATAAATTTCTCTTTTTGAAAAAAAGAAA
GCATTTGTACTAAGCTCCTCTGTAAGACAACATCTTAAATCTTAAAAGTGTT
GTTATCATGACTGGTGAGAGAAGAAAACATTTTGTTTTTATTAAATGGAGCA
TTATTTACAAAAAGCCATTGTTGAGAATTAGATCCCACATCGTATAAATATC
TATTAACCATTCTAAATAAAGAGAACTCCAGTGTTGCTATGTGCAAGATCCT
CTCTTGGAGCTTTTTTGCATAGCAATTAAAGGTGTGCTATTTGTCAGTAGCC
ATTTTTTTGCAGTGATTTGAAGACCAAAGTTGTTTTACAGCTGTGTTACCGTT
AAAGGTTTTTTTTTTTTATATGTATTAAATCAATTTATCACTGTTTAAAGCTTT
GAATATCTGCAATCTTTGCCAAGGTACTTTTTTATTTAAAAAAAAACATAAC
TTTGTAAATATTACCCTGTAATATTATATATACTTAATAAAACATTTTAAGCT
A (SEQ ID NO: 9)
```

Human CD47 amino acid isoform 1 (XP_005247966.1)
MWPLVAALLLGSACCGSAQLLFNKTKSVEFTFCNPTVVIPCFVTNMEAQNT
TEVYVKWKFKGRDIYTFDGALNKSTVPTDFSSAKIEVSQLLKGDASLKMDK
SDAVSHTGNYTCEVTELTREGETIIELKYRVVSWFSPNENILIVIFPIFAILLFW
GQFGIKTLKYRSGGMDEKTIALLVAGLVITVIVIVGAILFVPGEYSLKNATGLGLI
VTSTGILILLHYYVFSTAIGLTSFVTAILVIQVIAYILAVVGLSLCIAACIPMHGPLLI
SGLSILALAQLLGLVYMKFV*E* (SEQ ID NO: 10)

Human CD47 mRNA isoform 2 (NM_198793.2)
```
GGGGAGCAGGCGGGGGAGCGGGCGGGAAGCAGTGGGAGCGCGCGTGCGCG
CGGCCGTGCAGCCTGGGCAGTGGGTCCTGCCTGTGACGGCGCGGCGGTC
GGTCCTGCCTGTAACGGCGGCGGCGGCTGCTGCTCCAGACACCTGCGGCGG
CGGCGGCGACCCCGCGGCGGGCGCGGAGATGTGGCCCCTGGTAGCGGCG
CTGTTGCTGGGCTCGGCGTGCTGCGGATCAGCTCAGCTACTATTTAATA
AAACAAAATCTGTAGAATTCACGTTTTGTAATGACACTGTCGTCATTCC
ATGCTTTGTTCTAAATGGAGGCACAAAAACACTACTGAAGTATACGTA
AAGTGGAAATTTAAAGGAAGAGATATTTACACCTTTGATGGAGCTCTAA
ACAAGTCCACTGTCCCCACTGACTTTAGTAGTGCAAAAATTGAAGTCTC
ACAATTACTAAAAGGAGATGCCTCTTTGAAGATGGATAAGAGTGATGCT
GTCTCACACACAGGAAATACACTTGTGAAGTAACAGAATTAACCAGAG
AAGGTGAAACGATCATCGAGCTAAAATATCGTGTTGTTTCATGGTTTTC
TCCAAATGAAAATATTCTTATTGTTATTTTCCCAATTTTTGCTATACTCC
TGTTCTGGGGACAGTTTGGTATTAAAACACTTAAATATAGATCCGGTGG
TATGGATGAGAAAACAATTGCTTTACTTGTTGCTGGACTAGTGATCACT
GTCATTGTCATTGTTGGAGCCATTCTTTTCGTCCCAGGTGAATATTCATT
AAAGAATGCTACTGGCCTTGGTTTAATTGTGACTTCTACAGGGATATTA
ATATTACTTCACTACTATGTGTTTAGTACAGCGATTGGATTAACCTCCTT
CGTCATTGCCATATTGGTTATTCAGGTGATAGCCTATATCCTCGCTGTG
GTTGGACTGAGTCTCTGTATTGCGGCGTGTATACCAATGCATGGCCCTC
TTCTGATTTCAGGTTTGAGTATCTTAGCTCTAGCACAATTACTTGGACTA
GTTTATATGAAATTTGTGGCTTCCAATCAGAAGACTATACAACCTCCTA
GGAATAACTGAAGTGAAGTGATGGACTCCGATTTGGAGAGTAAGACG
TGAAAGGAATACACTTGTGTTTAAGCACCATGGCCTTGATGATTCACTGTTG
GGGAGAAGAAACAAGAAAGTAACTGGTTGTCACCTATGAGACCCTTACGT
GATTGTTAGTTAAGTTTTTATTCAAAGCAGCTGTAATTTAGTTAATAAAATA
ATTATGATCTATGTTGTTTGCCCAATTGAGATCCAGTTTTTTGTTGTTATTTT
AATCAATTAGGGGCAATAGTAGAATGGACAATTTCCAAGAATGATGCCTTT
CAGGTCCTAGGGCCTCTGGCCTCTAGGTAACCAGTTTAAATTGGTTCAGGGT
GATAACTACTTAGCACTGCCCTGGTGATTACCCAGAGATATCTATGAAAACC
AGTGGCTTCCATCAAACCTTTGCCAACTCAGGTTCACAGCAGCTTTGGGCAG
TTATGGCAGTATGGCATTAGCTGAGAGGTGTCTGCCACTTCTGGGTCAATGG
```

TABLE 3-continued

```
AATAATAAATTAAGTACAGGCAGGAATTTGGTTGGGAGCATCTTGTATGATC
TCCGTATGATGTGATATTGATGGAGATAGTGGTCCTCATTCTTGGGGGTTGC
CATTCCCACATTCCCCCTTCAACAAACAGTGTAACAGGTCCTTCCCAGATTT
AGGGTACTTTTATTGATGGATATGTTTTCCTTTTATTCACATAACCCCTTGAA
ACCCTGTCTTGTCCTCCTGTTACTTGCTTCTGCTGTACAAGATGTAGCACCTT
TTCTCCTCTTTGAACATGGTCTAGTGACACGGTAGCACCAGTTGCAGGAAGG
AGCCAGACTTGTTCTCAGAGCACTGTGTTCACACTTTTCAGCAAAAATAGCT
ATGGTTGTAACATATGTATTCCCTTCCTCTGATTTGAAGGCAAAAATCTACA
GTGTTTCTTCACTTCTTTTCTGATCTGGGGCATGAAAAAAGCAAGATTGAAA
TTTGAACTATGAGTCTCCTGCATGGCAACAAAATGTGTGTCACCATCAGGCC
AACAGGCCAGCCCTTGAATGGGGATTTATTACTGTTGTATCTATGTTGCATG
ATAAACATTCATCACCTTCCTCCTGTAGTCCTGCCTCGTACTCCCCTTCCCCT
ATGATTGAAAAGTAAACAAAACCCACATTTCCTATCCTGGTTAGAAGAAAA
TTAATGTTCTGACAGTTGTGATCGCCTGGAGTACTTTTAGACTTTTAGCATTC
GTTTTTTACCTGTTTGTGGATGTGTGTTTGTATGTGCATACGTATGAGATAGG
CACATGCATCTTCTGTATGGACAAAGGTGGGGTACCTACAGGAGAGCAAAG
GTTAATTTTGTGCTTTTAGTAAAAACATTTAAATACAAAGTTCTTTATTGGGT
GGAATTATATTTGATGCAAATATTTGATCACTTAAAACTTTTAAAACTTCTA
GGTAATTTGCCACGCTTTTTGACTGCTCACCAATACCCTGTAAAAATACGTA
ATTCTTCCTGTTTGTGTAATAAGATATTCATATTTGTAGTTGCATTAATAATA
GTTATTTCTTAGTCCATCAGATGTTCCCGTGTGCCTCTTTTATGCCAAATTGA
TTGTCATATTTCATGTTGGGACCAACTAGTTTGCCCATGGCAAACCTAAATT
TATGACCTGCTGAGGCCTCTCAGAAAACTGAGCATACTAGCAAGACAGCTC
TTCTTGAAAAAAAAAATATGTATACACAAATATATACGTATATCTATATATA
CGTATGTATATACACACATGTATATTCTTCCTTGATTGTGTAGCTGTCCAAAA
TAATAACATATATAGAGGGAGCTGTATTCCTTTATACAAATCTGATGGCTCC
TGCAGCACTTTTTCCTTCTGAAAATATTTACATTTTGCTAACCTAGTTTGTTA
CTTTAAAAATCAGTTTTGATGAAAGGAGGGAAAAGCAGATGGACTTGAAAA
AGATCCAAGCTCCTATTAGAAAAGGTATGAAAATCTTTATAGTAAAATTTTT
TATAAACTAAAGTTGTACCTTTTAATATGTAGTAAACTCTCATTTATTTGGGG
TTCGCTCTTGGATCTCATCCATCCATTGTGTTCTCTTTAATGCTGCCTGCCTTT
TGAGGCATTCACTGCCCTAGACAATGCCACCAGAGATAGTGGGGGAAATGC
CAGATGAAACCAACTCTTGCTCTCACTAGTTGTCAGCTTCTCTGGATAAGTG
ACCACAGAAGCAGGAGTCCTCCTGCTTGGGCATCATTGGGCCAGTTCCTTCT
CTTTAAATCAGATTTGTAATGGCTCCCAAATTCCATCACATCACATTTAAATT
GCAGACAGTGTTTTGCACATCATGTATCTGTTTTGTCCCATAATATGCTTTTT
ACTCCCTGATCCCAGTTTCTGCTGTTGACTCTTCCATTCAGTTTTATTTATTGT
GTGTTCTCACAGTGACACCATTTGTCCTTTTCTGCAACAACCTTTCCAGCTAC
TTTTGCCAAATTCTATTTGTCTTCTCCTTCAAAACATTCTCCTTTGCAGTTCCT
CTTCATCTGTGTAGCTGCTCTTTTGTCTCTTAACTTACCATTCCTATAGTACTT
TATGCATCTCTGCTTAGTTCTATTAGTTTTTTGGCCTTGCTCTTCTCCTTGATT
TTAAAATTCCTTCTATAGCTAGAGCTTTTCTTTCTTTCATTCTCTCTTCCTGCA
GTGTTTTGCATACATCAGAAGCTAGGTACATAAGTTAAATGATTGAGAGTTG
GCTGTATTTAGATTTATCACTTTTTAATAGGGTGAGCTTGAGAGTTTTCTTTC
TTTCTGTTTTTTTTTTGTTTTTTTTTTTTTTTTTTTTTTTTTTTGACTA
ATTTCACATGCTCTAAAAACCTTCAAAGGTGATTATTTTTCTCCTGGAAACTC
CAGGTCCATTCTGTTTAAATCCCTAAGAATGTCAGAATTAAAATAACAGGGC
TATCCCGTAATTGGAAATATTTCTTTTTTCAGGATGCTATAGTCAATTTAGTA
AGTGACCACCAAATTGTTATTTGCACTAACAAAGCTCAAAACACGATAAGTT
TACTCCTCCATCTCAGTAATAAAAATTAAGCTGTAATCAACCTTCTAGGTTT
CTCTTGTCTTAAAATGGGTATTCAAAAATGGGGATCTGTGGTGTATGTATGG
AAACACATACTCCTTAATTTACCTGTTGTTGGAAACTGGAGAAATGATTGTC
GGGCAACCGTTTATTTTTATTGTATTTTATTTGGTTGAGGGATTTTTTTATA
AACAGTTTTACTTGTGTCATATTTTAAAATTACTAACTGCCATCACCTGCTGG
GGTCCTTTGTTAGGTCATTTTCAGTGACTAATAGGGATAATCCAGGTAACTT
TGAAGAGATGAGCAGTGAGTGACCAGGCAGTTTTTCTGCCTTTAGCTTTGAC
AGTTCTTAATTAAGATCATTGAAGACCAGCTTTCTCATAAATTTCTCTTTTTG
AAAAAAAGAAAGCATTTGTACTAAGCTCCTCTGTAAGACAACATCTTAAAT
CTTAAAAGTGTTGTTATCATGACTGGTGAGAGAAGAAAACATTTTGTTTTTA
TTAAATGGAGCATTATTTACAAAAAGCCATTGTTGAGAATTAGATCCCACAT
CGTATAAATATCTATTAACCATTCTAAATAAAGAGAACTCCAGTGTTGCTAT
GTGCAAGATCCTCTCTTGGAGCTTTTTTGCATAGCAATTAAAGGTGTGCTAT
TTGTCAGTAGCCATTTTTTGCAGTGATTTGAAGACCAAAGTTGTTTTACAGC
TGTGTTACCGTTAAAGGTTTTTTTTTTATATGTATTAAATCAATTTATCACT
GTTTAAAGCTTTGAATATCTGCAATCTTTGCCAAGGTACTTTTTATTTAAAA
AAAAACATAACTTTGTAAATATTACCCTGTAATATTATATATACTTAATAAA
ACATTTTAAGCTATTTTGTTGGGCTATTTCTATTGCTGCTACAGCAGCACCA
AGCACATTTCTGAAAAATTTAATTTATTAATGTATTTTTAAGTTGCTTATATT
CTAGGTAACAATGTAAAGAATGATTTAAAATATTAATTATGAATTTTTTGAG
TATAATACCCAATAAGCTTTTAATTAGAGCAGAGTTTTAATTAAAAGTTTTA
AATCAGTC (SEQ ID NO: 11)
```

Human CD47 amino acid isoform 2 (NP_942088.1)
MWPLVAALLLGSACCGSAQLLFNKTKSVEFTFCNDTVVIPCFVTNMEAQNT
TEVYVKWKFKGRDIYTFDGALNKSTVPTDFSSAKIEVSQLLKGDASLKMDK
SDAVSHTGNYTCEVTELTREGETIIELKYRVVSWFSPNENILIVIFPIFAILLFW
GQFGIKTLKYRSGGMDEKTIALLVAGLVITVIVIVGAILFVPGEYSLKNATGLGLI
VTSTGILILLHYYVFSTAIGLTSFVIAILVIQVIAYILAVVGLSLCIAACIPMHGPLLI
SGLSILALAQLLGLVYMKFV*ASNQKTIQPPRNN* (SEQ ID NO: 12)

TABLE 3-continued

Human CD47 mRNA isoform 3 (XM_005247908.1)
AGTGGGAGCGCGCGTGCGCGCGGCCGTGCAGCCTGGGCAGTGGGTCCTGCC
TGTGACGCGCGGCGGCGGTCGGTCCTGCCTGTAACGGCGGCGGCGGCTGCT
GCTCCGGACACCTGCGGCGGCGGCGGCGACCCCGCGGCGGGCGCGGAG**AT
GTGGCCCCTGGTAGCGGCGCTGTTGCTGGGCTCGGCGTGCTGCGGATC
AGCTCAGCTACTATTTAATAAAACAAAATCTGTAGAATTCACGTTTTGTA
ATGACACTGTCGTCATTCCATGCTTTGTTACTAATATGGAGGCACAAAA
CACTACTGAAGTATACGTAAAGTGGAAATTTAAAGGAAGAGATATTTAC
ACCTTTGATGGAGCTCTAAACAAGTCCACTGTCCCCACTGACTTTAGTA
GTGCAAAAATTGAAGTCTCACAATTACTAAAAGGAGATGCCTCTTTGAA
GATGGATAAGAGTGATGCTGTCTCACACACAGGAAACTACACTTGTGAA
GTAACAGAATTAACCAGAGAAGGTGAAACGATCATCGAGCTAAAATATC
GTGTTGTTTCATGGTTTTCTCCAAATGAAAATATTCTTATTGTTATTTTC
CCAATTTTTGCTATACTCCTGTTCTGGGGACAGTTTGGTATTAAAACAC
TTAAATATAGATCCGGTGGTATGGATGAGAAAACAATTGCTTTACTTGT
TGCTGGACTAGTGATCACTGTCATTGTCATTGTTGGAGCCATTCTTTTC
GTCCCAGGTGAATATTCATTAAAGAATGCTACTGGCCTTGGTTTAATTG
TGACTTCTACAGGGATATTAATATTACTTCACTACTATGTGTTTAGTACA
GCGATTGGATTAACCTCCTTCGTCATTGCCATATTGGTTATTCAGGTGA
TAGCCTATATCCTCGCTGTGGTTGGACTGAGTCTCTGTATTGCGGCGTG
TATACCAATGCATGGCCCTCTTCTGATTTCAGGTTTGAGTATCTTAGCT
CTAGCACAATTACTTGGACTAGTTTATATGAAATTTGTGGCTTCCAATC
AGAAGACTATACAACCTCCTAGGAAAGCTGTAGAGGAACCCCTTAATGA
ATAACTGAAGTGAAGTGATGGACTCCGATTTGGAGAGTAGTAAGACGTGAA
AGGAATACACTTGTGTTTAAGCACCATGGCCTTGATGATTCACTGTTGGGGA
GAAGAAACAAGAAAAGTAACTGGTTGTCACCTATGAGACCCTTACGTGATT
GTTAGTAAGTTTTTATTCAAAGCAGTGTAATTTAGTTAATAAAATAATTAT
GATCTATGTTGTTTGCCCAATTGAGATCCAGTTTTTTGTTGTTATTTTTAATC
AATTAGGGGCAATAGTAGAATGGACAATTTCCAAGAATGATGCCTTTCAGG
TCCTAGGGCCTCTGGCCTCTAGGTAACCAGTTTAAATTGCTTCAGGGTGATA
ACTACTTAGCACTGCCCTGGTGATTACCCAGAGATATCTATGAAAACCAGTG
GCTTCCATCAAACCTTTGCCAACTCAGGTTCACAGCAGCTTTGGGCAGTTAT
GGCAGTATGGCATTAGCTGAGAGGTGTCTGCCACTTCTGGGTCAATGGAATA
ATAAATTAAGTACAGGCAGGAATTTGGTTGGGAGCATCTTGTATGATCTCCG
TATGATGTGATATTGATGGAGATAGTGGTCCTCATTCTTGGGGGTTGCCATT
CCCACATTCCCCCTTCAACAAACAGTGTAACAGGTCCTTCCCAGATTTAGGG
TACTTTTATTGATGGATATGTTTTCCTTTTATTCACATAACCCCTTGAAACCC
TGTCTTGTCCTCCTGTTACTTGCTTCTGCTGTACAAGATGTAGCACCTTTTCT
CCTCTTTGAACATGGTCTAGTGACACGGTAGCACCAGTTGCAGGAAGGAGC
CAGACTTGTTCTCAGAGCACTGTGTTCACACTTTTCAGCAAAAATAGCTATG
GTTGTAACATATGTATTCCCTTCCTCTGATTTGAAGGCAAAAATCTACAGTG
TTTCTTCACTTCTTTTCTGATCTGGGGCATGAAAAAAGCAAGATTGAAATTT
GAACTATGAGTCTCCTGCATGGCAACAAAATGTGTGTCACCATCAGGCCAA
CAGGCCAGCCCTTGAATGGGGATTTATTACTGTTGTATCTATGTTGCATGAT
AAACATTCATCACCTTCCTCCTGTAGTCCTGCCTCGTACTCCCCTTCCCCTAT
GATTGAAAAGTAAACAAAACCCACATTTCCTATCCTGGTTAGAAGAAAATT
AATGTTCTGACAGTTGTGATCGCCTGGAGTACTTTTAGACTTTTAGCATTCGT
TTTTTACCTGTTTGTGGATGTGTGTTTGTATGTGCATACGTATGAGATAGGCA
CATGCATCTTCTGTATGGACAAAGGTGGGGTACCTACAGGAGAGCAAAGGT
TAATTTTGTGCTTTTAGTAAAAACATTTAAATACAAAGTTCTTTATTGGGTGG
AATTATATTTGATGCAAATATTTGATCACTTAAAACTTTTTAAAACTTCTAGGT
AATTTGCCACGCTTTTTGACTGCTCACCAATACCCTGTAAAAATACGTAATT
CTTCCTGTTTGTGTAATAAGATATTCATATTTGTAGTTGCATTAATAATAGTT
ATTTCTTAGTCCATCAGATGTTCCCGTGTGCCTCTTTTATGCCAAATTGATTG
TCATATTTCATGTTGGGACCAAGTAGTTTGCCCATGGCAAACCTAAATTTAT
GACCTGCTGAGGCCTCTCAGAAAACTGAGCATACTAGCAAGACAGCTCTTCT
TGAAAAAAAAAATATGTATACACAAATATATACGTATATCTATATATACGTA
TGTATATATACACACATGTATATTCTTCCTTGATTGTGTAGCTGTCCAAAATAAT
AACATATATAGAGGGAGCTGTATTCCTTTATACAAATCTGATGGCTCCTGCA
GCACTTTTTCCTTCTGAAAATATTTACATTTTGCTAACCTAGTTTGTTACTTT
AAAAATCAGTTTTGATGAAAGGAGGGAAAAGCAGATGGACTTGAAAAAGA
TCCAAGCTCCTATTAGAAAAGGTATGAAAATCTTTATAGTAAAATTTTTTAT
AAACTAAAGTTGTACCTTTTAATATGTAGTAAACTCTCATTTATTTGGGGTTC
GCTCTTGGATCTCATCCATCCATTGTGTTCTCTTTAATGCTGCCTGCCTTTTG
AGGCATTCACTGCCCTAGACAATGCCACCAGAGATAGTGGGGGAAATGCCA
GATGAAACCAACTCTTGCTCTCACTAGTTGTCAGCTTCTCTGGATAAGTGAC
CACAGAAGCAGGAGTCCTCCTGCTTGGGCATCATTGGGCCAGTTCCTTCTCT
TTAAATCAGATTTGTAATGGCTCCCAAATTCCATCACATCACATTTAAATTG
CAGACAGTGTTTTGCACATCATGTATCTGTTTTGTCCCATAATATGCTTTTTA
CTCCCTGATCCCAGTTTCTGCTGTTGACTCTTCCATTCAGTTTTATTTATTGTG
TGTTCTCACAGTGACACCATTTGTCCTTTTCTGCAACAACCTTTCCAGCTACT
TTTGCCAAATTCTATTTGTCTTCTCCTTCAAAATTCTCCTTTGCAGTTCCTC
TTCATCTGTGTAGCTGCTCTTTTGTCTCTTAACTTACCATTCCTATAGTACTTT
ATGCATCTCTGCTTAGTTCTATTAGTTTTTTGGCCTTGCTCTTCTCCTTGATTT
TAAAATTCCTTCTATAGCTAGAGCTTTTCTTTCTTTCATTCTCTCCTGCAG
TGTTTTGCATACATCAGAAGCTAGGTACATAAGTTAAATGATTGAGAGTTGG
CTCTATTTAGATTTATCACTTTTTAATAGGGTGAGCTTGAGAGTTTTCTTTCT
TTCTGTTTTTTTTTTGTTTTTTTTTTTTTTTTTTTTTTTTTTGACTAA
TTTCACATGCTCTAAAAACCTTCAAAGGTGATTATTTTTCTCCTGGAAACTCC
AGGTCCATTCTGTTTAAATCCCTAAGAATGTCAGAATTAAAATAACAGGGCT TABLE 3-continued

```
ATCCCGTAATTGGAAATATTTCTTTTTTCAGGATGCTATAGTCAATTTAGTAA
GTGACCACCAAATTGTTATTTGCACTAACAAAGCTCAAAACACGATAAGTTT
ACTCCTCCATCTCAGTAATAAAAATTAAGCTGTAATCAACCTTCTAGGTTTC
TCTTGTCTTAAAATGGGTATTCAAAAATGGGGATCTGTGGTGTATGTATGGA
AACACATAGTCCTTAATTTACCTGTTGTTGGAAACTGGAGAAATGATTGTCG
GGCAACCGTTTATTTTTATTGTATTTTATTTGGTTGAGGGATTTTTTTATAA
ACAGTTTTACTTGTGTCATATTTTAAAATTACTAACTGCCATCACCTGCTGGG
GTCCTTTGTTAGGTCATTTTCAGTGACTAATAGGGATAATCCAGGTAACTTT
GAAGAGATGAGCAGTGAGTGACCAGCCAGTTTTTCTGCCTTTAGCTTTGACA
GTTCTTAATTAAGATCATTGAAGACCAGCTTTCTCATAAATTTCTCTTTTTGA
AAAAAAGAAAGCATTTGTACTAAGCTCCTCTGTAAGACAACATCTTAAATCT
TAAAAGTGTTGTTATCATGACTGGTGAGAGAAGAAAACATTTTGTTTTTATT
AAATGGAGCATTATTTACAAAAAGCCATTGTTGAGAATTAGATCCCACATCG
TATAAATATCTATTAACCATTCTAAATAAAGAGAACTCCAGTGTTGCTATGT
GCAAGATCCTCTCTTGGAGCTTTTTTGCATAGCAATTAAAGGTGTGCTATTT
GTCAGTAGCCATTTTTTCCAGTGATTTGAAGACCAAAGTTGTTTTACAGCT
GTGTTACCGTTAAAGGTTTTTTTTTTATATGTATTAAATCAATTTATCACTG
TTTAAAGCTTTGAATATCTGCAATCTTTGCCAAGGTACTTTTTTATTTAAAAA
AAAACATAACTTTGTAAATATTACCCTGTAATATTATATATACTTAATAAAA
CATTTTAAGCTA (SEQ ID NO: 13)
```

Human CD47 amino acid isoform 3 (XP_005247965.1)
MWPLVAALLLGSACCGSA**QLLFNKTKSVEFTFCNDTVVIPCFVTNMEAQNT
TEVYVKWKFKGRDIYTFDGALNKSTVPTDFSSAKIEVSQLLKGDASLKMDK
SDAVSHTGNYTCEVTELTREGETIIELKYRVVSWFSPNE**NILIVIFPIFAILLFW
GQFGIKTLKYRSGGMDEKTIALLVAGLVITVIVIVGAILFVPGEYSLKNATGLGLI
VTSTGILILLHYYVFSTAIGLTSFVIAILVIQVIAYILAVVGLSLCIAACIPMHGPLLI
SGLSILALAQLLGLVYMKFV*ASNQKTIQPPPRKAVEEPLNE* (SEQ ID NO: 14)

Human CD47 mRNA isoform 4 (NM_001777.3)
```
GGGGAGCAGGCGGGGGAGCGGGCGGGAAGCAGTGGGAGCGCGCGTGCGCG
CGGCCGTGCAGCCTGGGCAGTGGGTCCTGCCTGTGACGCGCGGCGGCGGTC
GGTCCTGCCTGTAACGGCGGCGGCGGCTGCTGCTCCAGACACCTGCGGCGG
CGGCGGCGACCCCGCGGCGGGCGCGGAG**ATGTGGCCCCTGGTAGCGGCG
CTGTTGCTGGGCTCGGCGTGCTGCGGATCAGCTCAGCTACTATTTAATA
AAACAAAATCTGTAGAATTCACGTTTTGTAATGACACTGTCGTCATTCC
ATGCTTTGTTACTAATATGGAGGCACAAAACACTACTGAAGTATACGTA
AAGTGGAAATTTAAAGGAAGAGATATTTACACCTTTGATGAGCTCTAA
ACAAGTCCACTGTCCCCACTGACTTTAGTAGTGCAAAAATTGAAGTCTC
ACAATTACTAAAAGGAGATGCCTCTTTTGAAGATGGATAAGAGTGATGCT
GTCTCACACACAGGAAACTACACTTGTGAAGTAACAGAATTAACCAGAG
AAGGTGAAACGATCATCGAGCTAAAATATCGTGTTGTTTCATGGTTTTC
TCCAAATGAAAATATTCTTATTGTTATTTTCCCAATTTTTGCTATACTCC
TGTTCTGGGGACAGTTTGGTATTAAAACACTTAAATATAGATCCGGTGG
TATGGATGAGAAAACAATTGCTTTACTTGTTGCTGGACTAGTGATCACT
GTCATTGTCATTGTTGGAGCCATTCTTTTCGTCCCAGGTGAATATTCATT
AAAGAATGCTACTGGCCTTGGTTTAATTGTGACTTCTACAGGGATATTA
ATATTACTTCACTACTATGTGTTTAGTACAGCGATTGGATTAACCTCCTT
CGTCATTGCCATATTGGTTATTCAGGTGATAGCCTATATCCTCGCTGTG
GTTGGACTGAGTCTCTGTATTGCGGCGTGTATACCAATGCATGGCCCTC
TTCTGATTTCAGGTTTGAGTATCTTAGCTCTAGCACAATTACTTGGACTA
GTTTATATGAAATTTGTGGCTTCCAATCAGAAGACTATACAACCTCCTA
GGAAAGCTGTAGAGGAACCCCTTAATGCATTCAAAGAATCAAAAGGAAT
GATGAATGATGAATAACTGA**AGTGAAGTGATGGACTCCGATTTGGAGAGT
AGTAAGACGTGAAAGGAATACACTTGTGTTTAAGCACCATGGCCTTGATGA
TTCACTGTTGGGGAGAAGAAACAAGAAAAGTAACTGGTTGTCACCTATGAG
ACCCTTACGTGATTGTTAGTTAAGTTTTTATTCAAAGCAGCTGTAATTTAGTT
AATAAAATAATTATGATCTATGTTGTTTGCCCAATTGAGATCCAGTTTTTGT
TGTTATTTTAATCAATTAGGGGCAATAGTAGAATGGACAATTTCCAAGAAT
GATGCCTTTCAGGTCCTAGGGCCTCTGGCCTCTAGGTAACCAGTTTAAATTG
GTTCAGGGTGATAACTACTTAGCACTGCCCTGGTGATTACCCAGAGATATCT
ATGAAAACCAGTGGCTTCCATCAAACCTTTGCCAACTCAGGTTCACAGCAGC
TTTGGGCAGTTATGGCAGTATGGCATTAGCTGAGAGGTGTCTGCCACTTCTG
GGTCAATGGAATAATAAATTAAGTACAGGCAGGAATTTGGTTGGGAGCATC
TTGTATGATCTCCGTATGATGTGATATTGATGGAGATAGTGGTCCTCATTCTT
GGGGGTTGCCATTCCCACATTCCCCCTTCAACAAACAGTGTAACAGGTCCTT
CCCAGATTTAGGGTACTTTTATTGATGGATATGTTTTCCTTTTATTCACATAA
CCCCTTGAAACCCTGTCTTGTCCTCCTGTTACTTGCTTCTGCTGTACAAGATG
TAGCACCTTTTCTCCTCTTTGAACATGGTCTAGTGACACGGTAGCACCAGTT
GCAGGAAGGAGCCAGACTTGTTCTCAGAGCACTGTGTTCACACTTTTCAGCA
AAAATAGCTATGGTTGTAACATATGTATTCCCTTCCTCTGATTTGAAGGCAA
AAATCTACAGTGTTTCTTCACTTCTTTTCTGATCTGGGGCATGAAAAAAGCA
AGATTGAAATTTGAACTATGAGTCTCCTGCATGGCAACAAAATGTGTGTCAC
CATCAGGCCAACAGGCCAGCCCTTGAATGGGGATTTATTACTGTTGTATCTA
TGTTGCATGATAAACATTCATCACCTTCCTCCTGTAGTCCTGCCTCGTACTCC
CCTTCCCCTATGATTGAAAAGTAAACAAAACCCACATTTCCTATCCTGGTTA
GAAGAAAATTAATGTTCTGACAGTTGTGATCGCCTGGAGTACTTTTAGACTT
TTAGCATTCGTTTTTTACCTGTTTGTGGATGTGTGTTTGTATGTGCATACGTA
TGAGATAGGCACATGCATCTTCTGTATGGACAAAGGTGGGGTACCTACAGG
AGAGCAAAGGTTAATTTTGTGCTTTTAGTAAAAACATTTAAATACAAAGTTC
```

TABLE 3-continued

```
TTTATTGGGTGGAATTATATTTGATGCAAATATTTGATCACTTAAAACTTTTA
AAACTTCTAGGTAATTTGCCACGCTTTTTGACTGCTCACCAATACCCTGTAA
AAATACGTAATTCTTCCTGTTTGTGTAATAAGATATTCATATTTGTAGTTGCA
TTAATAATAGTTATTTCTTAGTCCATCAGATGTTCCCGTGTGCCTCTTTTATG
CCAAATTGATTGTCATATTTCATGTTGGGACCAAGTAGTTTGCCCATGGCAA
ACCTAAATTTATGACCTGCTGAGGCCTCTCAGAAAACTGAGCATACTAGCAA
GACAGCTCTTCTTGAAAAAAAAAATATGTATACACAAATATATACGTATATC
TATATATACGTATGTATATACACACATGTATATTCTTCCTTGATTGTGTAGCT
GTCCAAAATAATAACATATATAGAGGGAGCTGTATTCCTTTATACAAATCTG
ATGGCTCCTGCAGCACTTTTTCCTTCTGAAAATATTTACATTTTGCTAACCTA
GTTTGTTACTTTAAAAATCAGTTTTGATGAAAGGAGGGAAAAGCAGATGGA
CTTGAAAAAGATCCAAGCTCCTATTAGAAAAGGTATGAAAATCTTTATAGTA
AAATTTTTTATAAACTAAAGTTGTACCTTTTAATATGTAGTAAACTCTCATTT
ATTTGGGGTTCGCTCTTGGATCTCATCCATCCATTGTGTTCTCTTTAATGCTG
CCTGCCTTTTGAGGCATTCACTGCCCTAGACAATGCCACCAGAGATAGTGGG
GGAAATGCCAGATGAAACCAACTCTTGCTCTCACTAGTTGTCAGCTTCTCTG
GATAAGTGACCACAGAAGCAGGAGTCCTCCTGCTTGGGCATCATTGGGCCA
GTTCCTTCTCTTTAAATCAGATTTGTAATGGCTCCCAAATTCCATCACATCAC
ATTTAAATTGCAGACAGTGTTTTGCACATCATGTATCTGTTTTGTCCCATAAT
ATGCTTTTTACTCCCTGATCCCAGTTTCTGCTGTTGACTCTTCCATTCAGTTTT
ATTTATTGTGTGTTCTCACAGTGACACCATTTGTCCTTTTCTGCAACAACCTT
TCCAGCTACTTTTGCCAAATTCTATTTGTCTTCTCCTTCAAAACATTCTCCTTT
GCAGTTCCTCTTCATCTGTGTAGCTGCTCTTTTGTCTCTTAACTTACCATTCCT
ATAGTACTTTATGCATCTCTGCTTAGTTCTATTAGTTTTTTGGCCTTGCTCTTC
TCCTTGATTTTAAAATTCCTTCTATAGCTAGAGCTTTTCTTTCTTTCATTCTCT
CTTCCTGCAGTGTTTTGCATACATCAGAAGCTAGGTACATAAGTTAAATGAT
TGAGAGTTGGCTGTATTTAGATTTATCACTTTTTAATAGGGTGAGCTTGAGA
GTTTTCTTTCTTCTGTTTTTTTTTTTGTTTTTTTTTTTTTTTTTTTTTTTTTT
TTTTGACTAATTTCACATGCTCTAAAAACCTTCAAAGGTGATTATTTTTCTCC
TGGAAACTCCAGGTCCATTCTGTTTAAATCCCTAAGAATGTCAGAATTAAAA
TAACAGGGCTATCCCGTAATTGGAAATATTTCTTTTTTCAGGATGCTATAGT
CAATTTAGTAAGTGACCACCAAATTGTTATTTGCACTAACAAAGCTCAAAAC
ACGATAAGTTTACTCCTCCATCTCAGTAATAAAAATTAAGCTGTAATCAACC
TTCTAGGTTTCTCTTGTCTTAAAATGGGTATTCAAAAATGGGGATCTGTGGT
GTATGTATGGAAACACATACTCCTTAATTTACCTGTTGTTGGAAACTGGAGA
AATGATTGTCGGGCAACCGTTTATTTTTATTGTATTTTATTTGGTTGAGGGA
TTTTTTTTATAAACAGTTTTACTTGTGTCATATTTAAAATTACTAACTGCCAT
CACCTGCTGGGGTCCCTTTGTTAGGTCATTTTCAGTGACTAATAGGGATAATC
CAGGTAACTTTGAAGAGATGAGCAGTGAGTGACCAGGCAGTTTTTCTGCCTT
TAGCTTTGACAGTTCTTAATTAAGATCATTGAAGACCAGCTTTCTCATAAAT
TTCTCTTTTTGAAAAAAAGAAAGCATTTGTACTAAGCTCCTCTGTAAGACAA
CATCTTAAATCTTAAAAGTGTTGTTATCATGACTGGTGAGAGAAGAAAACAT
TTTGTTTTTATTAAATGGAGCATTATTTACAAAAAGCCATTGTTGAGAATTA
GATCCCACATCGTATAAATATCTATTAACCATTCTAAATAAAGAGAACTCCA
GTGTTGCTATGTGCAAGATCCTCTCTTGGAGCTTTTTGCATAGCAATTAAA
GGTGTGCTATTTGTCAGTAGCCATTTTTTGCAGTGATTTGAAGACCAAAGT
TGTTTTACAGCTGTGTTACCGTTAAAGGTTTTTTTTTTATATGTATTAAATC
AATTTATCACTGTTTAAAGCTTTGAATATCTGCAATCTTTGCCAAGGTACTTT
TTTATTTAAAAAAAAACATAACTTTGTAAATATTACCCTGTAATATTATATAT
ACTTAATAAAACATTTTAAGCTATTTTGTTGGGCTATTTCTATTGCTGCTACA
GCAGACCACAAGCACATTTCTGAAAAATTTAATTTATTAATGTATTTTTAAG
TTGCTTATATTCTAGGTAACAATGTAAAGAATGATTTAAAATATTAATTATG
AATTTTTTGAGTATAATACCCAATAAGCTTTTAATTAGAGCAGAGTTTTAATT
AAAAGTTTTAAATCAGTC (SEQ ID NO: 15)

Human CD47 amino acid isoform 4 (NP_001768.1)
MWPLVAALLLGSACCGSA**QLLFNKTKSVEFTFCNDTVVIPCFVTNMEAQNT
TEVYVKWKFKFKGRDIYTFDGALNKSTVPTDFSSAKIEVSQLLKGDASLKMDK
SDAVSHTGNYTCEVTELTREGETIIELKYRVVSWFSPNE**NILIVIFPIFAILLFW
GQFGIKTLKYRSGGMDEKTIALLVAGLVITVIVIVGAILFVPGEYSLKNATGLGLI
VTSTGILILLHYYVFSTAIGLTSFVIAILVIQVIAYILAVVGLSLCIAACIPMHGPLLI
SGLISILALAQLLGLVYMKFV*ASNQKTIQPPRKAVEEPLNAFKESKGMMNDE* (SEQ
ID NO: 16)

Humanized CD47 amino acid isoform 1
MWPLAAALLLGSCCC**GSAQLLFNKTKSVEFTFCNDTVVIPCFVTNMEAQNT
TEVYVKWKFKFKGRDIYTFDGALNKSTVFTDFSSAKIEVSQLLKGDASLKMDK
SDAVSHTGNYTCEVTELTREGETIIELKYRVVSWFSPNENILIVIFPIFAILLF
WGQFGIKTLKYRSGGMDEKTIALLVAGLVITVIVIVGAILFVPGEYSLKNAT
GLGLIVTSTGILILLHYYVFSTAIGLTSFVIAILVIQVIAYILAVVGLSLCIAACI
PMHGPLLISGLSILALAQLLGLVYMKFV***E*** (SEQ ID NO: 17)

Humanized CD47 amino acid isoform 2
MWPLAAALLLGSCCC**GSAQLLFNKTKSVEFTFCNDTVVIPCFVTNMEAQNT
TEVYVKWKFKFKGRDIYTFDGALNKSTVPTDFSSAKIEVSQLLKGDASLKMDK
SDAVSHTGNYTCEVTELTREGETIIELKYRVVSWFSPNENILIVIFPIFAILLF
WGQFGIKTLKYRSGGMDEKIIALLVAGLVITVIVIVGAILFVPGEYSLKNAT
GLGLIVTSTGILILLHYYVFSTAIGLTSFVIAILVIQVIAYILAVVGLSLCIAACI
PMHGPLLISGLSILALAQLLGLVYMKFV***ASNQRTIQPPRNR***(SEQ ID NO: 18)
```

TABLE 3-continued

Humanized CD47 amino acid isoform 3
MWPLAAALLLGSCCCGSAQLLFNKTKSVEFTFCNDTVVIPCFVTNMEAQNT
TEVYVKWKFKGRDIYTFDGALNKSTVPTDFSSAKIEVSQLLKGDASLKMDK
SDAVSHTGNYTCEVTELTREGETIIELKYRVVSWFSPNENILIVIFPIFAILLF
WGQFGIKTLKYRSGGMDEKTIALLVAGLVITVIVIVGAILFVPGEYSLKNAT
GLGLIVTSTGILILLHYYVFSTAIGLTSFVIAILVIQVIAYILAVVGLSLCIAACI
PMHGPLLISGLSILALAQLLGLVYMKFVASNQRTIQPPRKAVEEPLNE (SEQ ID
NO: 19)

Humanized CD47 amino acid isoform 4
MWPLAAALLLGSCCCGSAQLLFNKTKSVEFTFCNDTVVIPCFVTNMEAQNT
TEVYVKWKFKGRDIYTFDGALNKSTVPTDFSSAKIEVSQLLKGDASLKMDK
SDAVSHTGNYTCEVTELTREGETIIELKYRVVSWFSPNENILIVIFPIFAILLF
WGQFGIKTLKYRSGGMDEKTIALLVAGLVITVIVIVGAILFVPGEYSLKNAT
GLGLIVTSTGILILLHYYVFSTAIGLTSFVIAILVIQVIAYILAVVGLSLCIAACI
PMHGPLLISGLSILALAQLLGLVYMKFVASNQRTIQPPRKAVEEPLNAFKESKG
MMNDE (SEQ ID NO: 20)

Humanized CD47 Non-Human Animals

Non-human animals are provided that express humanized CD47 proteins on the surface of cells of the non-human animals resulting from a genetic modification of an endogenous locus of the non-human animal that encodes a CD47 protein. Suitable examples described herein include rodents, in particular, mice.

A humanized CD47 gene, in some embodiments, comprises genetic material from a heterologous species (e.g., humans), wherein the humanized CD47 gene encodes a CD47 protein that comprises the encoded portion of the genetic material from the heterologous species. In some embodiments, a humanized CD47 gene of the present invention comprises genomic DNA of a heterologous species that encodes the extracellular portion of a CD47 protein that is expressed on the plasma membrane of a cell. In some embodiments, a humanized CD47 gene of the present invention comprises genomic DNA of a heterologous species that encodes the extracellular portion and the transmembrane portion of a CD47 protein that is expressed on the plasma membrane of a cell. Non-human animals, embryos, cells and targeting constructs for making non-human animals, non-human embryos, and cells containing said humanized CD47 gene are also provided.

In some embodiments, an endogenous CD47 gene is deleted. In some embodiments, an endogenous CD47 gene is altered, wherein a portion of the endogenous CD47 gene is replaced with a heterologous sequence (e.g., a human CD47 sequence, in whole or in part). In some embodiments, all or substantially all of an endogenous CD47 gene is replaced with a heterologous gene (e.g., a human CD47 gene). In some embodiments, a portion of a heterologous CD47 gene is inserted into an endogenous non-human CD47 gene at an endogenous CD47 locus. In some embodiments, the heterologous gene is a human gene. In some embodiments, the modification or humanization is made to one of the two copies of the endogenous CD47 gene, giving rise to a non-human animal that is heterozygous with respect to the humanized CD47 gene. In other embodiments, a non-human animal is provided that is homozygous for a humanized CD47 gene.

A non-human animal of the present invention contains a human CD47 gene, in whole or in part, at an endogenous non-human CD47 locus. Thus, such non-human animals can be described as having a heterologous CD47 gene. The replaced, inserted, modified or altered CD47 gene at the endogenous CD47 locus can be detected using a variety of methods including, for example, PCR, Western blot, Southern blot, restriction fragment length polymorphism (RFLP), or a gain or loss of allele assay. In some embodiments, the non-human animal is heterozygous with respect to the humanized CD47 gene. In some embodiments, the non-human animal is homozygous for the humanized CD47 gene.

In various embodiments, a humanized CD47 gene according to the present invention includes a CD47 gene that has a second, third, fourth, fifth, sixth and seventh exon each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a second, third, fourth, fifth, sixth and seventh exon that appear in a human CD47 gene of Table 3.

In various embodiments, a humanized CD47 gene according to the present invention includes a CD47 gene that has a first exon and exon(s) downstream of exon 7 (e.g., eighth and ninth exons of isoform 2) each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a respective exon that appears in a mouse CD47 gene of Table 3.

In various embodiments, a humanized CD47 gene according to the present invention includes a CD47 gene that has a 5' untranslated region and a 3' untranslated region each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a 5' untranslated region and a 3' untranslated region that appear in a mouse CD47 gene of Table 3.

In various embodiments, a humanized CD47 gene according to the present invention includes a CD47 gene that has a nucleotide coding sequence (e.g., a cDNA sequence) at least 50% (e.g., 50%, 55%, 60%, 65%, 70%, 75%, 80%, 85%, 90%, 91%, 92%, 93%, 94%, 95%, 96%, 97%, 98%, 99% or more) identical to a nucleotide coding sequence that appears in a human CD47 nucleotide coding sequence of Table 3.

In various embodiments, a humanized CD47 protein produced by a non-human animal of the present invention has an extracellular portion having an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an extracellular portion of a human CD47 protein that appears in Table 3.

In various embodiments, a humanized CD47 protein produced by a non-human animal of the present invention has an extracellular portion having an amino acid sequence that is identical to amino acid residues 19-141 that appear in a human CD47 protein of Table 3.

In various embodiments, a humanized CD47 protein produced by a non-human animal of the present invention has an N-terminal immunoglobulin V domain having an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an N-terminal immunoglobulin V domain of a human CD47 protein that appears in Table 3.

In various embodiments, a humanized CD47 protein produced by a non-human animal of the present invention has an N-terminal immunoglobulin V domain having an amino acid sequence that is identical to amino acid residues 19-127 that appear in a human CD47 protein of Table 3.

In various embodiments, a humanized CD47 protein produced by a non-human animal of the present invention has an N-terminal immunoglobulin V domain and five transmembrane domains each having a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an N-terminal immunoglobulin V domain and five transmembrane domains of a human CD47 protein that appears in Table 3.

In various embodiments, a humanized CD47 protein produced by a non-human animal of the present invention has an intracytoplasmic tail having a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an intracytoplasmic tail of a mouse CD47 protein that appears in Table 3.

In various embodiments, a humanized CD47 protein produced by a non-human animal of the present invention has an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 16-292 that appear in a human CD47 protein of Table 3.

In various embodiments, a humanized CD47 protein produced by a non-human animal of the present invention has an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 19-292 that appear in a human CD47 protein of Table 3.

In various embodiments, a humanized CD47 protein produced by a non-human animal of the present invention has an amino acid sequence that is identical to amino acid residues 19-292 (or 16-292) that appear in a human CD47 protein of Table 3.

In various embodiments, a humanized CD47 protein produced by a non-human animal of the present invention has an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an amino acid sequence of a humanized CD47 protein that appears in Table 3.

In various embodiments, a humanized CD47 protein produced by a non-human animal of the present invention has an amino acid sequence that is identical to an amino acid sequence of a humanized CD47 protein that appears in Table 3.

Compositions and methods for making non-human animals that express a humanized CD47 protein, including specific polymorphic forms, allelic variants (e.g., single amino acid differences) or alternatively spliced isoforms, are provided, including compositions and methods for making non-human animals that express such proteins from a human promoter and a human regulatory sequence. In some embodiments, compositions and methods for making non-human animals that express such proteins from an endogenous promoter and an endogenous regulatory sequence are also provided. The methods include inserting the genetic material encoding a human CD47 protein in whole or in part at a precise location in the genome of a non-human animal that corresponds to an endogenous CD47 gene thereby creating a humanized CD47 gene that expresses a CD47 protein that is human in whole or in part. In some embodiments, the methods include inserting genomic DNA corresponding to exons 2-7 of a human CD47 gene into an endogenous CD47 gene of the non-human animal thereby creating a humanized gene that encodes a CD47 protein that contains a human portion containing amino acids encoded by the inserted exons.

Where appropriate, the coding region of the genetic material or polynucleotide sequence(s) encoding a human CD47 protein in whole or in part may be modified to include codons that are optimized for expression in the non-human animal (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding a human CD47 protein, in whole or in part, may include an altered sequence to optimize codon usage for a particular cell type (e.g., a rodent cell). For example, the codons of the genomic DNA corresponding to exons 2-7 of a human CD47 gene to be inserted into an endogenous CD47 gene of a non-human animal (e.g., a rodent) may be optimized for expression in a cell of the non-human animal. Such a sequence may be described as a codon-optimized sequence.

A humanized CD47 gene approach employs a relatively minimal modification of the endogenous gene and results in natural CD47-mediated signal transduction in the non-human animal, in various embodiments, because the genomic sequence of the CD47 sequences are modified in a single fragment and therefore retain normal functionality by including necessary regulatory sequences. Thus, in such embodiments, the CD47 gene modification does not affect other surrounding genes or other endogenous CD47-interacting genes (e.g., thrombospondin, SIRPs, integrins, etc.). Further, in various embodiments, the modification does not affect the assembly of a functional CD47 transmembrane protein on the plasma membrane and maintains normal effector functions via binding and subsequent signal transduction through the cytoplasmic portion of the protein which is unaffected by the modification.

A schematic illustration (not to scale) of the genomic organization of an endogenous murine CD47 gene and a human CD47 gene is provided in FIG. 1. An exemplary method for humanizing an endogenous murine CD47 gene using a genomic fragment containing exons 2-7 of a human CD47 gene is provided in FIG. 2. As illustrated, genomic DNA containing exons 2-7 of a human CD47 gene is inserted into an endogenous murine CD47 gene locus by a targeting construct. This genomic DNA includes the portion of the gene that encodes an extracellular portion and transmembrane domains (e.g., amino acid resides 16-292) of a human CD47 protein responsible for ligand binding.

Figure 2:
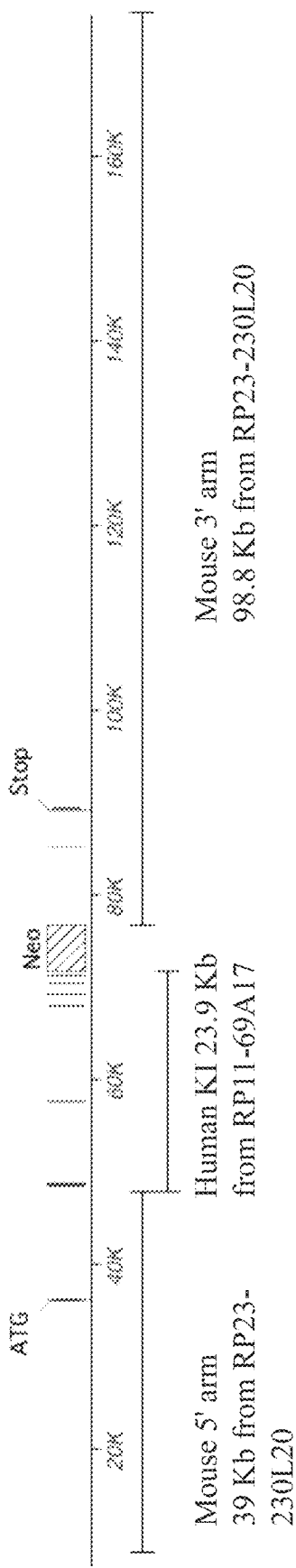
FIG. 2 shows a diagram, not to scale, of an exemplary method for humanization of a non-human Cluster of Differentiation 47 (CD47) gene.
Figure 2:
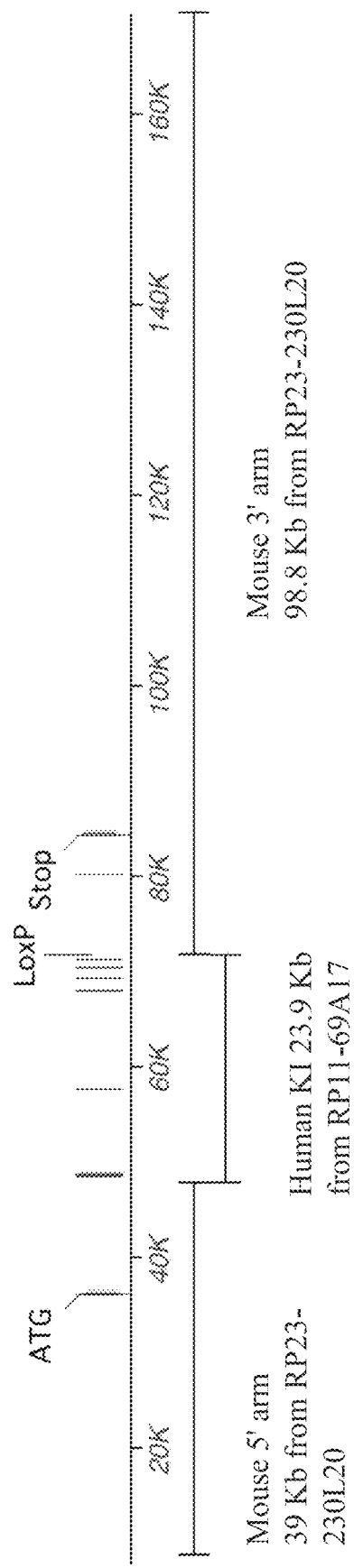

A non-human animal (e.g., a mouse) having a humanized CD47 gene at the endogenous CD47 locus can be made by any method known in the art. For example, a targeting vector can be made that introduces a human CD47 gene in whole or in part with a selectable marker gene. FIG. 2 illustrates an endogenous CD47 locus of a mouse genome comprising an insertion of exons 2-7 of a human CD47 gene. As illustrated, the targeting construct contains a 5' homology arm containing sequence upstream of exon 2 of an endogenous murine CD47 gene (~39 Kb), followed by a genomic DNA fragment containing exons 2-7 of a human CD47 gene (~23.9 Kb), a drug selection cassette (e.g., a neomycin resistance gene flanked on both sides by loxP sequences; ~5 Kb), and a 3' homology arm containing sequence downstream of exon7 of an endogenous murine CD47 gene (~99 Kb). The targeting construct contains a self-deleting drug selection cassette (e.g., a neomycin resistance gene flanked by loxP sequences: see U.S. Pat. Nos. 8,697,851, 8,518,392 and 8,354,389, all of which are incorporated herein by reference). Upon homologous recombination, exons 2-7 of an endogenous murine CD47 gene are replaced by the sequence contained in the targeting vector (i.e., exons 2-7 of a human CD47 gene). A humanized CD47 gene is created resulting in a cell or non-human animal that expresses a humanized CD47 protein that contains amino acids encoded by exons 2-7 of a human CD47 gene. The drug selection cassette is removed in a development-dependent manner, i.e., progeny derived from mice whose germ line cells containing the humanized CD47 gene described above will shed the selectable marker from differentiated cells during development.

The non-human animals of the present invention may be prepared as described above, or using methods known in the art, to comprise additional human or humanized genes, oftentimes depending on the intended use of the non-human animal. Genetic material of such additional human or humanized genes may be introduced through the further alteration of the genome of cells (e.g., embryonic stem cells) having the genetic modifications as described above or through breeding techniques known in the art with other genetically modified strains as desired. In some embodiments, non-human animals of the present invention are prepared to further comprise one or more human or humanized genes selected from SIRPα (CD172a), IL-3, M-CSF, GM-CSF and TPO. In some embodiments, non-human animals of the present invention may be prepared by introducing a targeting vector, as described herein, into a cell from a modified strain. To give but one example, a targeting vector, as described above, may be introduced into a mouse that is Rag2-deficient and IL-2Rγ-deficient and include four human cytokines (Rag2$^{-/-}$IL2Rγc$^{-/-}$; M-CSF$^{Hu}$; IL-3/GM-CSF$^{Hu}$; hSIRPα$^{tg}$; TPO$^{Hu}$). In some embodiments, non-human animals of the present invention are prepared to further comprise a human or humanized signal-regulatory protein alpha (SIRPα) gene. In some embodiments, non-human animals of the present invention comprise a humanized CD47 gene, as described herein, and genetic material from a heterologous species (e.g., humans), wherein the genetic material encodes, in whole or in part, one or more heterologous proteins selected from SIRPα (CD172a), IL-3, M-CSF, GM-CSF and TPO. In some certain embodiments, non-human animals of the present invention comprise a humanized CD47 gene as described herein and genetic material from a heterologous species (e.g., humans), wherein the genetic material encodes, in whole or in part, a heterologous (e.g., human) SIRPα (CD172a) protein. In some certain embodiments, non-human animals of the present invention further comprise a SIRPα gene that comprises an endogenous portion and a human portion (e.g., exons 2-4 of a human SIRPα gene), wherein the human portion encodes the extracellular domain of a SIRPα protein (e.g., amino acids corresponding to residues 28-362 of a human SIRPα protein) and the endogenous portion encodes the intracellular domain of an endogenous SIRPα protein; in some embodiments, the human portion and the endogenous portion are operably linked to an endogenous SIRPα promoter.

For example, as described herein, non-human animals comprising a humanized CD47 gene may further comprise (e.g., via cross-breeding or multiple gene targeting strategies) one or more modifications as described in PCT/US2010/051339, filed Oct. 4, 2010; PCT/US2013/058448, filed Sep. 6, 2013; PCT/US2013/045788, filed Jun. 14, 2013; PCT/US2014/056910, filed Sep. 23, 2014; PCT/US2014/060568, filed Oct. 15, 2014; the PCT/US2012/025040, filed Feb. 14, 2014; PCT/US2012/062379, filed Oct. 29, 2012; PCT/US2014/064806, filed Nov. 10, 2014; and PCT/US2014/064810, filed Nov. 10, 2014; these applications are incorporated herein by reference in their entirety. In certain embodiments, a rodent comprising a humanized CD47 gene (i.e., exons 2-7 of a human CD47 gene operably linked to exon 1 and exon 8 (and hence any downstream exons) of an endogenous rodent CD47 gene so that the humanized CD47 gene encodes a CD47 polypeptide having an extracellular portion from a human CD47 protein and an intracellular portion from a rodent CD47 protein) is crossed to a rodent comprising a humanized SIRPα gene (e.g., exons 2-4 of a human SIRPα gene operably linked to exons 1 and 5-8 of an endogenous rodent SIRPα gene so that the humanized SIRPα gene encodes a SIRPα polypeptide having an extracellular portion from a human SIRPα protein (e.g., amino acids corresponding to residues 28-362) and an intracellular portion from a rodent SIRPα protein; see, e.g., PCT/US2014/056910, filed Sep. 23, 2014, incorporated herein by reference).

Although embodiments employing a humanized CD47 gene in a mouse (i.e., a mouse with a CD47 gene that encodes a CD47 protein that includes a human portion and a mouse portion) are extensively discussed herein, other non-human animals that comprise a humanized CD47 gene are also provided. In some embodiments, such non-human animals comprise a humanized CD47 gene operably linked to an endogenous CD47 promoter. In some embodiments, such non-human animals express a humanized CD47 protein from an endogenous locus, wherein the humanized CD47 protein comprises amino acid residues 16-292 (or 19-141 or 19-127) of a human CD47 protein. Such non-human animals include any of those which can be genetically modified to express a CD47 protein as disclosed herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo.

Methods for modifying a non-human animal genome (e.g., a pig, cow, rodent, chicken, etc. genome) include, e.g., employing a zinc finger nuclease (ZFN) or a transcription activator-like effector nuclease (TALEN) to modify a genome to include a humanized CD47 gene.

In some embodiments, a non-human animal of the present invention is a mammal. In some embodiments, a non-human animal of the present invention is a small mammal, e.g., of the superfamily Dipodoidea or Muroidea. In some embodiments, a genetically modified animal of the present invention is a rodent. In some embodiments, a rodent of the present invention is selected from a mouse, a rat, and a hamster. In some embodiments, a rodent of the present invention is selected from the superfamily Muroidea. In some embodiments, a genetically modified animal of the present invention is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, *Malagasy* rats and mice), Platacanthomyidae (e.g., spiny dormice), and Spalacidae (e.g., mole rates, bamboo rats, and zokors). In some certain embodiments, a genetically modified rodent of the present invention is selected from a true mouse or rat (family Muridae), a gerbil, a spiny mouse, and a crested rat. In some certain embodiments, a genetically modified mouse of the present invention is from a member of the family Muridae. In some embodiment, a non-human animal of the present invention is a rodent. In some certain embodiments, a rodent of the present invention is selected from a mouse and a rat. In some embodiments, a non-human animal of the present invention is a mouse.

In some embodiments, a non-human animal of the present invention is a rodent that is a mouse of a C57BL strain selected from C57BL/A, C57BL/An, C57BL/GrFa, C57BL/KaLwN, C57B/6, C57BL/6J, C57BL/6ByJ, C57BL/6NJ, C57BL/10, C57BL/IOScSn, C57BL/10Cr, and C57BL/Ola. In some certain embodiments, a mouse of the present invention is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing el al., 1999, *Mammalian Genome* 10:836; Auerbach, W. et al., 2000, *Biotechniques* 29(5):1024-1028, 1030, 1032). In some certain embodiments, a genetically modified mouse of the present invention is a mix of an aforementioned 129 strain and an aforementioned C57BL/6 strain. In some certain embodiments, a mouse of the present invention is a mix of aforementioned 129 strains, or a mix of aforementioned BL/6 strains. In some certain embodiments, a 129 strain of the mix as described herein is a 129S6 (129/SvEvTac) strain. In some embodiments, a mouse of the present invention is a BALB strain, e.g., BALB/c strain. In some embodiments, a mouse of the present invention is a mix of a BALB strain and another aforementioned strain.

In some embodiments, a non-human animal of the present invention is a rat. In some certain embodiments, a rat of the present invention is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

Methods Employing Non-Human Animals Having Humanized CD47 Genes

CD47 mutant and transgenic non-human animals (e.g., miniature swine) and cells have been reported (Koshimizu H. et al. (2014) *PLoS One,* 9(2):e89584; Lavender, K. J. et al. (2014) *J. Immunol. Methods,* 407:127-134; Tena, A. et al. (2014) *Am. J. Transplant.* doi: 10.1111/ajt.12918; Lavender K. J. et al. (2013) *Blood,* 122(25):4013-4020; Tena, A. et al. (2012) *Transplantation* 94(10S):776; Wang, C. et al. (2011) *Cell Transplant.* 20(11-12):1915-1920; Johansen, M. L. and Brown, E. J. (2007) *J. Biol. Chem.* 282:24219-24230; Wang, H. et al. (2007) *Proc. Nat. Acad. Sci. U.S.A.* 104:13744-13749; Tulasne D. et al. (2001) *Blood,* 98(12):3346-52; Oldenborg, P. et al. (2000) *Science* 288:2051-2054; Verdrengh, M. et al. (1999) *Microbes Infect.* 1(10):745-751; Chang, H. P. et al. (1999) *Learn Mem.* 6(5):448-457; Wang, X. Q. et al. (1999) *J. Cell Biol.* 147(2):389-400; Lindberg, F. P. et al. (1996) *Science* 274(5288):795-798). Such animals have been employed in a variety of assays to determine, for example, the molecular aspects of CD47 expression, function and regulation. Considerable species differences have been discovered. Indeed, nonobese diabetic/severe combined immunodeficient (NOD/SCID) mice express a SIRPα protein that is capable of interacting with human CD47 and, therefore, have been used extensively for the development of mouse models with components of the human immune system (e.g., see Takenaka, K. et al. (2007) *Nat. Immunol.* 8(120:1313-1323). The SIRPα allele present in these mice is not representative of the SIRPα allele present in other mouse strains and, generally, there is little cross-reaction between CD47 and SIRPα between species. Also, CD47 on mouse cells has been reported to have a near-complete mobility, while CD47 on human cells demonstrate only about 30-40% (Bruce, L. et al. (2003) *Blood* 101:4180-4188; Mouro-Chanteloup, L. et al. (2000) *VoxSanguinis* 78:P030; Mouro-Chanteloup, L. et al. (2003) *Blood* 101:338-344). Thus, NOD/SCID mice are not without limitation. For example, although multi-lineage human hematopoietic development can be supported in some genetic backgrounds (e.g., BALB/c Rag2$^{-/-}$IL-2Rγc$^{-/-}$), homeostasis of other cell types remains inefficient (e.g., T and NK cells; see e.g., Gimeno, R. et al. (2004) *Blood* 104:3886-3893; Traggiai, E. et al. (2004) *Science* 304:104-107; Legrand, N. et al. (2006) *Blood* 108:238-245). Further, CD47 is also known to interact with other cell surface proteins and provide bidirectional signaling. Thus, existing mice represent an inefficient in vivo system for elucidation of CD47-dependent functions in various biological processes such as, for example, engraftment and phagocytosis. Further, existing mice represent a suboptimal in vivo system for development of CD47 targeted therapies.

Non-human animals of the present invention provide an improved in vivo system and source of biological materials (e.g., cells) expressing human CD47 that are useful for a variety of assays. In various embodiments, non-human animals of the present invention are used to develop therapeutics that target CD47 and/or modulate CD47-SIRPα signaling. In various embodiments, non-human animals of the present invention are used to screen and develop candidate therapeutics (e.g., antibodies) that bind human CD47. In various embodiments, non-human animals of the present invention are used to screen and develop candidate therapeutics (e.g., antibodies) that block interaction of human CD47 with human SIRPα. In various embodiments, non-human animals of the present invention are used to determine the binding profile of antagonists and/or agonists of a humanized CD47 on the surface of a cell of a non-human animal as described herein. In some embodiments, non-human animals of the present invention are used to determine the epitope or epitopes of one or more candidate therapeutic antibodies that bind human CD47.

In various embodiments, non-human animals of the present invention are used to determine the pharmacokinetic profiles of anti-CD47 antibodies. In various embodiments, one or more non-human animals of the present invention and one or more control or reference non-human animals are each exposed to one or more candidate therapeutic anti- CD47 antibody at various doses (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mg, 7.5 mg/kg, 10 mg/kg, 15 mg/kg, 20 mg/kg, 25 mg/kg, 30 mg/kg, 40 mg/kg, or 50 mg/kg or more). Candidate therapeutic antibodies may be dosed via any desired route of administration (e.g., subcutaneously, intravenously, intramuscular, intraperitoneal, etc.). Blood is isolated from non-human animals (humanized and control) at various time points (e.g., 0 hr, 6 hr, 1 day, 2 days, 3 days, 4 days, 5 days, 6 days, 7 days, 8 days, 9 days, 10 days, 11 days, or up to 30 or more days). Various assays may be performed to determine the pharmacokinetic profiles of administered candidate therapeutic antibodies using samples obtained from non-human animals as described herein including, but not limited to, total IgG, anti-therapeutic antibody response, agglutination, etc.

In various embodiments, non-human animals of the present invention are used to measure the therapeutic effect of blocking or modulating CD47 signaling and the effect on gene expression as a result of cellular changes. In various embodiments, a non-human animal of the present invention or cells isolated therefrom are exposed to a candidate therapeutic that binds to a humanized CD47 protein (or a human portion of a CD47 protein) on the surface of a cell of the non-human animal and, after a subsequent period of time, analyzed for effects on CD47-dependent processes, for example, adhesion, angiogenesis, apoptosis, inflammation, migration, phagocytosis, proliferation and clearance of tumors (or tumor cells).

Non-human animals of the present invention express humanized CD47 protein, thus cells, cell lines, and cell cultures can be generated to serve as a source of humanized CD47 for use in binding and functional assays, e.g., to assay for binding or function of a CD47 antagonist or agonist, particularly where the antagonist or agonist is specific for a human SIRPα sequence or epitope. In various embodiments, CD47 epitopes bound by candidate therapeutic antibodies can be determined using cells isolated from non-human animals of the present invention.

Cells from non-human animals of the present invention can be isolated and used on an ad hoc basis, or can be maintained in culture for many generations. In various embodiments, cells from a non-human animal of the present invention are immortalized and maintained in culture indefinitely (e.g., in serial cultures).

In various embodiments, cells and/or non-human animals of the present invention are used in a survival and/or proliferation assay (e.g., employing B or T cells) to screen and develop candidate therapeutics that modulate human CD47 signaling. Activation or loss of CD47 can play an important role in the regulation of cell proliferation, and induction of apoptosis by CD47 may result from the activation of specific epitopes of the extracellular domain of CD47, therefore, candidate CD47 modulators (e.g., antagonists or agonists) may be identified, characterized and developed using cells of non-human animals of the present invention and/or a non-human animal as described herein. In some embodiments, cells and/or non-human animals of the present invention are used in survival or death assay(s) to determine the effect on proliferation or apoptosis of a specific cell(s) (e.g., cancer cells) in the presence and absence of CD47.

In various embodiments, cells and/or non-human animals of the present invention are used in xenotransplantation of heterologous (e.g., human) cells to determine the CD47-mediated functions in the physiological (e.g., immune) response to the transplanted human cells. In some embodiments, candidate therapeutics that bind, or block one or more functions of, human CD47 are characterized in a non-human animal of the present invention. Suitable measurements include various cellular assays, proliferation assays, serum immunoglobulin analysis (e.g., antibody titer), cytotoxicity assays, and characterization of ligand-receptor interactions (immunoprecipitation assays). In some embodiments, non-human animals of the present invention are used to characterize the CD47-mediated functions regulating an immune response to an antigen. In some embodiments, the antigen is associated with a neoplasm. In some embodiments, the antigen is associated with an autoimmune disease or condition. In some embodiments, the antigen is a target associated with a disease or condition suffered by one or more human patients in need of treatment.

In various embodiments, non-human animals of the present invention are used in transplantation or adoptive transfer experiments to determine the therapeutic potential of compounds or biological agents to modulate CD47-dependent regulation of new lymphocytes and their immune function. In various embodiments, non-human animals of the present invention are transplanted with human B cells.

In various embodiments, cells of non-human animals of the present invention are used in a cell migration or spreading assay to screen and develop candidate therapeutics that modulate human CD47. Such processes are necessary for many cellular processes including wound healing, differentiation, proliferation and survival.

In various embodiments, cells of non-human animals of the present invention are used in phagocytosis assays to determine the therapeutic potential of compounds or biological agents to modulate CD47-dependent regulation of phagocytosis.

In various embodiments, cells of non-human animals of the present invention are used in tumor cell growth (or proliferation) assays to determine the therapeutic potential of compounds or biological agents to modulate CD47-dependent regulation and/or apoptosis of tumor cells.

In various embodiments, an inflammatory disease or condition is induced in one or more non-human animals of the present invention to provide an in vivo system for determining the therapeutic potential of compounds or biological agents to modulate CD47-dependent regulation of one or more functions of the inflammatory disease or condition. In some embodiments, the inflammatory disease or condition is associated with a neoplasm.

In various embodiments, an anti-angiogenic condition is induced in one or more non-human animals of the present invention to provide an in vivo system for determining the therapeutic potential of compounds or biological agents to modulate CD47-dependent regulation of one or more functions of the anti-angiogenic condition. Exemplary functions that can be evaluated to determine therapeutic efficacy include chemokine expression, nitric oxide (NO)-stimulated responses and blood flow recovery.

Non-human animals of the present invention provide an in vivo system for the analysis and testing of a drug or vaccine. In various embodiments, a candidate drug or vaccine may be delivered to one or more non-human animals of the present invention, followed by monitoring of the non-human animals to determine one or more of the immune response to the drug or vaccine, the safety profile of the drug or vaccine, or the effect on a disease or condition. Exemplary methods used to determine the safety profile include measurements of toxicity, optimal dose concentration, efficacy of the drug or vaccine, and possible risk factors. Such drugs or vaccines may be improved and/or developed in such non-human animals.

Non-human animals of the present invention provide an in vivo system for assessing the pharmacokinetic properties of a drug targeting CD47. In various embodiments, a drug targeting CD47 may be delivered or administered to one or more non-human animals of the present invention, followed by monitoring of, or performing one or more assays on, the non-human animals (or cells isolated therefrom) to determine the effect of the drug on the non-human animal. Pharmacokinetic properties include, but are not limited to, how an animal processes the drug into various metabolites (or detection of the presence or absence of one or more drug metabolites, including, toxic metabolites), drug half-life, circulating levels of drug after administration (e.g., serum concentration of drug), anti-drug response (e.g., anti-drug antibodies), drug absorption and distribution, route of administration, routes of excretion and/or clearance of the drug. In some embodiments, pharmacokinetic and pharmacodynamic properties of drugs (e.g., CD47 modulators) are monitored in or through the use of non-human animals of the present invention.

Non-human animals of the present invention provide an in vivo system for assessing the on-target toxicity of a drug targeting CD47. In various embodiments, a drug targeting CD47 may be delivered or administered to one or more non-human animals of the present invention, followed by monitoring of or performing one or more assays on the non-human animals (or cells isolated therefrom) to determine the on-target toxic effect of the drug on the non-human animal. Typically, drugs are intended to modulate one or more functions of their targets. To give but one example, a CD47 modulator is intended to modulate CD47-mediated functions (e.g., CD47 induced apoptosis) through interacting in some way with the CD47 molecule on the surface of one or more cells. In some embodiments, such a modulator may have an adverse effect that is an exaggeration of the desired pharmacologic action(s) of the modulator. Such effects are termed on-target effects. Exemplary on-target effects include too high of a dose, chronic activation/inactivation, and correct action in an incorrect tissue. In some embodiments, on-target effects of a drug targeting CD47 identified in or through the use of non-human animals of the present invention are used to determine a previously unknown function(s) of CD47.

Non-human animals of the present invention provide an in vivo system for assessing the off-target toxicity of a drug targeting CD47. In various embodiments, a drug targeting CD47 may be delivered or administered to one or more non-human animals of the present invention, followed by monitoring of or performing one or more assays on the non-human animals (or cells isolated therefrom) to determine the off-target toxic effect of the drug on the non-human animal. Off-target effects can occur when a drug interacts with an unintended target (e.g., cross-reactivity to a common epitope). Such interactions can occur in an intended or unintended tissue. To give but one example, mirror image isomers (enantiomers) of a drug can lead to off-target toxic effects. Further, a drug can inappropriately interact with and unintentionally activate different receptor subtypes. Exemplary off-target effects include incorrect activation/inhibition of an incorrect target regardless of the tissue in which the incorrect target is found. In some embodiments, off-target effects of a drug targeting CD47 are determined by comparing the effects of administering the drug to non-human animals of the present invention to one or more reference non-human animals.

In some embodiments, performing an assay includes determining the effect on the phenotype (e.g., change in body weight) and/or genotype of the non-human animal to which the drug is administered. In some embodiments, performing an assay includes determining lot-to-lot variability for a CD47 modulator (e.g., an antagonist or an agonist). In some embodiments, performing an assay includes determining the differences between the effects of a drug targeting CD47 administered to a non-human animal of the present invention and a reference non-human animal. In various embodiments, reference non-human animals may have a modification as described herein, a modification that is different as described herein (e.g., one that has a disruption, deletion or otherwise non-functional CD47 gene) or no modification (i.e., a wild-type non-human animal).

Exemplary parameters that may be measured in non-human animals (or in and/or using cells isolated therefrom) for assessing the pharmacokinetic properties, on-target toxicity, and/or off-target toxicity of a drug targeting CD47 include, but are not limited to, agglutination, autophagy, cell division, cell death, complement-mediated hemolysis, DNA integrity, drug-specific antibody titer, drug metabolism, gene expression arrays, hematocrit levels, hematuria, metabolic activity, mitochondrial activity, oxidative stress, phagocytosis, protein biosynthesis, protein degradation, protein secretion, stress response, target tissue drug concentration, non-target tissue drug concentration, transcriptional activity and the like. In various embodiments, non-human animals of the present invention are used to determine a pharmaceutically effective dose of a CD47 modulator.

Non-human animals of the present invention provide an improved in vivo system for the development and characterization of candidate therapeutics for use in cancer. In various embodiments, non-human animals of the present invention may be implanted with a tumor, followed by administration of one or more candidate therapeutics. In some embodiments, candidate therapeutics may include a multi-specific antibody (e.g., a bi-specific antibody) or an antibody cocktail; in some embodiments, candidate therapeutics include combination therapy such as, for example, administration of mono-specific antibodies dosed sequentially or simultaneously. The tumor may be allowed sufficient time to be established in one or more locations within the non-human animal. Tumor cell proliferation, growth, etc. may be measured both before and after administration with the candidate therapeutic(s). Cytotoxicity of candidate therapeutics may also be measured in the non-human animal as desired.

Non-human animals of the present invention provide improved in vivo system elucidating mechanisms of human cell-to-cell interaction through adoptive transfer. In various embodiments, non-human animals of the present invention may by implanted with a tumor xenograft, followed by a second implantation of tumor infiltrating lymphocytes could be implanted in the non-human animals by adoptive transfer to determine the effectiveness in eradication of solid tumors or other malignancies. Such experiments may be done with human cells due to the exclusive presence of human CD47 without competition with endogenous CD47 of the non-human animal. Alternatively, such experiments may include the use of mouse cells from a NOD/SCID or BRG (BALB/c Rag2IL-2Rγc$^{-/-}$) background. Further, therapies and pharmaceuticals for use in xenotransplantation can be improved and/or developed in such non-human animals.

Non-human animals of the present invention provide an improved in vivo system for maintenance and development of human hematopoietic stem cells through engraftment. In various embodiments, non-human animals of the present invention provide improved development and maintenance of human stem cells within the non-human animal. In various embodiments, increased populations of differentiated human B and T cells are observed in the blood, bone marrow, spleen and thymus of the non-human animal. In various embodiments, optimal T and NK cell homeostasis is observed in cells in the blood, bone marrow, spleen and thymus of the non-human animal. In various embodiments, non-human animals of the present invention demonstrate an increase in the level or amount of red blood cells (RBCs) as compared to one or more reference non-human animals.

Non-human animals of the present invention can be employed to assess the efficacy of a therapeutic drug targeting human cells. In various embodiments, a non-human animal of the present invention is transplanted with human cells, and a drug candidate targeting such human cells is administered to such non-human animal. The therapeutic efficacy of the drug is then determined by monitoring the human cells in the non-human animal after the administration of the drug. Drugs that can be tested in the non-human animals include both small molecule compounds, i.e., compounds of molecular weights of less than 1500 kD, 1200 kD, 1000 kD, or 800 daltons, and large molecular compounds (such as proteins, e.g., antibodies), which have intended therapeutic effects for the treatment of human diseases and conditions by targeting (e.g., binding to and/or acting on) human cells.

In some embodiments, the drug is an anti-cancer drug, and the human cells are cancer cells, which can be cells of a primary cancer or cells of cell lines established from a primary cancer. In these embodiments, a non-human animal of the present invention is transplanted with human cancer cells, and an anti-cancer drug is given to the non-human animal. The efficacy of the drug can be determined by assessing whether growth or metastasis of the human cancer cells in the non-human animal is inhibited as a result of the administration of the drug.

In specific embodiments, the anti-cancer drug is an antibody molecule, which binds to an antigen on human cancer cells. In particular embodiments, the anti-cancer drug is a bi-specific antibody that binds to an antigen on human cancer cells, and to an antigen on other human cells, for example, cells of the human immune system (or "human immune cells") such as B cells and T cells.

In some embodiments, a non-human animal of the present invention is engrafted with human immune cells or cells that differentiate into human immune cells. Such non-human animal with engrafted human immune cells is transplanted with human cancer cells, and is administered an anti-cancer drug, such as a bi-specific antibody that binds to an antigen on human cancer cells and to an antigen on human immune cells (e.g., T cells). The therapeutic efficacy of the bi-specific antibody can be evaluated based on its ability to inhibit growth or metastasis of the human cancer cells in the non-human animal. In a specific embodiment, the non-human animal of the present invention is engrafted with human CD34+ hematopoietic progenitor cells which give rise to human immune cells (including T cells, B cells, NK cells, among others). Human B cell lymphoma cells (e.g., Raji cells) are transplanted into such non-human animal with engrafted human immune cells, which is then administered with a bi-specific antibody that binds to tumor antigen (e.g., an antigen on normal B cells and certain B cell malignancies such as CD20) and to the CD3 subunit of the T cell receptor, to test the ability of the bi-specific antibody to inhibit tumor growth in the non-human animal.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Humanization of an Endogenous Cluster of Differentiation 47 (CD47) Gene This example illustrates exemplary methods of humanizing an endogenous gene encoding cluster of differentiation 47 (CD47) in a non-human mammal such as a rodent (e.g., a mouse). The methods described in this example can be employed to humanize an endogenous CD47 gene of a non-human animal using any human sequence, or combination of human sequences (or sequence fragments) as desired. In this example, a human CD47 gene that appears in bacterial artificial chromosome (BAC) clone RP11-69A17 is employed for humanizing an endogenous CD47 gene of a mouse.

A targeting vector for humanization of the genetic material encoding an extracellular N-terminal IgV domain and five transmembrane domains of an endogenous CD47 gene was constructed using VELOCIGENE® technology (see, e.g., U.S. Pat. No. 6,586,251 and Valenzuela el al. (2003) High-throughput engineering of the mouse genome coupled with high-resolution expression analysis, *Nature Biotech.* 21(6):652-659; incorporated herein by reference).

Briefly, mouse bacterial artification chromosome (BAC) clone RP23-230L20 (Invitrogen) was modified to delete the sequence containing exons 2-7 of an endogenous CD47 gene and insert exons 2-7 of a human CD47 gene using human BAC clone RP11-69A17 (Invitrogen), which encodes amino acids 16-292 of a human CD47 polypeptide. Endogenous DNA containing genomic DNA corresponding to exons 1, 8 and 9 of isoform 2 as well as the 5' and 3' untranslated regions (UTRs) were retained. Sequence analysis of the human CD47 sequence contained in BAC clone RP11-69A17 confirmed all CD47 exons and splicing signals. Sequence analysis revealed that the sequence matched the reference genome and CD47 transcripts NM_001777.3 and NM_198793.2. The genomic DNA corresponding to exons 2-7 of an endogenous CD47 gene (~30.8 kb) was replaced in BAC clone RP23-230L20 by homologous recombination in bacterial cells to insert a DNA fragment containing ~23.9 kb of genomic human DNA corresponding to exons 2-7 of a human CD47 gene from BAC clone RP11-69A17 and ~4995 bp corresponding to a self-deleting neomycin cassette flanked by recombinase recognition sites (loxP-hUb1-em7-Neo-pA-mPrm1-Crei-loxP; see U.S. Pat. Nos. 8,697,851, 8,518,392 and 8,354,389, which are incorporated herein by reference). The self-deleting neomycin cassette was added to the end of the ~23.9 kb human DNA fragment containing exons 2-7 of the human CD47 gene (FIG. 2). The targeting vector contained, from 5' to 3', a 5' homology arm containing ~39 kb of mouse genomic DNA from BAC clone RP23-230L20, ~29.3 kb of human genomic DNA from BAC clone RP11-69A17 (containing exons 2-7 of a human CD47 gene), a self-deleting neomycin cassette flanked by loxP sites, and ~98.8 kb of mouse genomic DNA from BAC clone RP23-

230L20. After homolgous recombination in bacterial cells with the targeting vector described above, a modified RP23-230L20 BAC clone was created that resulted in a humanized CD47 gene which contained a mouse 5' UTR, a mouse exon 1, human exons 2-7, mouse exons 8-9 and a mouse 3'UTR. Protein sequences of four projected alternatively spliced isoforms of humanized CD47 are provided in Table 3 which indicate the resulting mouse and human amino acids encoded by the mouse and human DNA, respectively.

Figure 3:
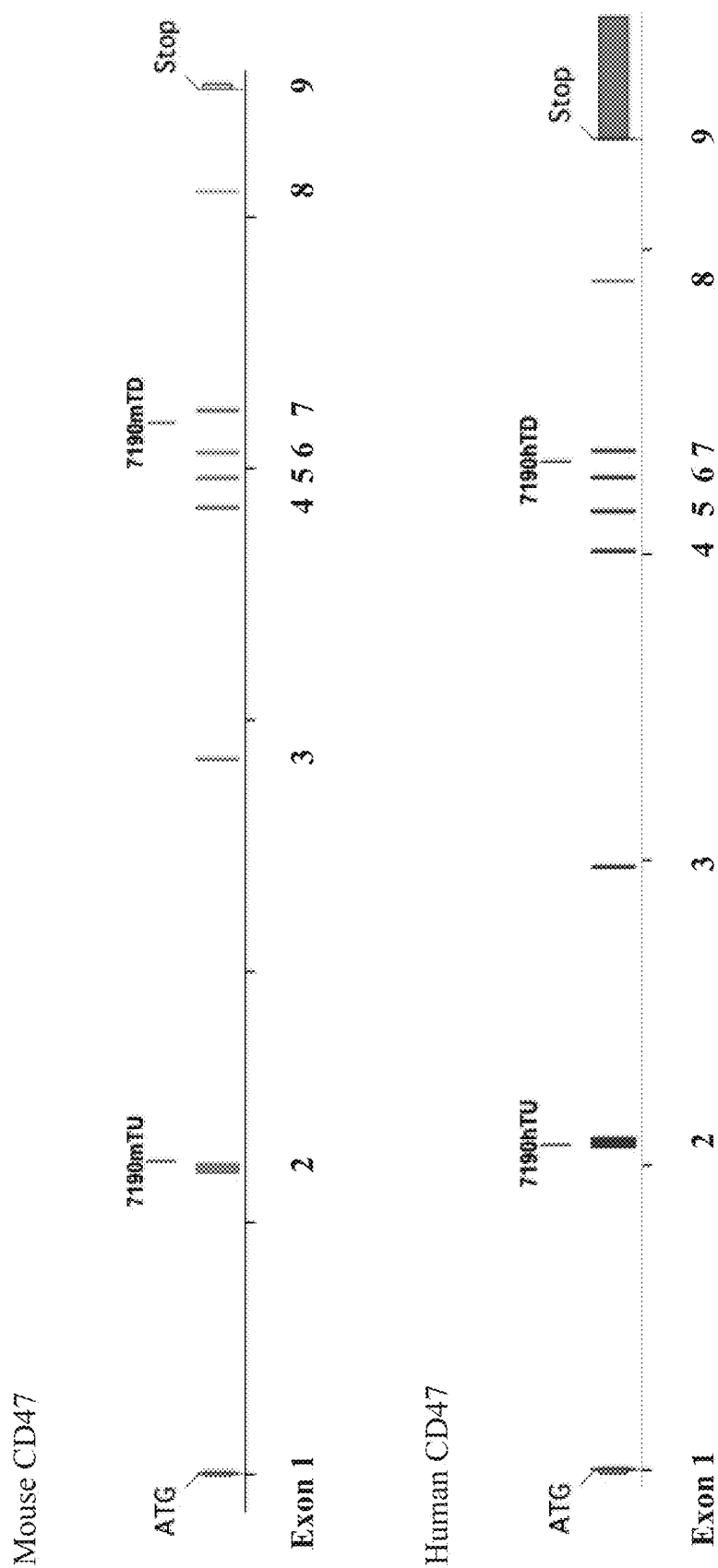
FIG. 3 shows a diagram, not to scale, of the genomic organization of a mouse and human Cluster of Differentiation 47 (CD47) genes. Locations of probes used in an assay described in Example 1 are indicated.

The modified BAC clone described above was used to electroporate F1H4 (50% 129/S6/SvEv/Tac, 50% C57BL/6NTac; Auerbach, W. et al. (2000) Biotechniques 29(5): 1024-8, 1030, 1032) mouse embryonic stem (ES) cells to create modified ES cells comprising an endogenous CD47 gene that is humanized from exons 2-7. Positively targeted ES cells containing a humanized CD47 gene were identified by an assay (Valenzuela el al., supra) that detected the presence of the human CD47 sequences (e.g., exons 2-7) and confirmed the loss and/or retention of mouse CD47 sequences (e.g., exons 1, 8 and 9 and/or exons 2-7). Table 4 sets forth the primers and probes that were used to confirm humanization of an endogenous CD47 gene as described above (FIG. 3). The nucleotide sequence across the upstream insertion point included the following, which indicates endogenous mouse sequence upstream of the insertion point (contained within the parentheses below with an AsiSI restriction site italicized) linked contiguously to a human CD47 sequence present at the insertion point:

```
                                      (SEQ ID NO: 33)
(GCAGACATGA TTACTTCAGA GCTTTCAAAG

CTAGATACTG TACCTTGCAT ATTCCAACAC)

GCGATCGC ATTTTAAGAT TTTCCATCCT

AGTGGAAAGA TATGATTGA TTCATCCTAT

TTACTTTGTA TATTAAAGTA CAGTAGAACC

TGCCACTTTT.
```

The nucleotide sequence across the downstream insertion point at the 5' end of the self-deleting neomycin cassette included the following, which indicates human CD47 genomic sequence contiguous with cassette sequence downstream of the insertion point (contained within the parentheses below with loxP sequence italicized):

```
                                      (SEQ ID NO: 34)
GGATCCATTT TAAGTAATAG AATAGGATTT

TTAATTGTTC CAGTGTTTCT GTGATAGAGC

TGTCCTGCAC AGACCTGTTT (CTCGAGATAA

CTTCGTATAA TGTATGCTAT ACGAAGTTAT

ATGCATGGCC TCCGCGCCGG GTTTTGGCGC

CTCCCGCGGG).
```

The nucleotide sequence across the downstream insertion point at the 3' end of the neomycin cassette included the following, which indicates cassette sequence contiguous with mouse genomic sequence 3' of exon 7 of an endogenous CD47 gene (contained within the parentheses below with loxP sequence italicized):

```
                                      (SEQ ID NO: 35)
CATGTCTGGA ATAACTTCGT ATAATGTATG

CTATACGAAG TTATGCTAGT AACTATAACG

GTCCTAAGGT AGCGACTAGC (ATTAGTATGG

AAGGTCCGTC CACTGTCCAG GTTCCTCTTG

CGGAGCTCTT TGTCTCTCTG GACTCTGTAT

ACACTGCTTG).
```

The nucleotide sequence across the downstream insertion point after deletion of the neomycin cassette (76 bp remaining) included the following, which indicates human and mouse genomic sequence juxtaposed with remaining cassette sequence loxP sequence (contained within the parentheses below with loxP sequence italicized):

```
                                      (SEQ ID NO: 36)
GGATCCATTT TAAGTAATAG AATAGGATTT TTAATTGTTC

CAGTGTTTCT GTGATAGAGC TGTCCTGCAC AGACCTGTTT (CTCGAGATAA CTTCGTATAA TGTATGCTAT ACGAAGTTAT

GCTAGTAACT ATAACGGTCC TAAGGTAGCG ACTAGC)ATT

AGTATGGAAG GTCCGTCCAC TGTCCAGGTT CCTCTTGCGG

AGCTCTTTGT CTCTCTGGAC TCTGTATACA CTGCTTGCAT.
```

Positive ES cell clones were then used to implant female mice using the VELOCIMOUSE® method (see, e.g., U.S. Pat. No. 7,294,754 and Poueymirou et al., F0 generation mice that are essentially fully derived from the donor gene-targeted ES cells allowing immediate phenotypic analyses, 2007, *Nature Biotech.* 25(1):91-99) to generate a litter of pups containing an insertion of exons 2-7 of a human CD47 gene into an endogenous CD47 gene of a mouse. Mice bearing the humanization of exons 2-7 of an endogenous CD47 gene were again confirmed and identified by genotyping of DNA isolated from tail snips using a modification of allele assay (Valenzuela et al., supra) that detected the presence of the human CD47 gene sequences. Pups are genotyped and cohorts of animals heterozygous for the humanized CD47 gene construct are selected for characterization.

TABLE 4

| Name | Primer | Sequence (5'-3') |
| --- | --- | --- |
| 7190mTU | Forward | TGCAGAAGTC ACTAGGAGGAAT (SEQ ID NO: 21) |
|  | Probe | TCAGTCAACTTCTTC TGGGTTGTTTCC (SEQ ID NO: 22) |
|  | Reverse | GTGCCAGACTCA CTTTCTATCCA (SEQ ID NO: 23) |

TABLE 4-continued

| Name | Primer | Sequence (5'-3') |
|---|---|---|
| 7190mTD | Forward | TGCTGCCAATA TACGGCTTCTG (SEQ ID NO: 24) |
| | Probe | CAGCTCTCATA GCCAACTATGG TGCC (SEQ ID NO: 25) |
| | Reverse | TCAAGCAGAGC CTGGTTATCTG (SEQ ID NO: 26) |
| 7190hTU | Forward | GTCGTCATTCC ATGCTTTGTTAC (SEQ ID NO: 27) |
| | Probe | TGGAGGCACAAA ACACTACTGAAG TATACG (SEQ ID NO: 28) |
| | Reverse | GGACAGTGGACT TGTTTAGAGC (SEQ ID NO: 29) |
| 7190hTD | Forward | GGCTTGGTGGCT GATTGTTCT (SEQ ID NO: 30) |
| | Probe | AGCACCCAAACT GATATGCCTGTA TTTG (SEQ ID NO: 31) |
| | Reverse | TGGGAACTGGTG TTTCAAGTCTA (SEQ ID NO: 32) |

Example 2. Expression of Humanized CD47 Polypeptide by Mouse Red Blood Cells

This Example demonstrates that non-human animals (e.g., rodents) modified to contain a humanized CD47 gene according to Example 1 can be used to screen CD47 modulators (e.g., anti-CD47 antibodies) and determine various characterisitics such as, for example, pharamcokinetics and safety profiles. In this Example, several anti-CD47 antibodies are screened on mouse red blood cells (RBCs) isolated from rodents made in accordance with Example 1, which rodents express a humanized CD47 polypeptide as described herein.

Briefly, 2 mL of whole blood from humanized CD47 mice (n=2) was transferred to a 15 mL tube and centrifuged at 200×g for 10 minutes at 4° C. The plasma and buffy coat were aspirated and then 15 mL of PBS was added and the cells were mixed gently. The mixture was centrifuged again at 200×g for five minutes at 4° C. The supernatant was aspirated and the cells were washed two additional times. Pelleted RBCs were resuspended to a final volume in 10 mL of PBS. The resuspended RBCs were centrifuged a final time at 200×g for 10 minutes at 4° C. The volume of packed RBCs was estimated 0.5 mL and diluted to a concentration of 0.5% with PBS (0.5 mL packed RBC/100 mL PBS). Actual RBC concentration was determined with a Cellometer Auto T4 (1.5×10$^7$/mL; Nexcelom Bioscience).

Figure 4:
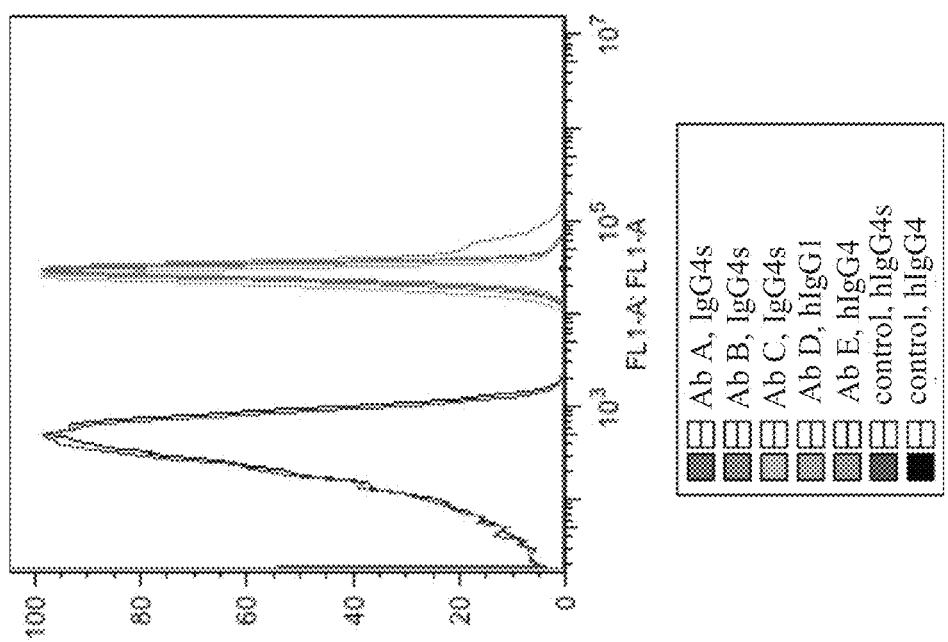
FIG. 4 shows an exemplary histogram of CD47 expression in red blood cells from humanized CD47 mice detected by anti-CD47 antibodies. Ab A, Ab B, Ab C, Ab D and Ab E: anti-CD47 antibodies; hIgG4s: human IgG4 of irrelevant specificity with modified Fc region that has reduced effector function; hIgG4: human IgG4 antibody of irrelevant specificity.

Eighty (80) μL of 0.5% mouse RBCs were added to each well of a 96-well V-bottom plate. Anti-CD47 antibodies were added into each well (20 μL at 33 nM). The plate was gently tapped to mix and incubated on ice for 30 minutes. The plate was then washed twice with staining buffer (PBS with 2% FBS). Secondary antibody Fab-488 (Alexa Fluor 488-conjugated AffiniPure mouse anti-human IgG, F(ab')$_2$ fragment specific, Jackson Immuno Research) was added to each well at a concentration of 10 μg/mL. The plate was incubated again on ice for 30 minutes, followed by washing once with staining buffer. The cells in each well were resuspended in 200 μL of staining buffer and filtered through a 96-well filter plate. The cells in the plate were analyzed using the BD ACCUR™ C6 system (BD Biosciences). Exemplary results are shown in FIG. 4. The mean fluorescence intensity (MFI) above isotype control for each tested antibody is shown in Table 5.

TABLE 5

| Antibody | MFI | Fold above isotype control |
|---|---|---|
| Ab A, hIgG4s | 28898 | 258 |
| Ab B, hIgG4s | 27545 | 246 |
| Ab C, hIgG4s | 24620 | 220 |
| Ab D, hIgG1 | 29882 | 267 |
| Ab E, hIgG4 | 33423 | 298 |
| Control, hIgG4s | 112 | — |
| Control, hIgG4 | 112 | — | hIgG4s: human IgG4 with modified Fc region that has reduced effector function

As shown in FIG. 4, all anti-CD47 antibodies bound to RBCs from humanized CD47 mice. Taken together, this Example demonstrates that (1) non-human animals (e.g., rodents) engineered to contain a humanized CD47 gene as described herein express a humanized CD47 polypeptide on the surface of cells (e.g., RBCs) of the non-human animal, and (2) such cells are useful for screening CD47 modulators (e.g., CD47 antibodies) and determining the pharmacokinetic profiles of such modulators.

Example 3. Hemagglutination of Mouse Red Blood Cells Expressing Humanized CD47 Polypeptide This Example further demonstrates that non-human animals (e.g., rodents) modified to contain a humanized CD47 gene according to Example 1 can be used in various assays (e.g., hemagglutination assay) to screen CD47 modulators (e.g., anti-CD47 antibodies) and determine various characterisitics such as, for example, pharamcokinetics and safety profiles. In this Example, several anti-CD47 antibodies are screened on mouse red blood cells (RBCs) that express a humanized CD47 polypeptide as described herein to determine antibody concentration that promotes hemagglutination.

Briefly, RBCs from wild-type and humanized CD47 mice (n=2) were prepared as described in Example 2. Twenty (20) μL of anti-CD47 antibody (at 5-fold serial dilution) was added into wells 1-12 across a 96-well V-bottom plate followed by the addition of 80 μL of 0.5% mouse RBCs to all wells of the plate. The plates were tapped gently to mix and incubated at room temperature (24-27° C.) for 30 minutes. Agglutination endpoint was observed visually (i.e., RBCs settle to the bottom in negative samples, while RBCs agglutinate in positive samples). Exemplary results are shown in FIG. 5, with boxes to outline the wells that show heme-agglutination.

Figure 5:
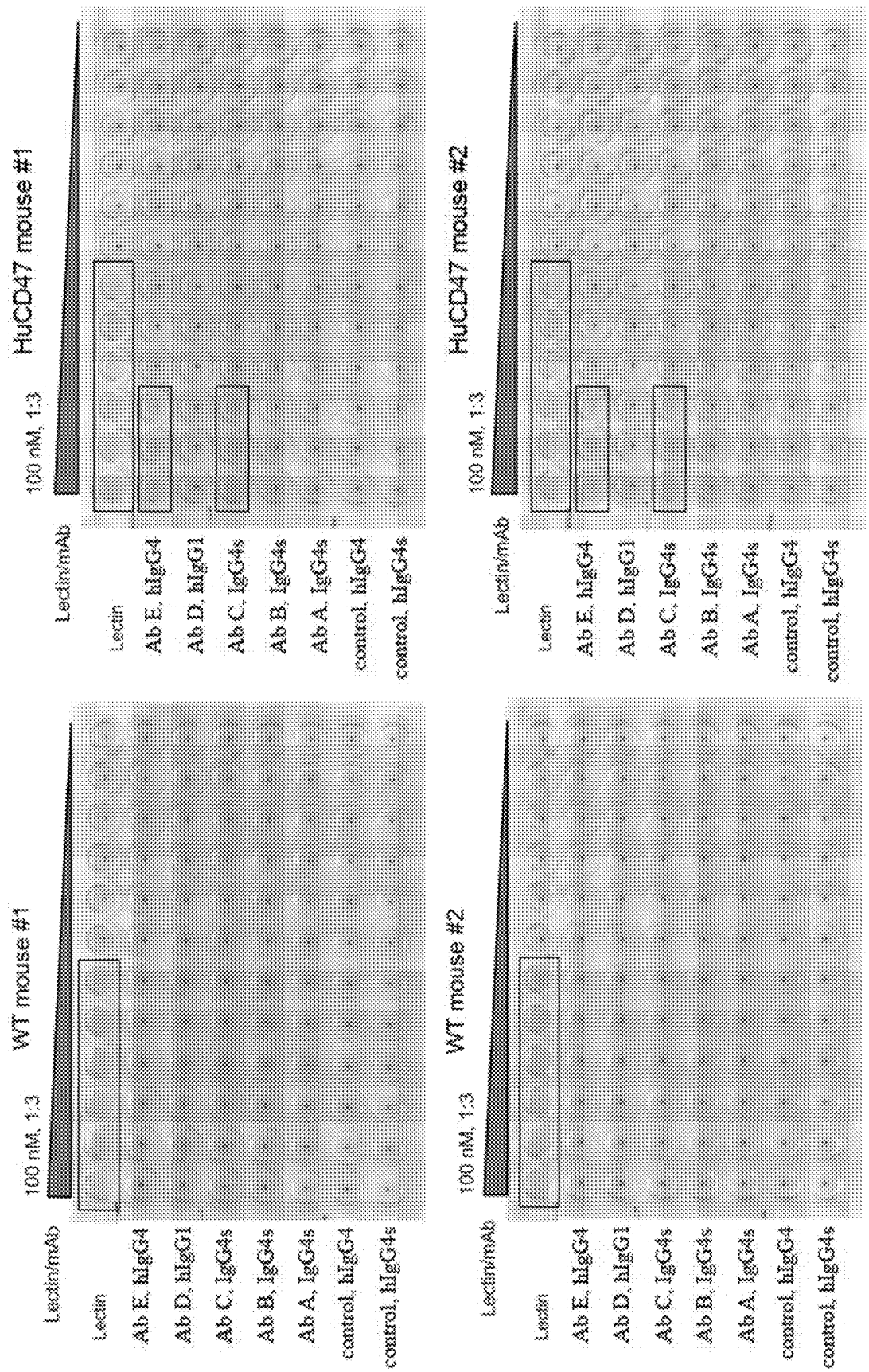
FIG. 5 shows exemplary hemagglutination of mouse red blood cells from wild-type (n=2) and humanized CD47 (n=2) mice by anti-CD47 antibodies. WT: wild-type; HuCD47: humanized CD47; Ab A, Ab B, Ab C, Ab D and Ab E: anti-CD47 antibodies; hIgG4s: human IgG4 of irrelevant specificity with modified Fc region that has reduced effector function; hIgG4: human IgG4 antibody of irrelevant specificity.

As shown in FIG. 5, only lectin caused agglutination in wild-type mice. However, two anti-CD47 antibodies (Ab E and Ab C) in addition to lectin induced agglutination in RBCs from two humanized CD47 rodents made according to Example 1. The concentration at which these two antibodies induced agglutination started from 11 nM. Taken together, this Example demonstrates that non-human animals (e.g., rodents) engineered to contain a humanized CD47 gene as describe herein can be used to assess one or more properties (e.g., hemagglutination) of CD47 modulators (e.g., CD47 antibodies).

Example 4. Pharmacokinetic Clearance of CD47 Modulators in Humanized CD47 Rodents This Example illustrates a method of assessing the pharmacokinetic clearance of CD47 modulators (e.g., anti-CD47 antibodies) in non-human animals (e.g., rodents) modified to contain a humanized CD47 gene according to Example 1. In this Example, wild-type and humanized CD47 rodents (e.g., mice) were administered anti-CD47 antibodies and serum levels of antibodies were determined using an ELISA assay.

Briefly, wild-type (n=5) or mice homozygous for humanized CD47 (n=5; as described above) were administered four anti-CD47 antibodies (Ab F, Ab G, Ab H and Ab I) and an IgG4s isotype control antibody (IgG4s). The genetic background of the mice were 75% CD57BL/6 and 25% 129Sv. Each antibody was tested in five humanized CD47 rodents. All antibodies were administered subcutaneously at a dose of 50 mg/kg. One pre-bleed was collected one day prior to administration of antibody (day 0). Post-injection bleeds were collected at 6 hours, 1 day, 2 days, 3 days, 4 days, 7 days, 10 days and 14 days. Serum fractions from bleeds were separated and subjected to total human antibody analysis using an ELSA immunoassay.

Figure 6:
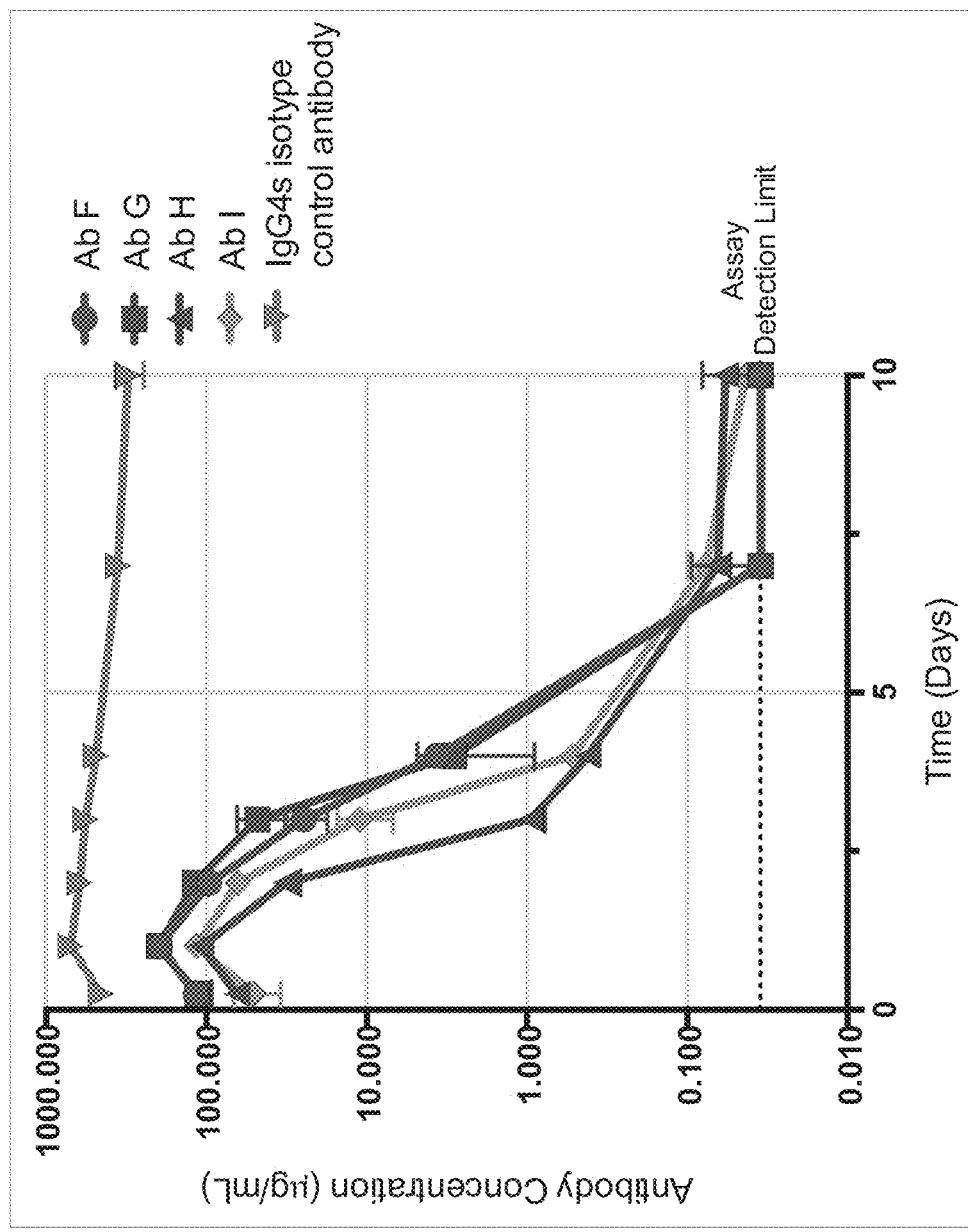
FIG. 6 shows exemplary pharmacokinetic profiles of anti-CD47 antibodies in humanized CD47 mice represented as antibody concentration (in µg/mL, y-axis) over time (in days, x-axis); Ab F, Ab G, Ab H and Ab I: anti-CD47 antibodies; hIgG4s: human IgG4 antibody of irrelevant specificity with modified Fc region that has reduced effector function.

Briefly, a goat anti-human IgG polyclonal antibody (Jackson ImmunoResearch) was coated onto 96-well plates to capture the tested human antibodies in the sera, and then plate bound antibodies were detected using a goat anti-human IgG polyclonal antibody conjugated with horseradish peroxidase (Jackson ImmunoResearch) and TMB substrate (BD Pharmingen). The serum samples were in six-dose serial dilutions and reference standards of the respective antibodies in 12-dose serial dilutions. Drug antibody concentrations in the sera were calculated based on the reference standard curve generated using Graphpad Prism software. Exemplary results are shown in FIG. 6 and Table 6.

The data demonstrated that the antibodies administered to wild-type and humanized mice as described herein were well tolerated. Taken together, this Example demonstrates that non-human animals of the present invention can be used to assess one or more pharmacokinetic properties of a drug targeting CD47 (e.g., an anti-CD47 antibody) such as, for example, circulating drug levels. Moreover, non-human animals described herein can be used to assess the toxicity of a drug targeting CD47 by determining adverse effects after administration.

TABLE 6

| | Serum antibody concentrations (μg/mL ± SEM) | | | | | | |
|---|---|---|---|---|---|---|---|
| Antibody | 6 hour | Day 1 | Day 2 | Day 3 | Day 4 | Day 7 | Day 10 |
| Ab F | 116.7 ± 14.0 | 196.4 ± 10.6 | 96.0 ± 13.3 | 24.7 ± 7.0 | 3.7 ± 0.42 | <0.35 | <0.35 |
| Ab G | 115.0 ± 22.1 | 198.8 ± 23.4 | 118.4 ± 20.9 | 48.3 ± 16.0 | 2.9 ± 1.97 | <0.35 | <0.35 |
| Ab H | 64.5 ± 3.85 | 108.0 ± 5.13 | 32.0 ± 6.08 | 1.0 ± 0.2 | 0.4 ± 0.03 | 0.06 ± 0.03 | 0.05 ± 0.02 |
| Ab I | 51.1 ± 16.6 | 115.2 ± 14.8 | 63.8 ± 8.3 | 11.1 ± 4.2 | 0.5 ± 0.1 | 0.1 ± 0.02 | <0.35 |
| IgG4s isotype control | 458.2 ± 34.4 | 702.5 ± 32.3 | 616.6 ± 27.0 | 567.1 ± 39.5 | 488.9 ± 45.0 | 357.0 ± 51.1 | 307.6 ± 61.1 |

Example 5. Pharmacokinetic Profiles of CD47 Modulators in Humanzied CD47/SIRPα Rodents This Example illustrates a method of assessing the pharmacokinetic clearance of CD47 modulators (e.g., anti-CD47 antibodies) in non-human animals (e.g., rodents) modified to contain humanized CD47 (according to Example 1) and SIRPα genes. In particular, humanized CD47 rodents described herein were modified to further contain a humanized SIRPα gene that contains an endogenous portion and a human portion, which human portion encodes the extracellular domain of a human SIRPα protein (e.g., amino acids 28-362 of a human SIRPα protein) and which endogenous portion encodes an intracellular domain of an endogenous SIRPα protein (e.g., amino acids encoding transmembrane and intracellular portions of a murine SIRPα protein) as described in PCT/US14/56910, filed Sep. 23, 2014, which is incorporated herein by reference. Double humanized CD47/SIRPα mice were made by breeding humanized SIRPα mice to humanized CD47 mice. In this Example, double humanized CD47/SIRPα rodents (e.g., mice) were administered various anti-CD47 antibodies and their corresponding pharmacokinetic profiles were determined.

Briefly, groups of wild type (n=5) and mice homozygous for humanized CD47 and SIRPα genes (CD47$^{hu/hu}$SIRPα$^{hu/hu}$; n=5 per group) were administered selected anti-CD47 antibodies and an IgG4 isotype control antibody (hIgG4s). The genetic background of the mice were 75% CD57BL/6 and 25% 129Sv. All antibodies were administered in a single subcutaneous dose of 50 mg/kg. One pre-bleed was collected one day prior to administration of antibody (day 0). Post-injection bleeds were collected at 6 hours, 1 day, 2 days, 3 days, 4 days, 7 days and 10 days. Serum fractions from bleeds were separated and subjected to total human antibody analysis using an ELISA immunoassay (described above). Additionally, hematocrit levels were measured at 6 hours, 1 day, 2 days, 3 days, 4 days, 7 days and 10 days and a urine test was performed as needed (at 6 hours and when urine color deviated from yellow color) to determine red blood cell counts. Exemplary results are shown in FIGS. 7-9.

Figure 7:
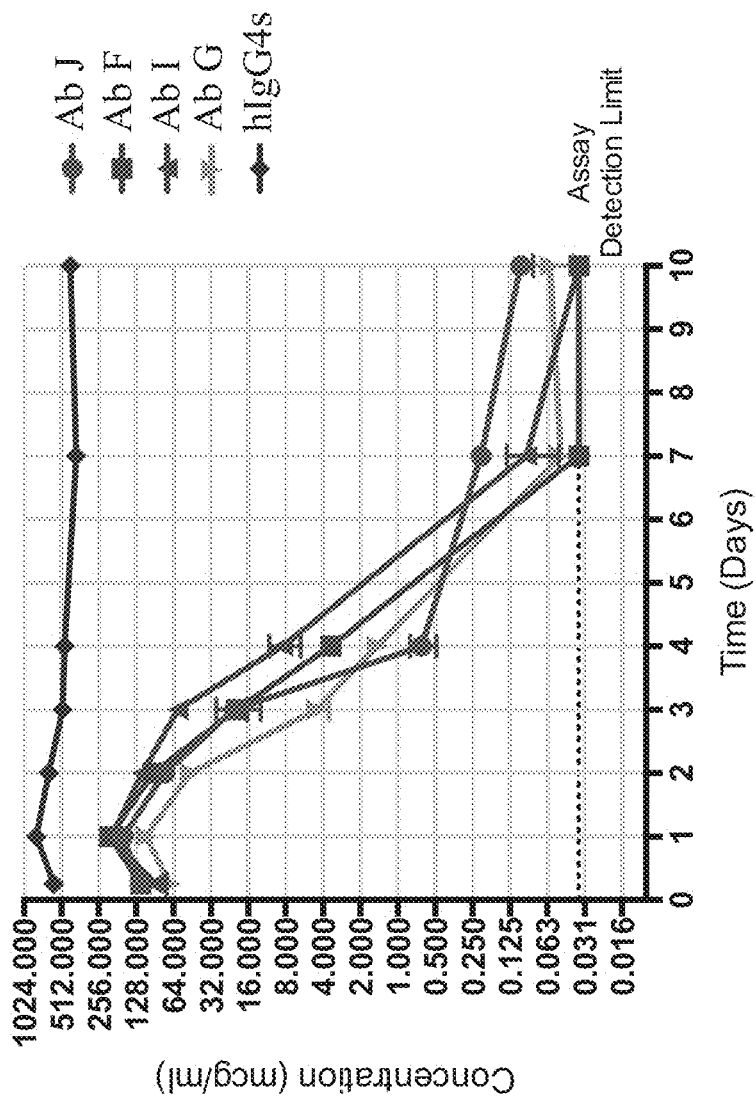
FIG. 7 shows exemplary pharmacokinetic profiles of anti-CD47 antibodies in humanized CD47/SIRPα mice (CD47$^{hu/hu}$SIRPα$^{hu/hu}$) represented as antibody concentration (in mcg/mL, y-axis) over time (in days, x-axis). Ab J, Ab F, Ab G and Ab I: anti-CD47 antibodies; hIgG4s: human IgG4 antibody of irrelevant specificity with modified Fc region that has reduced effector function.
Figure 8:
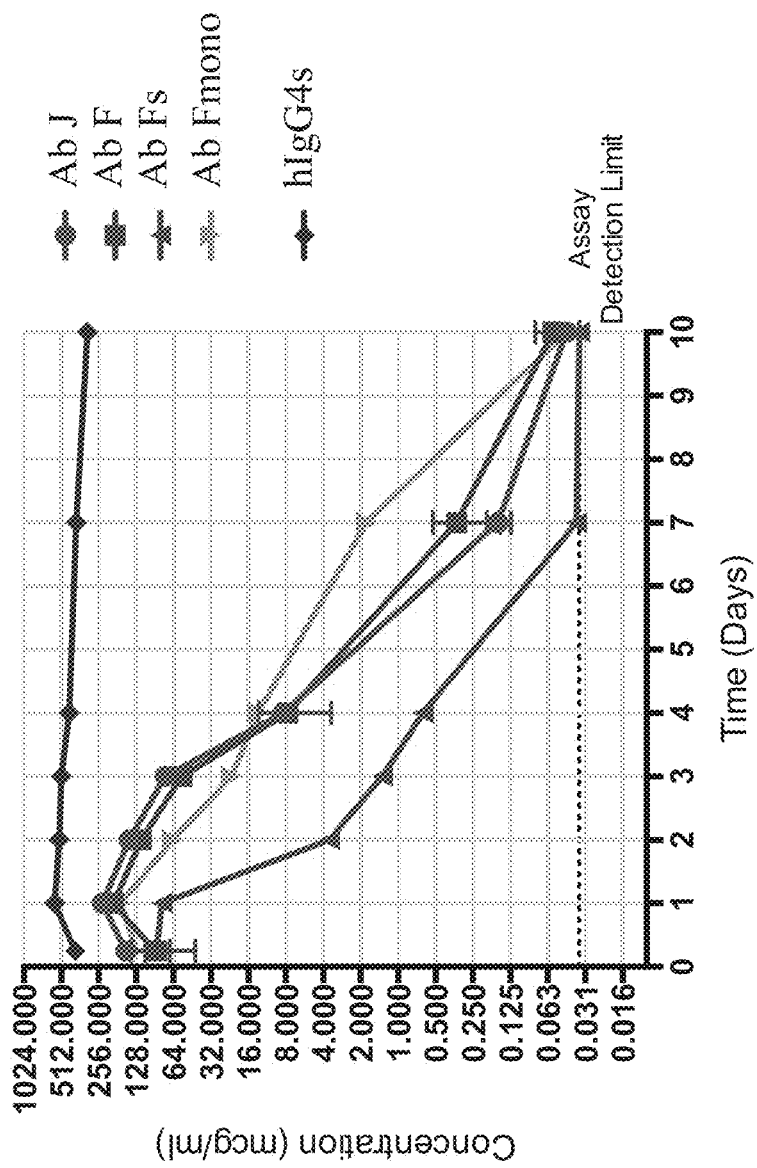
FIG. 8 shows exemplary pharmacokinetic profiles of anti-CD47 antibodies in humanized CD47/SIRPα mice (CD47$^{hu/hu}$SIRPα$^{hu/hu}$) represented as antibody concentration (in mcg/mL, y-axis) over time (in days, x-axis). Ab J, Ab F: anti-CD47 antibodies; Ab Fs: Ab F with modified Fc region that has reduced effector function; Ab Fmono: monovalent version of Ab F; hIgG4s: human IgG4 antibody of irrelevant specificity with modified Fc region that has reduced effector function.
Figure 9:
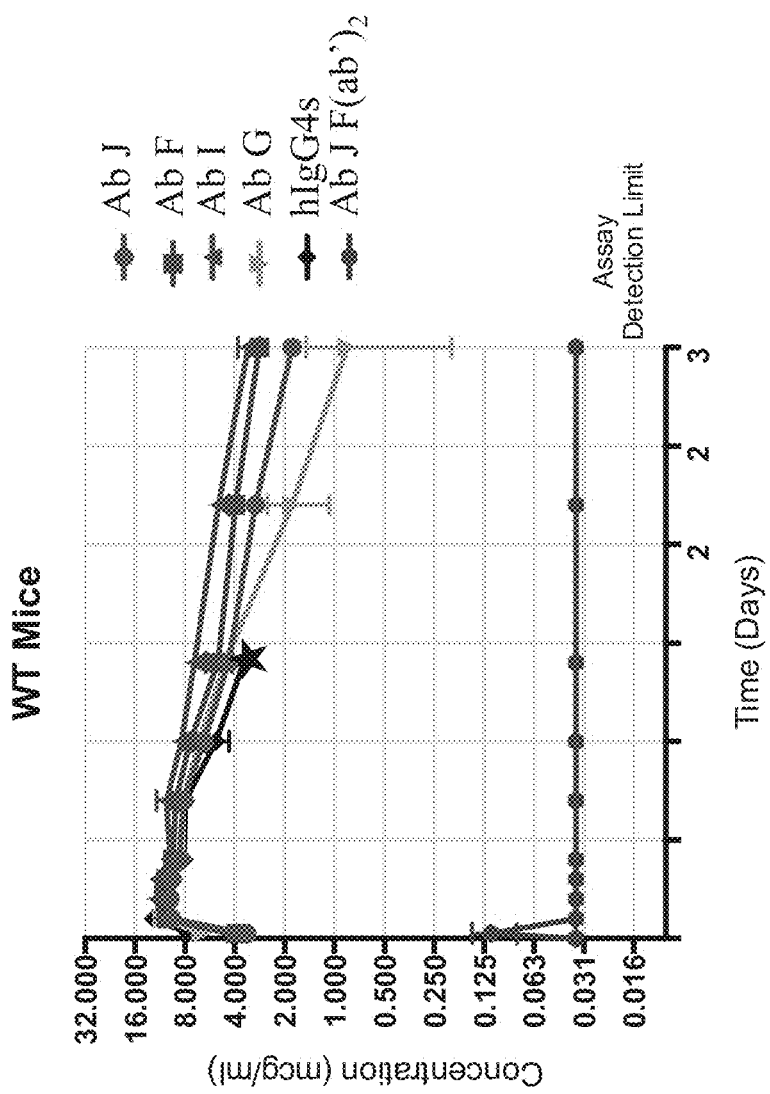
FIG. 9 shows exemplary pharmacokinetic profiles of anti-CD47 antibodies in wild type mice represented as antibody concentration (in mcg/mL, y-axis) over time (in days, x-axis). Mice demonstrating mouse anti-human antibody response (MAHA) were excluded. Ab J, Ab F, Ab I and Ab G: anti-CD47 antibodies; hIgG4s: human IgG4 antibody of irrelevant specificity with modified Fc region that has reduced effector function (star: all points after 15 days were excluded from hIgG4s treatment group due to MAHA); Ab J F(ab')$_2$: F(ab')$_2$ fragment of Ab J.

As shown in FIGS. 7 and 8, all anti-CD47 antibodies demonstrated target-mediated clearance in CD47$^{hu/hu}$SIRPα$^{hu/hu}$ mice and, in particular, many demonstrated similar pharmacokinetic profiles. Further, a monovalent version of one anti-CD47 antibody (Ab F) demonstrated greater bioavailability than its bivalent equivalent (FIG. 8). The inventors observed similar pharmacokinetic profiles for the antibodies among multiple experiments with humanized CD47 and double humanized animals (i.e., CD47$^{hu/hu}$SIRPα$^{hu/hu}$ mice).

Ab J had less of an effect on hematocrit levels than other anti-CD47 antibodies tested (Ab F, Ab G, Ab I, etc.) and comparable changes in hematocrit levels to control (hIgG4s) in CD47$^{hu/hu}$SIRPα$^{hu/hu}$ mice. Measurements of hematocrit on days 2-4 showed the largest drop from normal range (~38.5-45.1%), which included groups administered Abs F, G and I. In particular, a monovalent form of Ab F demonstrated a delayed lowering effect on hematocrit as compared to other antibodies tested. The inventors reasoned that differences in hematocrit levels among the various treatment groups could be attributed to a difference in epitope recognized by the various antibodies. Also, mice dosed with selected anti-CD47 antibodies demonstrated positive urine dipstick tests for heme at 6 hours. For example, Ab J and Ab F treatment groups each had one mouse positive for heme on day 1, while all other timepoints were negative. No significant weight loss (>20%) was observed in any treatment group.

Taken together, this Example demonstrates that non-human animals of the present invention provide an in vivo system for assessing the pharmacokinetic properties and/or profiles of one or more drugs targeting CD47 (e.g., one or more anti-CD47 antibodies) such as, for example, circulating drug levels. Moreover, non-human animals as described herein engineered to further contain other humanized genes (e.g., humanized SIRPα) can be used to assess the target-mediated clearance of one or more drugs targeting CD47.

EQUIVALENTS

Having thus described several aspects of at least one embodiment of this invention, it is to be appreciated by those skilled in the art that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Those skilled in the art will appreciate typical standards of deviation or error attributable to values obtained in assays or other processes described herein.

The publications, websites and other reference materials referenced herein to describe the background of the invention and to provide additional detail regarding its practice are hereby incorporated by reference.

We claim:

1. A genetically modified mouse whose genome comprises a replacement of a genomic fragment comprising exons 2-7 of a mouse CD47 gene at an endogenous mouse CD47 locus with a human genomic fragment comprising exons 2-7 of a human CD47 gene to form a humanized CD47 gene,
wherein the exons of the humanized CD47 gene consist of exon 1 of the mouse CD47 gene, exons 2-7 of the human CD47 gene, and the remaining exons downstream of exon 7 of the mouse CD47 gene,
wherein exons 2-7 of the human CD47 gene encode an amino acid sequence that is at least 98% identical with the amino acid sequence as set forth in amino acids 16-292 of SEQ ID NO: 10,
wherein the humanized CD47 gene is under control of the endogenous mouse CD47 promoter at the endogenous mouse CD47 locus, and
wherein the mouse expresses a humanized CD47 protein encoded by the humanized CD47 gene.

2. The genetically modified mouse of claim 1, whose genome further comprises a replacement of a genomic fragment comprising exons 2, 3 and 4 of a mouse SIRPα gene at an endogenous mouse SIRPα locus with a genomic fragment comprising exons 2, 3 and 4 of a human SIRPα gene to form a humanized SIRPα gene, wherein the humanized SIRPα gene is operably linked to the endogenous mouse SIRPα promoter at the endogenous mouse SIRPα locus, and wherein the humanized SIRPα gene encodes a humanized SIRPα protein comprising an extracellular portion of the human SIRPα protein encoded by the human SIRPα gene and an intracellular portion of the endogenous mouse SIRPα protein encoded by the mouse SIRPα gene.

3. The genetically modified mouse of claim 2, wherein the humanized SIRPα gene comprises exons 1, 5, 6, 7 and 8 of the mouse SIRPα gene.

4. An isolated cell obtained from a genetically modified mouse, wherein the genome of the cell and the genome of the mouse comprise a replacement of a genomic fragment comprising exons 2-7 of a mouse CD47 gene at an endogenous mouse CD47 locus with a human genomic fragment comprising exons 2-7 of a human CD47 gene to form a humanized CD47 gene,
wherein the exons of the humanized CD47 gene consist of exon 1 of the mouse CD47 gene, exons 2-7 of the human CD47 gene, and the remaining exons downstream of exon 7 of the mouse CD47 gene,
wherein exons 2-7 of the human CD47 gene encode an amino acid sequence that is at least 98% identical with the amino acid sequence as set forth in amino acids 16-292 of SEQ ID NO: 10,
wherein the humanized CD47 gene is under control of the endogenous mouse CD47 promoter at the endogenous mouse CD47 locus, and
wherein the mouse expresses a humanized CD47 protein encoded by the humanized CD47 gene.

5. The isolated cell of claim 4, whose genome further comprises a replacement of a genomic fragment comprising exons 2, 3 and 4 of a mouse SIRPα gene at an endogenous mouse SIRPα locus with a genomic fragment comprising exons 2, 3 and 4 of a human SIRPα gene to form a humanized SIRPα gene, wherein the humanized SIRPα gene is operably linked to the endogenous mouse SIRPα promoter at the endogenous mouse SIRPα locus, and wherein the humanized SIRPα gene encodes a humanized SIRPα protein comprising an extracellular portion of the human SIRPα protein encoded by the human SIRPα gene and an intracellular portion of the mouse SIRPα protein encoded by the mouse SIRPα gene.

6. The isolated cell of claim 5, wherein the humanized SIRPα gene comprises exons 1, 5, 6, 7 and 8 of the mouse SIRPα gene.

7. An isolated mouse embryonic stem (ES) cell whose genome comprises a replacement of a genomic fragment comprising exons 2-7 of a mouse CD47 gene at an endogenous mouse CD47 locus with a human genomic fragment comprising exons 2-7 of a human CD47 gene to form a humanized CD47 gene,
wherein the exons of the humanized CD47 gene consist of exon 1 of the mouse CD47 gene, exons 2-7 of the human CD47 gene, and the remaining exons downstream of exon 7 of the mouse CD47 gene,
wherein exons 2-7 of the human CD47 gene encode an amino acid sequence that is at least 98% identical with the amino acid sequence as set forth in amino acids 16-292 of SEQ ID NO: 10,
wherein the humanized CD47 gene is under control of the endogenous mouse CD47 promoter at the endogenous mouse CD47 locus,
wherein the embryonic stem cell is capable of generating a mouse whose genome comprises said humanized CD47 gene, wherein the mouse expresses the humanized CD47 protein encoded by the humanized CD47 gene.

8. A mouse embryo comprising the mouse embryonic stem cell of claim 7.

9. A method of making a genetically modified mouse, comprising:
   (a) modifying a mouse embryonic stem cell by replacing a genomic fragment comprising exons 2-7 of a mouse CD47 gene at an endogenous mouse CD47 locus with a human genomic fragment comprising exons 2-7 of a human CD47 gene to form a humanized CD47 gene,
   wherein the exons of the humanized CD47 gene consist of exon 1 of the mouse CD47 gene, exons 2-7 of the human CD47 gene, and the remaining exons downstream of exon 7 of the mouse CD47 gene,
   wherein exons 2-7 of the human CD47 gene encode an amino acid sequence that is at least 98% identical with the amino acid sequence as set forth in amino acids 16-292 of SEQ ID NO: 10, and
   wherein the humanized CD47 gene is under control of the endogenous mouse CD47 promoter at the endogenous mouse CD47 locus;
   (b) obtaining a genetically modified mouse embryonic stem cell comprising the humanized CD47 gene from step (a); and,
   (c) generating a genetically modified mouse from the genetically modified mouse embryonic stem cell of step (b), wherein the mouse expresses a humanized CD47 protein encoded by the humanized CD47 gene.

10. An isolated tissue obtained from a genetically modified mouse, wherein the genome of the cells in the tissue and the genome of the mouse comprise a replacement of a genomic fragment comprising exons 2-7 of a mouse CD47 gene at an endogenous mouse CD47 locus with a human genomic fragment comprising exons 2-7 of a human CD47 gene to form a humanized CD47 gene, wherein the exons of the humanized CD47 gene consist of exon 1 of the mouse CD47 gene, exons 2-7 of the human CD47 gene, and the remaining exons downstream of exon 7 of the mouse CD47 gene, wherein exons 2-7 of the human CD47 gene encode an amino acid sequence that is at least 98% identical with the amino acid sequence as set forth in amino acids 16-292 of SEQ ID NO: 10, wherein the humanized CD47 gene is under control of the endogenous mouse CD47 promoter at the endogenous mouse CD47 locus, and wherein the mouse expresses a humanized CD47 protein encoded by the humanized CD47 gene.

11. The isolated tissue of claim 10, wherein the genome of the cells in the tissue and the genome of the mouse further comprise a replacement of a genomic fragment comprising exons 2, 3 and 4 of a mouse SIRPα gene at an endogenous mouse SIRPα locus with a genomic fragment comprising exons 2, 3 and 4 of a human SIRPα gene to form a humanized SIRPα gene, wherein the humanized SIRPα gene is operably linked to the endogenous mouse SIRPα promoter at the endogenous mouse SIRPα locus, and wherein the humanized SIRPα gene encodes a humanized SIRPα protein comprising an extracellular portion of the human SIRPα protein encoded by the human SIRPα gene and an intracellular portion of the mouse SIRPα protein encoded by the mouse SIRPα gene.

12. The isolated tissue of claim 11, wherein the humanized SIRPα gene comprises exons 1, 5, 6, 7 and 8 of the mouse SIRPα gene.

* * * * *